United States Patent
Fujii et al.

(10) Patent No.: US 7,968,309 B2
(45) Date of Patent: Jun. 28, 2011

(54) METHOD FOR IMPROVING THE THERMOSTABILITY OF SUCROSE PHOSPHORYLASE (SP)

(75) Inventors: Kazutoshi Fujii, Osaka (JP); Masae Iiboshi, Kyoto (JP); Michiyo Yanase, Hyogo (JP); Hiroki Takata, Hyogo (JP); Takeshi Takaha, Hyogo (JP); Takashi Kuriki, Osaka (JP)

(73) Assignee: Ezaki Glico Co., Ltd., Osaka (JP)

( * ) Notice: Subject to any disclaimer, the term of this patent is extended or adjusted under 35 U.S.C. 154(b) by 840 days.

(21) Appl. No.: 10/566,224

(22) PCT Filed: Aug. 31, 2004

(86) PCT No.: PCT/JP2004/012533
§ 371 (c)(1),
(2), (4) Date: Apr. 8, 2008

(87) PCT Pub. No.: WO2005/024008
PCT Pub. Date: Mar. 17, 2005

(65) Prior Publication Data
US 2008/0206822 A1 Aug. 28, 2008

(30) Foreign Application Priority Data
Sep. 4, 2003 (JP) .................. 2003-313305

(51) Int. Cl.
*C12Q 1/48* (2006.01)
*C12N 9/12* (2006.01)
(52) U.S. Cl. ................... 435/15; 435/100; 435/194
(58) Field of Classification Search .................. 435/183, 435/194, 100
See application file for complete search history.

(56) References Cited

OTHER PUBLICATIONS

Tettelin et al Science 293, 498-506, 2001.*
International Search Report for corresponding Application No. PCT/JP2004/012533 mailed Dec. 28, 2004.
Pimental M.C.B. et al., "Screening Thermal Properties and Production in Yam Extract of Fungal Sucrose Phosphorylase", Revista de Microbiologia, 1992, vol. 23, pp. 199 to 205.
Lehmann M. et al., "Engineering Proteins for Thermostability; the Use of Sequence Alignments Versus Rational Design and Directed Evolution", Current opinion in Biotechnology, 2001, vol. 12, pp. 371 to 375.

* cited by examiner

*Primary Examiner* — Tekchand Saidha
(74) *Attorney, Agent, or Firm* — Renner, Otto, Boisselle & Sklar, LLP

(57) ABSTRACT

A sucrose phosphorylase (SP) having improved thermostability obtained by modifying a natural SP and a method for producing the SP having improved thermostability is provided. This SP having improved thermostability has an amino acid residue which is different from that of the natural sucrose phosphorylase, in at least one position selected from the group consisting of a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3, and wherein the enzyme activity of the SP having improved thermostability at 37° C., after heating the SP having improved thermostability in 20 mM Tris buffer (pH 7.0) at 55° C. for 20 minutes, is 20% or more of enzyme activity of the SP having improved thermostability at 37° C. before heating.

35 Claims, 4 Drawing Sheets

Fig. 1A

Position of motif sequence 3
→
D249
↓

```
StMuSP  238:HYTIQFKIADHDYYVYDFALPMVTLYSLYSGKVDRLAKWLKMSPMKQFTTLDTHDGIGVVDVKDILTDEEITYTSNELYK 317
StPSP   238:HYSIQFKIADHDYYVYDFALPMVTLYTLYSSRTERLAKWLKMSPMKQFTTLDTHDGIGVVDVKDILTDEEIDYASNELYK 317
StSSP   238:HYSIQFKIAEHDYFIYDFALPMVTLYSLYSGRVQRLADWLAKSPMKQFTTLDTHDGIGVVDVKDILTDEEIAYTSDQLYK 317
StMiSP  238:HYSIQFKIADHDYYVYDFALPMVTLYTLYSSRTERLAKWLKMSPMKQFTTLDTHDGIGVVDVKDILTDEEIDYASNELYK 317
LeuSP1  241:HYSIPKKINDHGYFTYDFALPMTTLYTLYSGKTNQLAKWLKMSPMKQFTTLDTHDGIGVVDARDILTDDEIDYASEQLYK 320
LeuSP2  241:HYTIPQKINAHGYFTYDFALPMTVLYTLYSGKTNRLANWLKQSPMKQFTTLDTHDGIGVVDARDILTDEEIDYASEELYK 320
OenSP   238:HYTIPAKINEYGYFTYDFVLPLVILYTLYSGNPKQLAKWLKMSPKKQFTTLDTHDGIGVVDARDILTDEEIDYTSSELYK 317
LBSP1   238:HYTMPFKVAEHGYFIYDFALPMVLLYSLYSGNSTQLAAWLKKCPMKQFTTLDTHDGLGVVDAKDILTDDQISYTTNELYK 317
LBSP2   238:HYSMPFKISKHGYYIYDFALPMVTLYSLYSGKSNRLADWLKKCPMKQFTTLDTHDGIGVVDARDILSPDEIKYTSNELYK 317
ListSP  238:HYSIQMKIANHDYYIYDFALPMVMLYSLYSGRVERLAKWLEMSPMKQFTTLDTHDGIGVVDARDLLTDEELDYTSAELYK 317
               *..*.*..*   ...  *..  .  .*  ...********.**..*****.**.**..*  *...     ...****.*

StMuSP  318:VGANVWRKYSTAEYNNLDIYQINSTYYSALGDDDQKYFLARLIQAFAPGIPQVYYVGFLAGKNDLELLESTKEGRNINRH 397
StPSP   318:VGANVKRKYSSAEYNNLDIYQINSTYYSALGDDDVKYFLARLIQAFAPGIPQIYYVGLLAGKNDLKLLEETKEGRNINRH 397
StSSP   318:VGANVWRKYSTAEYNNLDIYQINSTYYSALGDDDKKYFLARLIQAFAPGIPQVYYVGLLAGKNDLKLLEKTKEGRNINRH 397
StMiSP  318:VGANVKRKYSSAEYNNLDIYQINSTYYSALGDDDVKYFLARLIQAFAPGIPQVYYVGLLAGKNDLKLLEETKVGRNINRH 397
LeuSP1  321:VGANVKKTYSSASYNNLDIYQINSTYYSALGNDDAAYLLSRVFQVFAPGIPQIYYVGLLAGENDIALLESTKEGRNINRH 400
LeuSP2  321:VGANVKKTYSSAAYNNLDIYQINSTYYSALGNDDAAYLLSRVFQVFAPGIPQIYYVGLLAGENDIDLLESSKEGRNINRH 400
OenSP   318:VGANVKRTYSSAAYNNLDIYQINSTYYSALGNDDKAYLLARAIQIFAPGIPQIYYAGLLAGENDLDLLEKTKEGRNINRH 397
LBSP1   318:IGANVKKKYSSAEYHNLDIYQINTTYYSALGNDDKKYFIARLLQIFAPGIPQIYYVGLLAGENDIQLLEKTKEGRDINRH 397
LBSP2   318:VGANVKKKYSSAEYHNLDIYQINTTYYSALGNDDKKYFIARLIQMFAPGIPQVYYVGMLAGKNDIELLEKTKEGRNINRH 397
ListSP  318:IGANVKKIYSSEKYNNLDIYQINSTYYSALGDDDKSYLLARVIQCFAPGIPQIYYVGLLAGKNDIDLLEETKEGRNINRH 397
                 .****  .**...*.*********.****** **  .*...*..*  ********.**.*.***.**   *** . *.**.****

StMuSP  398:YYSSEEIAKEVKRPVVKALLNLFTYRNQSAAFDLDGRIEVETPNEATIVIERQNKDGSHIATAEINLQDM-TYRVTENDQ 476
StPSP   398:YYSNEEIAKEVQRPVVKALLNLFSFRNRSEAFDLEGTTEIETPTAHSIVIKRQNKDKSVTAVVEIDLQNQ-TYRVIEN-- 474
StSSP   398:YYSSEEIAHEVERPVVKALIKLFSYRNNSQAFDLDGSLETEVLDDHTIVIKRSNQDKSALAQAVINLQDL-TYQVTENGQ 476
StMiSP  398:YYSNEEIAEEVQRPVVKALLNLFSFRNRSVAFDLEGTIDVETPTAHSIVIKRQNKDKSVTAVAEIDLQNQ-TYRV----- 471
LeuSP1  401:YYTREEVKSEVKRPVVANLLKLLSWRNESPAFDLAGSITVDTPTDTTIVVTRQDENGQNKAVLTADAA-NKTFEIVENGQ 479
LeuSP2  401:YYTREEIKSAVKRPVVADLLALLSWRNQFSAFALDGTITVETPSEHDIKITRTDHSGDNIAILLANAK-TRTFVITANGK 479
OenSP   398:YYSEEEVANEVQRPIVACLLKLLAWRNRSAAFDLQGDIQVSATDKNEIKIIRTSTNGQDTAELTANVA-LKTFTIKENDK 476
LBSP1   398:YYDLDEIAEQVQRPVVKSLIKLLEFRNSVPAFDLEGSIKVETPSEHEIIVTRSNKAGTEVASTYVDFKNL-DYQVKYNDQ 476
```

Fig. 1B

```
StMuSP  477:T-ISFE------------        481
StPSP   475:----GVEV------------      478
StSSP   477:T-ITFE------------        481
StMiSP  472:------MRTEXKY--ILKT       482
LeuSP1  480:TVMSSD------NLTQN--       490
LeuSP2  480:TVLQNK------------        485
OenSP   477:IILIEDQTDT-KDI-----       489
LBSP1   477:VFNF--------------        480
LBSP2   477:VINF--------------        480
ListSP  477:N-ILI-------------        480
```

METHOD FOR IMPROVING THE THERMOSTABILITY OF SUCROSE PHOSPHORYLASE (SP)

TECHNICAL FIELD

The present invention relates to thermostable sucrose phosphorylase and a gene encoding said thermostable sucrose phosphorylase. Further, the present invention relates to a method of producing said thermostable sucrose phosphorylase.

BACKGROUND ART

Sucrose phosphorylase (hereinafter, also referred to as SP or SP enzyme) is an enzyme utilized for example in α-glucan synthesis and glucose-1-phosphate (G-1-P) synthesis.

α-Glucan (particularly insoluble amylose) is expected to have the same functions as those of dietary fibers and can be expected to be useful in health food. Further, an amylose that is a linear α-glucan has characteristics such as being capable of including, for example, iodine, fatty acids, and the like in its molecule, and can thus be expected to be useful in fields such as pharmaceuticals, cosmetics, and sanitary products. An amylose can also be utilized as a crude material for producing cyclodextrin and cycloamylose having an inclusion ability similar to that of amylose. Further, a film containing an amylose has tensile strength comparable to general-purpose plastics and is has good prospects as a raw material for biodegradable plastics. Thus, amylose is expected to be useful in various applications. However, substantially pure amylose is rarely obtained, is very expensive and is thus distributed only at the reagent level and is scarcely utilized as an industrial raw material. Accordingly, there is demand for a method of producing an amylose stably and inexpensively.

G-1-P is utilized, for example, as a medical antibacterial agent, an anti-tumor agent (as a platinum complex), as a drug for treating heart disease (as an amine salt) and a substrate for α-glucan synthesis.

SPs are reported to exist in some bacteria (bacteria of the genus *Streptococcus*, microorganisms of the genus *Leuconostoc*, *Escherichia coli*, lactic acid bacteria, and the like), and the amino acid sequences and base sequences of SPs found in these bacteria are known.

Various SPs can be used in the production of an α-glucan or G-1-P, and SP derived from bacteria of the genus *Leuconostoc* is often used. This is because a relatively large amount of the enzyme can be easily obtained.

In industrial production of an α-glucan, it is necessary to essentially remove other contaminating enzyme activities, particularly phosphatase activity and amylase activity. This is because if phosphatase is present during the synthesis of an α-glucan by SP and GP, G-1-P synthesized as a reaction intermediate is degraded to reduce the yield of the α-glucan. This is because if amylase is present, synthesized α-glucan is degraded to reduce the molecular weight thereof. Accordingly, it is necessary to remove these contaminating enzymes. *Escherichia coli* and *Bacillus subtilis* are desirable hosts for expressing an SP gene when producing a large amount of SP. However, as shown in FIGS. 2 and 3, *Escherichia coli* has amylase activity and phosphatase activity, and *Bacillus subtilis* has amylase activity. However, as shown in FIGS. 2 and 3, the enzymes possessed by these hosts cannot be inactivated by heat treatment at 55° C., but can be almost completely inactivated by heat treatment at a temperature of 60° C. Therefore, an SP having thermostability whereby its activity is not lost, even after heat treatment at 60° C., or an SP having higher thermostability than that of amylase or phosphatase has been desired.

For reference, specific numerical values of the amylase activity and phosphatase activity in cell extracts from various bacteria (*E. coli* TG-1, *E. coli* BL21, and *Bacillus subtilis* ANA-1) before and after heating are shown in the following Table 1.

TABLE 1

|  | Phosphatase activity (%) | | Amylase activity (%) | | |
| --- | --- | --- | --- | --- | --- |
|  | TG-1 | BL21 | TG-1 | BL21 | ANA-1 |
| Before heating | 100 | 100 | 100 | 100 | 100 |
| 50° C. | 99.1 | 98.6 | 21.6 | 28.6 | 33.8 |
| 55° C. | 60.9 | 74.5 | 9.1 | 9.7 | 19.8 |
| 60° C. | 2.9 | 3.1 | 0.4 | 0 | 3.0 |
| 65° C. | 2.5 | 2.0 | 0.9 | 0 | 2.4 |

However, an SP which has thermostability, particularly an SP which can maintain sufficient activity at high temperatures (for example 60° C. to 75° C.), is not known.

In production of an α-glucan or G-1-P, it is also preferable to conduct the reaction at temperatures as high as possible. This is because when the enzyme reaction is carried out at high temperatures, the reaction rate is generally increased and the operability of an α-glucan is improved. An α-Glucan, particularly an amylose, is aged and insolubilized to form precipitates or gel. This aging rate is well-known to depend on temperature. When the reaction temperature is low, there arise problems in operability at a later stage, such as gelation of the amylose solution after production. For carrying out the reaction at high temperatures, it is necessary that the enzyme be thermostable.

However, all of the bacteria described above are mesophilic bacteria, and an SP having thermostability which is derived from a bacteria, particularly an SP which can maintain sufficient activity at high temperatures (for example, 50° C. to 60° C.), is not known. Therefore, in the case of conventional SP, purification costs cannot be reduced by heating treatment, and the reaction cannot be carried out at high temperature either.

With respect to an SP derived from organisms other than bacteria (prokaryotes), an SP derived from mold (eukaryotes) is reported (see non-patent document 1). According to this reference, an SP derived from *Monilia sitophila* (also known as *Neurospora intermedia*) retains 90% or more of its activity after heating at 70° C. for 30 minutes.

However, the experimental results reported in this reference are obtained by using an SP of very low purity, so doubts remain as to whether the observed SP activity can be truly quantitatively measured SP activity. Further, many molds secrete amylase to the outside of the bacterial body, so it is necessary to highly purify the SP enzyme for use, and purification of the SP enzyme requires significant time and costs. It is impossible to introduce this mold-derived SP enzyme into a host secreting phosphatase and amylase in a lower amount using genetic recombination technology. This is because neither the amino acid sequence nor the base sequence of this mold-derived SP is known.

SP enzyme is reported to show an improvement in it's thermostability by immobilizing the enzyme, but the immobilized enzyme has disadvantages such as changes in substrate specificity, and there is a limit to the improvement of thermostability by immobilization, so it is desired to improve the thermostability of the SP enzyme itself. There are no reports of improving the thermostability of an SP enzyme by introduction of a mutation.

The apparent thermostability of SP enzyme is improved in the presence of sucrose at high concentrations (see Patent Document 1). However, there is a limit to the increase in thermostability achieved in the presence of sucrose at high concentrations, so it is desired to improve the thermostability of the SP enzyme itself.

In order to solve these problems, an SP which is advantageous for industrial utilization and has high thermostability is required.

Theoretical methods for making a general enzyme more thermostable, such as proline theory and amino acid substitution based on enzyme steric structure information have been tried, but have not necessarily succeeded. For this reason, methods based upon random mutation, or methods using a combination of random mutation and theoretical methodology is currently being carried out. However, in any of these methods, every protein must be characterized by trial and error.

Regarding enzymes other than SP, it has been reported that, once the position of a particular amino acid(s) involved in improving the thermostability of an enzyme is determined, an enzyme can be made thermostable by substitution of the specified amino acid residue(s) with other amino acid residues (for example see Non-Patent Documents 2 to 4).

(Patent Document 1)

International Publication No. 02/097077 Pamphlet (Non-Patent Document 1)

M. C. B. Pimentel et al., "SCREENING, THERMAL PROPERTIES AND PRODUCTION IN YAM EXTRACT OF FUNGAL SUCROSE PHOSPHORYLASE", Rev. Microbiol., Sao Paulo, 1992, 23(3), pp. 199-205

(Non-Patent Document 2)

Martin Lehmann and Markus Wyss: "Engineering proteins for thermostability: the use of sequence alignments versus rational design and directed evolution", Current Opinion in Biotechnology, 2001, 12, pp. 371-375

(Non-Patent Document 3)

M. Lehmann et al., "The consensus concept for thermostability engineering of proteins", Biochemica Biophysica Acta, 2000, 1543, pp. 408-415

(Non-Patent Document 4)

Junichi Miyazaki et al., "Ancestral Residues Stabilizing 3-Isopropylmalate Dehydrogenase of an Extreme Thermophile: Experimental Evidence Supporting the Thermophilic Common Ancestor Hypothesis", J. Biochem., 2001, 129, pp. 777-782

DISCLOSURE OF INVENTION

Problems to be Solved by the Invention

The present invention intends to solve the aforementioned problems, and an object of the present of invention is to provide a sucrose phosphorylase which has better thermostability than the conventional sucrose phosphorylase.

Means for Solving the Problems

In order to solve the aforementioned problems by improving the thermostability of an SP, of which the sequence is known, the present inventors continued to intensively study and, as a result, finally found that by substituting an amino acid residue in a specific position of the sequence of a SP, resulted in an SP having improved thermostability, which resulted in completion of the invention the present application is based on.

The sucrose phosphorylase having improved thermostability of the present invention is a sucrose phosphorylase having improved thermostability, obtained by modifying a natural sucrose phosphorylase, wherein the sucrose phosphorylase having improved thermostability has an amino acid residue which is different from that of the natural sucrose phosphorylase, in at least one position selected from the group consisting of:

a position corresponding to position 14, a position corresponding to position 29 and a position corresponding to position 44 in motif sequence 1: AVGGVHLLPFFPSTGDRGFAPIDYHEVDSAFGDWDDVKRLGEKYYLMFDFMINHIS (SEQ ID NO. 25);

a position corresponding to position 7, a position corresponding to position 19, a position corresponding to position 23 and a position corresponding to position 34 in motif sequence 2: RPTQEDVDLIYKRKDRAPKQEIQFADGSVEHLWNTFGEEQID (SEQ ID NO. 26); and a position corresponding to position 19 in motif sequence 3: ILPEIHEHYTIQFKIADHDYYVYDFALPMVTLYSLYSG (SEQ ID NO. 27); and wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating.

In one embodiment, the amino acid sequence of the natural sucrose phosphorylase can have at least 40% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the natural sucrose phosphorylase can have at least 60% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the natural sucrose phosphorylase can be encoded by a nucleic acid molecule hybridizing under stringent conditions with a nucleic acid molecule consisting of a base sequence encoding an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the natural sucrose phosphorylase can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the natural sucrose phosphorylase can be derived from a bacterium selected from the group consisting of *Streptococcus mutans, Streptococcus pneumoniae, Streptococcus sorbinus, Streptococcus mitis, Leuconostoc mesenteroides, Oenococcus oeni, Lactobacillus acidophilus* and *Listeria monocytogenes*.

In one embodiment, the natural sucrose phosphorylase can be derived from *Streptococcus mutans, Streptococcus pneumoniae, Streptococcus sorbinus* or *Streptococcus mitis*.

In one embodiment, the natural sucrose phosphorylase can be derived from *Streptococcus mutans* or *Leuconostoc mesenteroides*.

In one embodiment, the amino acid residue in a position corresponding to position 14 in motif sequence 1 can be serine or isoleucine.

In one embodiment, the amino acid residue in a position corresponding to position 29 in motif sequence 1 can be proline, alanine or lysine.

In one embodiment, the amino acid residue in a position corresponding to position 44 in motif sequence 1 can be histidine, arginine or tryptophan.

In one embodiment, the amino acid residue in a position corresponding to position 44 in motif sequence 1 can be arginine.

In one embodiment, the amino acid residue in a position corresponding to position 7 in motif sequence 2 can be leucine or isoleucine.

In one embodiment, the amino acid residue in a position corresponding to position 19 in motif sequence 2 can be methionine, cysteine, phenylalanine, isoleucine, valine or tyrosine.

In one embodiment, the amino acid residue in a position corresponding to position 19 in motif sequence 2 can be valine or tyrosine.

In one embodiment, the amino acid residue in a position corresponding to position 23 in motif sequence 2 can be arginine, histidine, isoleucine, lysine or valine.

In one embodiment, the amino acid residue in a position corresponding to position 23 in motif sequence 2 can be histidine.

In one embodiment, the amino acid residue in a position corresponding to position 34 in motif sequence 2 can be serine or threonine.

In one embodiment, the amino acid residue in a position corresponding to position 34 in motif sequence 2 can be serine.

In one embodiment, the amino acid residue in a position corresponding to position 19 in motif sequence 3 can be glycine, cysteine, histidine, lysine, leucine, asparagine, proline, glutamine, arginine or serine.

In one embodiment, the amino acid residue in a position corresponding to position 19 in motif sequence 3 can be glycine.

In one embodiment, the enzyme activity of the sucrose phosphorylase having improved thermostability at 37° C., after heating the sucrose phosphorylase having improved thermostability in 20 mM Tris buffer (pH 7.0) at 57° C. for 20 minutes, can be 10% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) at 57° C. for 20 minutes, can be 20% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes can be 10% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes, can be 20% or more of the enzyme activity of the sucrose phosphorylase having improved thermostability at 37° C. before heating.

In one embodiment, the sucrose phosphorylase having improved thermostability of the present invention can have an amino acid residue which is different from that of the natural sucrose phosphorylase in at least a position corresponding to position 14 in motif sequence 1.

In one embodiment, the sucrose phosphorylase having improved thermostability of the present invention can have an amino acid residue which is different from that of the natural sucrose phosphorylase in at least a position corresponding to position 19 in motif sequence 3.

One method of the present invention is a method for producing a sucrose phosphorylase having improved thermostability comprising:

modifying a first nucleic acid molecule comprising a base sequence encoding a first sucrose phosphorylase to obtain a second nucleic acid molecule comprising a modified base sequence;

preparing an expression vector comprising the second nucleic acid molecule;

introducing the expression vector into a cell to express a sucrose phosphorylase having improved thermostability; and recovering the expressed sucrose phosphorylase having improved thermostability, wherein the sucrose phosphorylase having improved thermostability has an amino acid residue which is different from the amino acid residue of the first sucrose phosphorylase in at least one position selected from the group consisting of:

a position corresponding to position 14, a position corresponding to position 29 and a position corresponding to position 44 in motif sequence 1: AVGGVHLLPFFPSTGDRG-FAPIDYHEVDSAFGDWDDVKRLGEKYYLMFDFMINHIS (SEQ ID NO. 25);

a position corresponding to position 7, a position corresponding to position 19, a position corresponding to position 23 and a position corresponding to position 34 in motif sequence 2: RPTQEDVDLIYKRKDRAPKQEIQFADGS-VEHLWNTFGEEQID (SEQ ID NO. 26); and a position corresponding to position 19 in motif sequence 3: ILPEIHEHYTIQFKIADHDYYVYDFALPMVTLYSLYSG (SEQ ID NO. 27); and wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating.

In one embodiment, the amino acid sequence of the first sucrose phosphorylase can have at least 40% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can have at least 60% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can be encoded by a nucleic acid molecule hybridizing under stringent conditions with a nucleic acid molecule consisting of a base sequence encoding an amino acid sequence selected from the group consisting of SEQ ID NO: 2, SEQ ID NO: 4, SEQ ID NO: 6, SEQ ID NO:

8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the first sucrose phosphorylase can be derived from a bacterium selected from the group consisting of *Streptococcus mutans, Streptococcus pneumoniae, Streptococcus sorbinus, Streptococcus mitis, Leuconostoc mesenteroides, Oenococcus oeni, Lactobacillus acidophilus* and *Listeria monocytogenes.*

In one embodiment, the first sucrose phosphorylase can be derived from *Streptococcus mutans, Streptococcus pneumoniae, Streptococcus sorbinus* or *Streptococcus mitis.*

In one embodiment, the natural sucrose phosphorylase can be derived from *Streptococcus mutans* or *Leuconostoc mesenteroides.*

In one embodiment, the enzyme activity of the sucrose phosphorylase having improved thermostability at 37° C., after heating the sucrose phosphorylase having improved thermostability in 20 mM Tris buffer (pH 7.0) at 57° C. for 20 minutes can be 10% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) at 57° C. for 20 minutes, can be 20% or more of the enzyme activity of the sucrose phosphorylase having improved thermostability at 37° C. before heating.

In one embodiment, the sucrose phosphorylase having improved thermostability can have an amino acid residue which is different from that of the first sucrose phosphorylase in at least a position corresponding to position 14 in motif sequence 1.

In one embodiment, the sucrose phosphorylase having improved thermostability can have an amino acid residue which is different from that of the first sucrose phosphorylase in at least a position corresponding to position 19 in motif sequence 3.

The nucleic acid molecules of the present invention comprise a base sequence encoding a sucrose phosphorylase having improved thermostability.

The vectors of the present invention comprise the nucleic acid molecule.

The cells of the present invention comprise the nucleic acid molecule.

One method of the present invention is a method of synthesizing glucose-1-phosphate, comprising reacting a reaction solution containing the sucrose phosphorylase having improved thermostability according to claim 1, sucrose and inorganic phosphoric acid to produce glucose-1-phosphate.

In one embodiment, the reaction can be carried out at a temperature of 50° C. to 70° C.

One method of the present invention is a method of synthesizing a glucose polymer, comprising reacting a reaction solution comprising: the sucrose phosphorylase having improved thermostability according to claim 1; a second phosphorylase using α-glucose-1-phosphate as a substrate; sucrose; a primer; and inorganic phosphoric acid or glucose-1-phosphate to produce a glucose polymer.

In one embodiment, the glucose polymer can be an α-glucan.

In one embodiment, the second phosphorylase can be an α-glucan phosphorylase.

In one embodiment, the second phosphorylase can be selected from the group consisting of cellobiose phosphorylase, cellodextrin phosphorylase, laminaribiose phosphorylase, laminaridextrin phosphorylase, β-1,3-glucan phosphorylase and trehalose phosphorylase.

In one embodiment, the reaction can be carried out at a temperature of 50° C. to 70° C.

The sucrose phosphorylase having improved thermostability of the present invention is a sucrose phosphorylase having improved thermostability obtained by modifying a natural sucrose phosphorylase, wherein the sucrose phosphorylase having improved thermostability has an amino acid residue which is different from that of the natural sucrose phosphorylase in at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249), in the amino acid sequence of SEQ ID NO: 2, and wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating.

In one embodiment, the amino acid sequence of the natural sucrose phosphorylase can have at least 40% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the natural sucrose phosphorylase can have at least 60% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the natural sucrose phosphorylase can be encoded by a nucleic acid molecule hybridizing under stringent conditions with a nucleic acid molecule consisting of a base sequence encoding an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the base sequence can be selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17 and SEQ ID NO: 19.

In one embodiment, the amino acid sequence of the natural sucrose phosphorylase can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the natural sucrose phosphorylase can be derived from a bacterium selected from the group consisting of *Streptococcus mutans, Streptococcus pneumoniae,*

*Streptococcus sorbinus, Streptococcus mitis, Leuconostoc mesenteroides, Oenococcus oeni, Lactobacillus acidophilus* and *Listeria monocytogenes*.

In one embodiment, the natural sucrose phosphorylase can be derived from a bacterium selected from the group consisting of *Streptococcus mutans, Streptococcus pneumoniae, Streptococcus sorbinus* and *Streptococcus mitis*.

In one embodiment, the natural sucrose phosphorylase can be derived from *Streptococcus mutans* or *Leuconostoc mesenteroides*.

In one embodiment, the amino acid residue in a position corresponding to T47 can be serine or isoleucine.

In one embodiment, the amino acid residue in a position corresponding to S62 can be proline, alanine or lysine.

In one embodiment, the amino acid residue in a position corresponding to Y77 can be histidine, arginine or tryptophan.

In one embodiment, the amino acid residue in a position corresponding to Y77 can be arginine.

In one embodiment, the amino acid residue in a position corresponding to V128 can be leucine or isoleucine.

In one embodiment, the amino acid residue in a position corresponding to K140 can be methionine, cysteine, phenylalanine, isoleucine, valine or tyrosine.

In one embodiment, the amino acid residue in a position corresponding to K140 can be valine or tyrosine.

In one embodiment, the amino acid residue in a position corresponding to Q144 can be arginine, histidine, isoleucine, lysine or valine.

In one embodiment, the amino acid residue in a position corresponding to Q144 can be histidine.

In one embodiment, the amino acid residue in a position corresponding to N155 can be serine or threonine.

In one embodiment, the amino acid residue in a position corresponding to N155 can be serine.

In one embodiment, the amino acid residue in a position corresponding to D249 can be glycine, cysteine, histidine, lysine, leucine, asparagine, proline, glutamine, arginine or serine.

In one embodiment, the amino acid residue in a position corresponding to D249 can be glycine.

In one embodiment, the enzyme activity of the sucrose phosphorylase having improved thermostability of the present invention at 37° C., after heating the sucrose phosphorylase having improved thermostability in 20 mM Tris buffer (pH 7.0) at 57° C. for 20 minutes can be 10% or more of the enzyme activity of the sucrose phosphorylase having improved thermostability at 37° C. before heating.

In one embodiment, the enzyme activity of the sucrose phosphorylase having improved thermostability of the present invention at 37° C., after heating the sucrose phosphorylase having improved thermostability in 20 mM Tris buffer (pH 7.0) at 57° C. for 20 minutes, is 20% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes can be 10% or more of the enzyme activity of the sucrose phosphorylase having improved thermostability at 37° C. before heating.

In one embodiment, the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes, is 20% or more of enzyme activity of the sucrose phosphorylase having improved thermostability at 37° C. before heating.

In one embodiment, the sucrose phosphorylase having improved thermostability of the present invention has an amino acid residue which is different from that of the natural sucrose phosphorylase in at least a position corresponding to T47.

In one embodiment, the sucrose phosphorylase having improved thermostability of the present invention has an amino acid residue which is different from that of the natural sucrose phosphorylase in at least a position corresponding to T47.

In one embodiment, the sucrose phosphorylase having improved thermostability of the present invention has an amino acid residue which is different from that of the natural sucrose phosphorylase in at least a position corresponding to D249.

The method of the present invention is a method for producing sucrose phosphorylase having improved thermostability, comprising modifying a first nucleic acid molecule comprising a base sequence encoding a first sucrose phosphorylase to obtain a second nucleic acid molecule comprising a modified base sequence; preparing an expression vector containing the second nucleic acid molecule; introducing the expression vector into a cell to express a sucrose phosphorylase having improved thermostability; and recovering the expressed sucrose phosphorylase having improved thermostability, wherein the sucrose phosphorylase having improved thermostability has an amino acid residue which is different from the amino acid residue of the first sucrose phosphorylase in at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) in the amino acid sequence of SEQ ID NO: 2, and wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating.

In one embodiment, the amino acid sequence of the first sucrose phosphorylase can have at least 40% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can have at least 60% identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can be encoded by a nucleic acid molecule hybridizing under stringent conditions with a nucleic acid molecule consisting of a base sequence encoding an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the amino acid sequence of the first sucrose phosphorylase can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20.

In one embodiment, the first sucrose phosphorylase can be derived from a bacterium selected from the group consisting of *Streptococcus mutans, Streptococcus pneumoniae, Streptococcus sorbinus, Streptococcus mitis, Leuconostoc mesenteroides, Oenococcus oeni, Lactobacillus acidophilus* and *Listeria monocytogenes*.

In one embodiment, the first sucrose phosphorylase can be derived from a bacterium selected from the group consisting of *Streptococcus mutans, Streptococcus pneumoniae, Streptococcus sorbinus* or *Streptococcus mitis*.

In one embodiment, the first sucrose phosphorylase can be derived from *Streptococcus mutans* or *Leuconostoc mesenteroides*.

In one embodiment, the enzyme activity of the sucrose phosphorylase having improved thermostability at 37° C., after heating the sucrose phosphorylase having improved thermostability in 20 mM Tris buffer (pH 7.0) at 57° C. for 20 minutes can be 10% or more of the enzyme activity of the sucrose phosphorylase having improved thermostability at 37° C. before heating.

In one embodiment, the enzyme activity of the sucrose phosphorylase having improved thermostability at 37° C. after heating the sucrose phosphorylase having improved thermostability in 20 mM Tris buffer (pH 7.0) at 57° C. for 20 minutes, is 20% or more of the enzyme activity of the sucrose phosphorylase having improved thermostability at 37° C. before heating.

In one embodiment, the sucrose phosphorylase having improved thermostability of the present invention can have an amino acid residue which is different from that of the first sucrose phosphorylase in at least a position corresponding to T47.

In one embodiment, the sucrose phosphorylase having improved thermostability of the present invention can have an amino acid residue which is different from that of the first sucrose phosphorylase in at least a position corresponding to D249.

The nucleic acid molecules of the present invention comprise a base sequence encoding the sucrose phosphorylase having improved thermostability.

The vectors of the present invention comprise the nucleic acid molecule.

The cells of the present invention contains the nucleic acid molecule.

The method of synthesizing glucose-1-phosphate according to the present invention comprises reacting a reaction solution containing the sucrose phosphorylase having improved thermostability, sucrose and inorganic phosphoric acid to produce glucose-1-phosphate.

In one embodiment, the above reaction can be carried out at a temperature of 50° C. to 70° C.

The method of synthesizing a glucose polymer according to the present invention comprises reacting a reaction solution containing: the sucrose phosphorylase having improved thermostability; a second phosphorylase using α-glucose-1-phosphate as a substrate; sucrose; a primer; and inorganic phosphoric acid or glucose-1-phosphate to produce a glucose polymer.

In one embodiment, the glucose polymer can be α-glucan.

In one embodiment, the second phosphorylase can be α-glucan phosphorylase.

In one embodiment, the second phosphorylase can be selected from the group consisting of cellobiose phosphorylase, cellodextrin phosphorylase, laminaribiose phosphorylase, laminaridextrin phosphorylase, β-1,3-glucan phosphorylase and trehalose phosphorylase.

In one embodiment, the above reaction can be carried out at a temperature of 50° C. to 70° C.

EFFECT OF THE INVENTION

According to the present invention, an SP enzyme capable of reaction at high temperatures (for example 60° C. or more) and having a very high activity at high temperatures (for example 60° C. or more) was obtained. By this improvement of thermostability, efficient production of G-1-P or an α-glucan was made possible by suppressing microbial contamination and α-glucan aging.

The claimed invention attains the advantage that, when a gene encoding the sucrose phosphorylase having improved thermostability of the present invention (e.g. a gene encoding SP having improved thermostability, obtained by improving thermostability of *Streptococcus mutans*-derived GP) is highly expressed in mesophilic bacterium host, such as *Escherichia coli*, contaminating enzymes derived from the host bacterium can be simply removed by heating the bacterial cell extract containing an enzyme having improved thermostability at 60° C. Therefore, the method of the present invention is advantageous in terms of enzyme purification.

The method of the present invention is effective not only in SP derived from *Streptococcus mutans* and SP derived from *Leuconostoc mesenteroides* but can also be suitably applied to improving the thermostability of other SPs exhibiting high homology to the amino acid structure of SP derived from *Streptococcus mutans*.

Therefore, other organism-derived sucrose phosphorylases having improved thermostability which have an amino acid residue which is different from the amino acid residue of the natural sucrose phosphorylase in at least one position selected from the group consisting of a position corresponding to position 14, a position corresponding to position 29 and a position corresponding to position 44 in motif sequence 1: AVGGVHLLPFFPSTGDRGFAPIDYHEVD-SAFGDWDDVKRLGEKYYLMFDFMINHI S; a position corresponding to position 7, a position corresponding to position 19, a position corresponding to position 23 and a position corresponding to position 34 in motif sequence 2: RPTQED-VDLIYKRKDRAPKQEIQFADGSVEHLWNTFGEEQID; and a position corresponding to position 19 in motif sequence 3: ILPEIHEHYTIQFKIADHDYYVYDFALP-MVTLYSLYSG.

Other organism-derived SPs having improved thermostability can be obtained, which have an amino acid residue which is different from the amino acid residue of the natural sucrose phosphorylase, in at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249).

BRIEF DESCRIPTION OF THE DRAWINGS

Figure 1A:
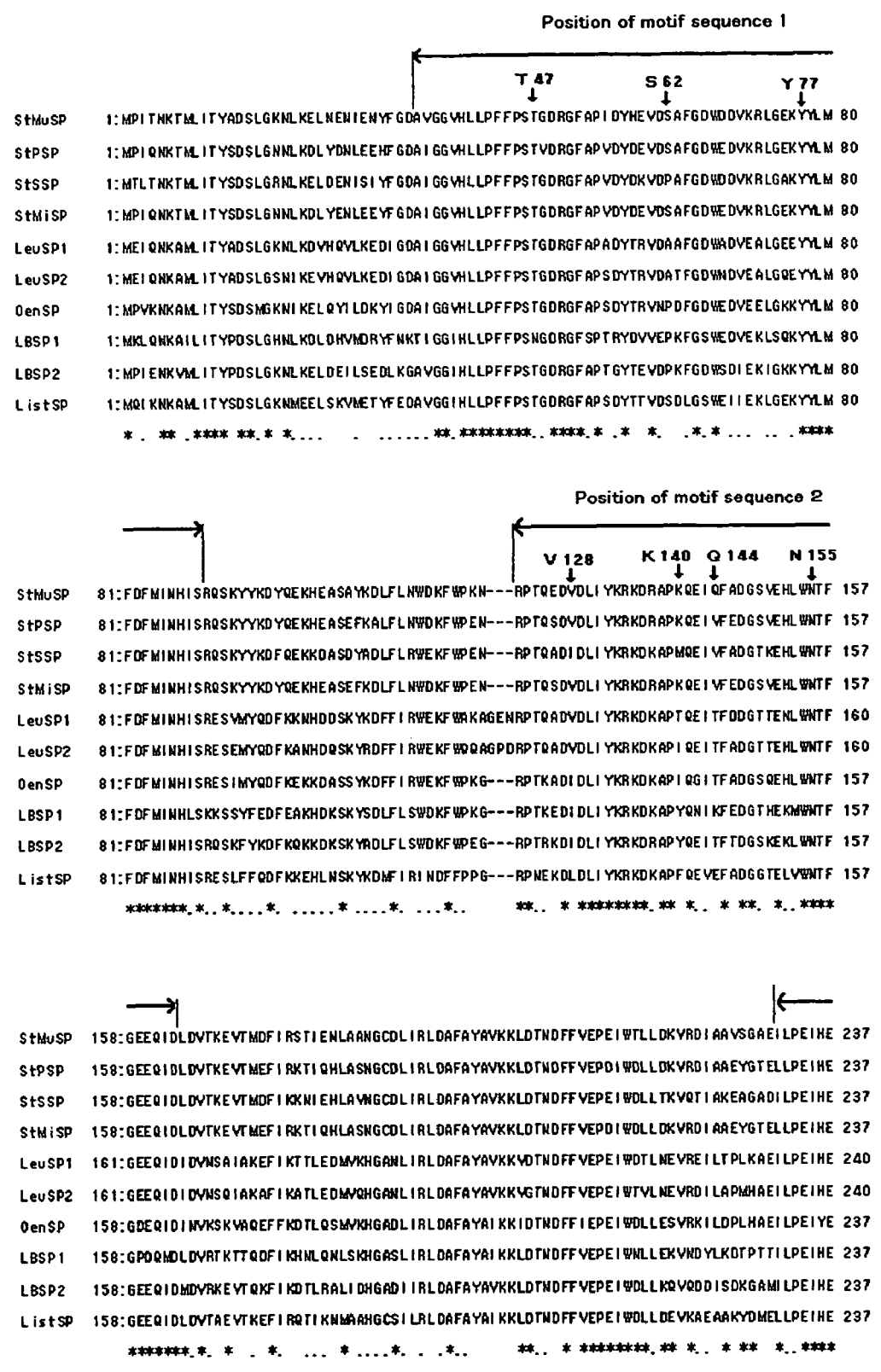

FIG. 1A: FIG. 1A is a view showing amino acid sequences of sucrose phosphorylases derived from some organisms, which are aligned in multiple alignment by GENETYX-WIN Ver. 4.0. The sucrose phosphorylases are StMuSP (SEQ ID NO. 2); StPSP (SEQ ID NO. 4); StSSP (SEQ ID NO. 6); StMiSP (SEQ ID NO. 12); LeuSP1 (SEQ ID NO. 8); LeuSP2 (SEQ ID NO. 14); OenSP (SEQ ID NO. 10); LBSP1 (SEQ ID NO. 16); LBSP2 (SEQ ID NO. 18); and ListSP (SEQ ID NO. 20). FIG. 1A is followed by FIG. 1B.

FIG. 1B: FIG. 1B is a continuation view from FIG. 1A.

FIG. 1C is a continuation view from FIG. 1B.

FIG. 2 is a graph showing the remaining activity (%) of phosphatase after various bacteria (*Escherichia coli* TG-1 and *Escherichia coli* BL21) were heated at 50° C., 55° C., 60° C. or 65° C. for 30 minutes.

FIG. 3 is a graph showing the remaining activity (%) of amylase after various bacteria (*Escherichia coli* TG-1, *Escherichia coli* BL21 and *Bacillus subtilis* ANA-1) were heated for 30 minutes at 50° C., 55° C., 60° C. or 65° C.

DESCRIPTION OF THE SEQUENCE LISTING

Figures 1C, 2:
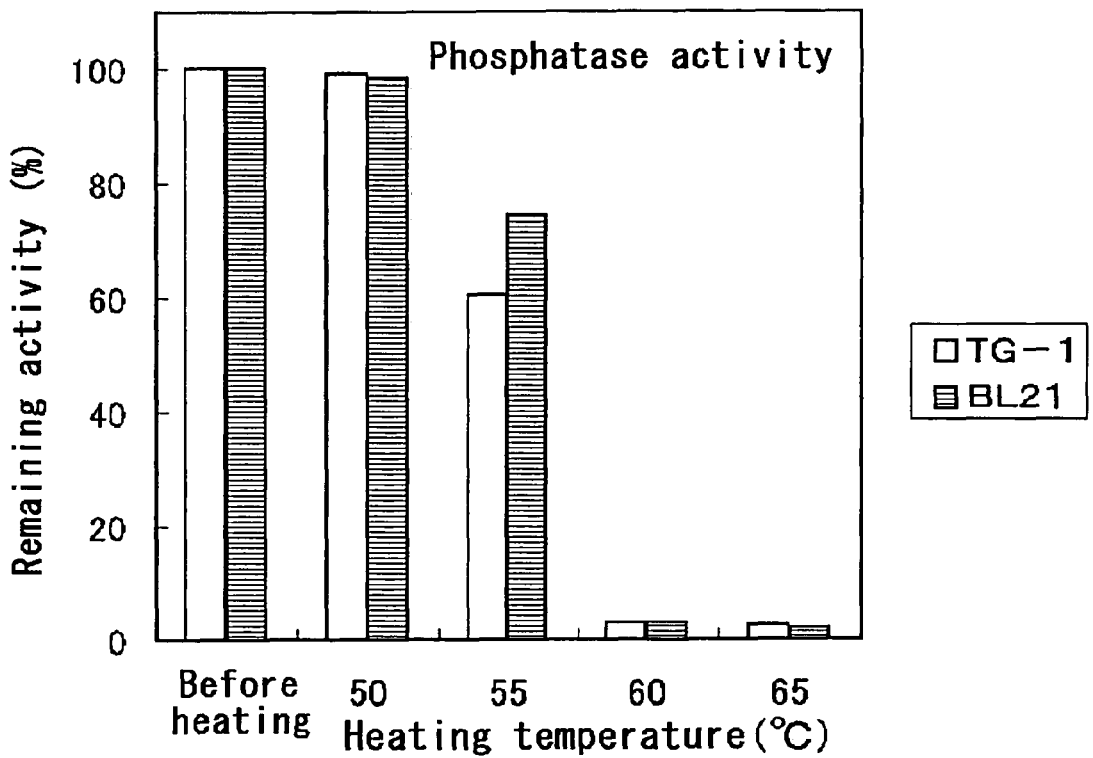
FIG. 1C.
FIG. 2.
Figure 3:
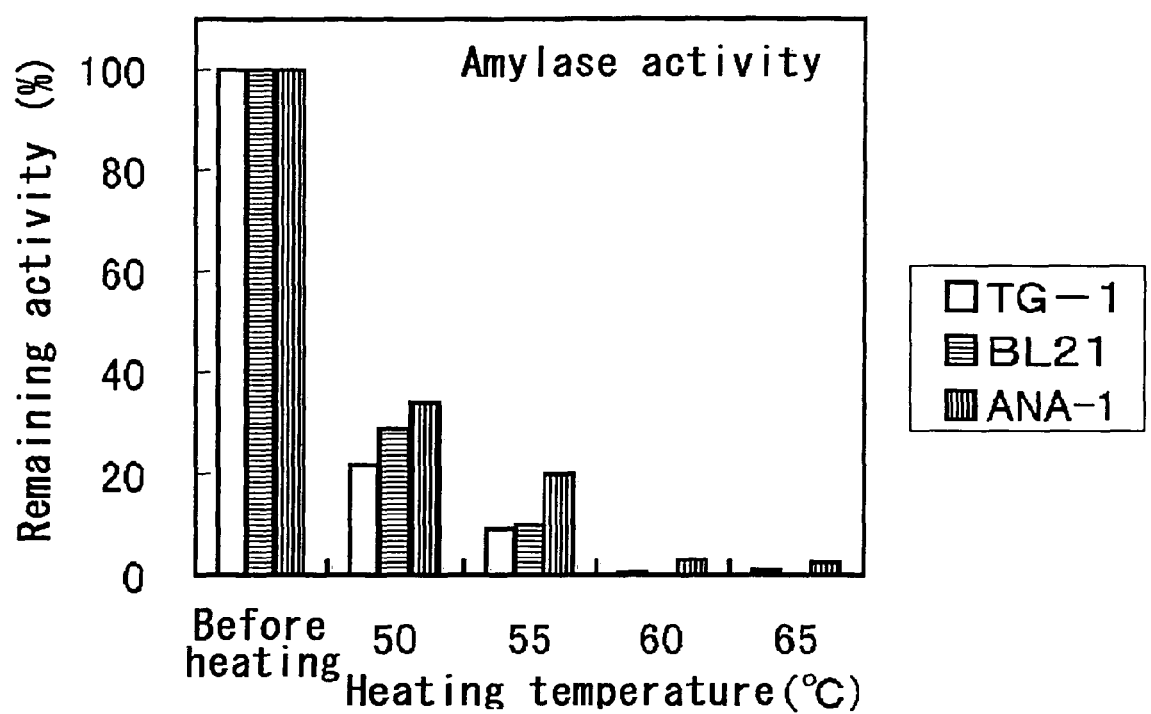
FIG. 3.

SEQ ID NO: 1: base sequence encoding sucrose phosphorylase from *Streptococcus mutans*;

SEQ ID NO: 2: amino acid sequence of sucrose phosphorylase from *Streptococcus mutans*;

SEQ ID NO: 3: base sequence encoding sucrose phosphorylase from *Streptococcus pneumoniae*;

SEQ ID NO: 4: amino acid sequence of sucrose phosphorylase from *Streptococcus pneumoniae*;

SEQ ID NO: 5: base sequence encoding sucrose phosphorylase from *Streptococcus sorbinus*;

SEQ ID NO: 6: amino acid sequence of sucrose phosphorylase from *Streptococcus sorbinus*;

SEQ ID NO: 7: base sequence encoding sucrose phosphorylase from *Leuconostoc mesenteroides*;

SEQ ID NO: 8: amino acid sequence of sucrose phosphorylase from *Leuconostoc mesenteroides*;

SEQ ID NO: 9: base sequence encoding sucrose phosphorylase from *Oenococcus oeni*;

SEQ ID NO: 10: amino acid sequence of sucrose phosphorylase from *Oenococcus oeni*;

SEQ ID NO: 11: base sequence encoding sucrose phosphorylase from *Streptococcus mitis*;

SEQ ID NO: 12: amino acid sequence of sucrose phosphorylase from *Streptococcus mitis*;

SEQ ID NO: 13: base sequence encoding second sucrose phosphorylase from *Leuconostoc mesenteroides*;

SEQ ID NO: 14: amino acid sequence of second sucrose phosphorylase from *Leuconostoc mesenteroides*;

SEQ ID NO: 15: base sequence encoding first sucrose phosphorylase from *Lactobacillus acidophilus*;

SEQ ID NO: 16: amino acid sequence of first sucrose phosphorylase from *Lactobacillus acidophilus*;

SEQ ID NO: 17: base sequence encoding second sucrose phosphorylase from *Lactobacillus acidophilus*;

SEQ ID NO: 18: amino acid sequence of second sucrose phosphorylase from *Lactobacillus acidophilus*;

SEQ ID NO: 19: base sequence encoding sucrose phosphorylase from *Listeria monocytogenes*;

SEQ ID NO: 20: amino acid sequence of sucrose phosphorylase from *Listeria monocytogenes*;

SEQ ID NO: 21: base sequence encoding sucrose phosphorylase having improved thermostability which has all 8 mutations (T47S, S62P, Y77H, V128L, K140M, Q144R, N155S and D249G), prepared in Example 2A (1); 1

SEQ ID NO: 22: amino acid sequence of sucrose phosphorylase having improved thermostability which has all 8 mutations (T47S, S62P, Y77H, V128L, K140M, Q144R, N155S and D249G), prepared in Example 2A (1);

SEQ ID NO: 23: base sequence encoding sucrose phosphorylase having amino acid substitutions and additions in the C terminal thereof, used in Example 7;

SEQ ID NO: 24: amino acid sequence of sucrose phosphorylase having amino acid substitutions and additions in the C terminal thereof, used in Example 7;

SEQ ID NO: 25: amino acid sequence of motif sequence 1;

SEQ ID NO: 26: amino acid sequence of motif sequence 2; and

SEQ ID NO: 27: amino acid sequence of motif sequence 3.

BEST MODE FOR CARRYING OUT THE INVENTION

The present invention will be explained below. It should be understood that throughout the present specification, terms used in the present specification are used so as to have the meanings normally used in the art, unless otherwise specifically indicated.

(1. Sucrose Phosphorylase)

In the present specification, "sucrose phosphorylase" and "SP" are exchangeably used unless otherwise specifically indicated, and means an enzyme having a sucrose phosphorylase activity. Sucrose phosphorylase is classified as EC. 2.4.1.7. The reaction catalyzed by sucrose phosphorylase is shown as follows:

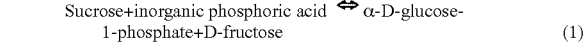

$$\text{Sucrose} + \text{inorganic phosphoric acid} \leftrightarrow \alpha\text{-D-glucose-1-phosphate} + \text{D-fructose} \quad (1)$$

Sucrose phosphorylase is contained in various organisms in nature. Examples of the organisms producing sucrose phosphorylase include bacteria belonging to the genus *Streptococcus* (for example, *Streptococcus mutans*, *Streptococcus pneumoniae*, *Streptococcus sorbinus*, *Streptococcus thermohilus* and *Streptococcus mitis*), *Leuconostoc mesenteroides*, *Oenococcus oeni*, *Lactobacillus acidophilus*, *Bifidobacterium* sp. (for example, *Bifidobacterium longum* and *Bifidobacterium adolescentis*), *Agrobacterium* sp. (for example, *Agrobacterium vitis*), *Pseudomonas* sp. (for example, *Pseudomonas saccharophila*), *Escherichia coli*, *Listeria* sp. (for example, *Listeria innocua* and *Listeria monocytogenes*), *Clostridium* sp., *Pullularia pullulans*, *Acetobacter xylinum*, *Synecococcus* sp., *Aspergillus niger*, *Sclerotinea escerotiorum*, and *Chlamydomonas* sp. Organisms producing sucrose phosphorylase are not limited to the above.

A first (for example, natural) sucrose phosphorylase used in the method according to the present invention is preferably derived from bacteria, and is more preferably derived from mesophiles. However, these sucrose phosphorylases are not thermostable. Accordingly, these sucrose phosphorylases cannot catalyze the reaction sufficiently at high temperatures (for example, at about 50° C. to 60° C. or more). Therefore, when the reaction is carried out at about 30° C. to about 40° C., adjusted to the optimum reaction temperature of the bacteria-derived SP, there arises a problem of bacterial enzyme contamination or a problem of α-glucan aging, and thus α-glucan or G-1-P cannot be efficiently produced.

In the present specification, an enzyme "derived from" an organism, means not only that the enzyme is directly isolated from the organism, but also refers to an enzyme obtained by utilizing the organism in any form. For example, when a gene encoding an enzyme obtained from an organism is introduced into *Escherichia coli*, and the expressed enzyme is subsequently isolated from the *Escherichia coli*, the enzyme is referred to as being "derived from" the organism.

The base sequence encoding natural sucrose phosphorylase from *Streptococcus mutans* is set forth in SEQ ID NO: 1, and the amino acid sequence encoded thereby is set forth in SEQ ID NO: 2. In *Streptococcus mutans*, a natural sucrose phosphorylase having an amino acid sequence different from SEQ ID NO: 2 is also known. In both the SP having the amino acid sequence of SEQ ID NO: 2 and the other SP derived from *S. mutans*, the amino acid at position 47 is threonine, the amino acid at position 62 is serine, the amino acid at position 77 is tyrosine, the amino acid at position 128 is valine, the amino acid at position 140 is lysine, the amino acid at position 144 is glutamine, and the amino acid at position 155 is asparagine, so both of these sucrose phosphorylases are almost equivalent in thermostability. In the present specification, "natural" sucrose phosphorylase encompasses not only sucrose phosphorylase isolated from a bacterium originally producing sucrose phosphorylase but also sucrose phosphorylase obtained by genetic recombination, which has the same amino acid sequence as that of the natural sucrose phosphorylase.

The base sequence encoding the natural sucrose phosphorylase of *Streptococcus pneumoniae* is set forth in SEQ ID NO: 3, and the amino acid sequence encoded thereby is set forth in SEQ ID NO: 4.

The base sequence encoding the natural sucrose phosphorylase of *Streptococcus sorbinus* is set forth in SEQ ID NO: 5, and the amino acid sequence encoded thereby is set forth in SEQ ID NO: 6.

The base sequence encoding the natural sucrose phosphorylase of *Leuconostoc mesenteroides* is set forth in SEQ ID NO: 7, and the amino acid sequence encoded thereby is set forth in SEQ ID NO: 8.

The base sequence encoding the natural sucrose phosphorylase of *Oenococcus oeni* is set forth in SEQ ID NO: 9, and the amino acid sequence encoded thereby is set forth in SEQ ID NO: 10.

The base sequence encoding the natural sucrose phosphorylase of *Streptococcus mitis* is set forth in SEQ ID NO: 11, and the amino acid sequence encoded thereby is set forth in SEQ ID NO: 12.

The base sequence encoding the second natural sucrose phosphorylase of *Leuconostoc mesenteroides* is set forth in SEQ ID NO: 13, and the amino acid sequence encoded thereby is set forth in SEQ ID NO: 14.

The base sequence encoding the first natural sucrose phosphorylase of *Lactobacillus acidophilus* is set forth in SEQ ID NO: 15, and the amino acid sequence encoded thereby is set forth in SEQ ID NO: 16.

The base sequence encoding the second natural sucrose phosphorylase of *Lactobacillus acidophilus* is set forth in SEQ ID NO: 17, and the amino acid sequence encoded thereby is set forth in SEQ ID NO: 18.

The base sequence encoding the natural sucrose phosphorylase of *Listeria monocytogenes* is set forth in SEQ ID NO: 19, and the amino acid sequence encoded thereby is set forth in SEQ ID NO: 20.

The base sequences and amino acid sequences of these natural sucrose phosphorylases are illustrative, and it is known that variants (so called, allele variants) having slightly different sequences from these sequences can naturally occur. In the present invention, such natural variants, in addition to the sucrose phosphorylases having these exemplary sequences, are usable in the improvement of thermostability.

The first (for example, natural) sucrose phosphorylase used in the method according to the present invention is preferably derived from *Streptococcus mutans, Streptococcus pneumoniae, Streptococcus sorbinus, Streptococcus mitis, Leuconostoc mesenteroides, Oenococcus oeni, Lactobacillus acidophilus* and *Listeria monocytogenes*, more preferably *Streptococcus mutans, Streptococcus pneumoniae, Streptococcus sorbinus,* or *Streptococcus mitis*. The natural sucrose phosphorylase is most preferably derived from *Streptococcus mutans* or *Leuconostoc mesenteroides*.

A gene of sucrose phosphorylase can be obtained by designing a primer in reference to the known sucrose phosphorylase sequence and conducting a PCR using a genome library from which the sucrose phosphorylase gene is to be obtained as a template. Alternatively, a SP gene can be also prepared directly by chemical synthesis, based on the known SP gene sequence information, without preparation of a genomic library. A method of synthesizing a gene is described in, for example, Te'o, et al. (FEMS Microbiological Letters, Vol. 190, pp. 13-19, 2000), and the like.

The resulting SP gene can be inserted into a suitable vector by methods well-known to those skilled in the art. For example, as a vector for *Escherichia coli*, pMW118 (manufactured by Nippon Gene Co., Ltd.), pUC18 (manufactured by Takara Bio Inc.), pKK233-2 (manufactured by Amersham-Pharmacia-Biotech) and the like, can be used and, as a vector for *Bacillus subtilis*, pUB110 (which can be purchased from American Type Culture Collection), pHY300PLK (manufactured by Takara Bio Inc.) and the like, can be used.

(2. Improving the Thermostability of Sucrose Phosphorylase)

A method according to the present invention includes modifying a first nucleic acid molecule comprising a base sequence encoding a first sucrose phosphorylase to obtain a second nucleic acid molecule containing a modified base sequence; preparing an expression vector comprising the second nucleic acid molecule; introducing the expression vector into a cell, to express an sucrose phosphorylase having improved thermostability; and recovering the expressed sucrose phosphorylase having improved thermostability.

(2.1 Isolation of Nucleic Acid Molecule Comprising Base Sequence Encoding First (for Example, Natural) Sucrose Phosphorylase)

A nucleic acid molecule comprising a base sequence encoding sucrose phosphorylase having improved thermostability according to the present invention is also within the scope of the present invention. Such a nucleic acid molecule can be obtained by using methods known in the art, based on the disclosure of the present specification.

A nucleic acid molecule comprising a base sequence encoding a natural sucrose phosphorylase can be isolated directly from an above-described naturally occurring bacterium producing the natural sucrose phosphorylase.

For example, firstly, natural sucrose phosphorylase is isolated from *Streptococcus mutans* or the like. To exemplify a procedure for *Streptococcus mutans*-derived sucrose phosphorylase, firstly, *Streptococcus mutans* is inoculated into a suitable medium (for example, LB medium) and then cultured at 37° C. overnight with shaking. Then, this culture is centrifuged to collect the *Streptococcus mutans* cells. The resulting cell pellet is suspended in 20 mM Tris-HCl buffer (pH 7.0) and then disrupted by sonication to result in a liquid containing disrupted cells. Then, sucrose is added to this liquid containing disrupted cells to a final concentration of 10% sucrose. This liquid containing disrupted cells is heated in a water bath at 55° C. for 30 minutes. After heating, this liquid containing disrupted cells is centrifuged by a centrifuge (AVANTI J-25I manufactured by BECKMANN) to remove insoluble proteins, and thus obtaining a supernatant. The resulting supernatant is passed through previously equilibrated anion-exchange resin Q-Sepharose to allow sucrose phosphorylase to be adsorbed onto the resin. The resin is washed with a buffer containing 100 mM sodium chloride to remove impurities. Then, the sucrose phosphorylase is eluted with a buffer containing 300 mM sodium chloride, to give a *Streptococcus mutans*-derived sucrose phosphorylase enzyme solution.

Usually, at this stage, this solution can serve as a sucrose phosphorylase-containing solution usable for trypsin treatment, but may sometimes require further purification. In this case, a purified *Streptococcus mutans*-derived sucrose phosphorylase-containing solution can be obtained by combining fractionation with gel filtration chromatography on Sephacryl S-200HR (manufactured by Pharmacia) or the like with fractionation with hydrophobic chromatography on Phenyl-TOYOPEARL 650M (manufactured by Tosoh Corporation) or the like, if necessary. Purification of sucrose phosphorylase derived from other bacterial species can also be carried out in the same manner.

The thus obtained purified sucrose phosphorylase is treated with trypsin, the resulting trypsin-treated fragment is separated by HPLC, and the amino acid sequence of the N-terminus of any of the separated peptide fragments is determined using a peptide sequencer. Then, using synthetic oligonucleotide probes prepared based on the identified amino acid sequence, a suitable genome library or a cDNA library is screened, thereby, a nucleic acid molecule (also referred to as a gene) comprising a base sequence encoding natural sucrose phosphorylase can be obtained. Fundamental strategies for preparing oligonucleotide probes and a DNA library, and screening them by hybridization of nucleic acids, are well-known to those skilled in the art. For example, see Sambrook, et al., Molecular Cloning: A Laboratory Manual (1989); DNA Cloning, vol. I and II (edited by D. N. Glover, 1985); Oligonucleotide Synthesis (edited by M. J. Gait, 1984); Nucleic Acid Hybridization (edited by B. D. Hames & S. J. Higgins, 1984).

Alternatively, based on homology to a base sequence of certain sucrose phosphorylases for which a base sequence encoding sucrose phosphorylase is known, screening can be conducted by hybridization using nucleic acid probes containing at least a part of this base sequence, thereby, a nucleic acid molecule containing the base sequence of another kind of sucrose phosphorylase may be acquired. Such methods are known in the art.

Alternatively, degenerate primers corresponding to a region which is conserved in the amino acid sequence of various sucrose phosphorylases are prepared, and PCR is performed, a base sequence of the sucrose phosphorylase may be acquired. Such methods are known in the art.

When a genome library is screened, the resulting nucleic acid molecule can be subcloned using methods well-known to those skilled in the art. For example, by mixing λ phage containing an objective gene, suitable *Escherichia coli* and suitable helper phage, a plasmid containing an objective gene can be easily obtained. Thereafter, by transforming suitable *Escherichia coli* using a solution containing the plasmid, an objective gene can be subcloned. By culturing the resulting transformants, a plasmid DNA may be obtained, for example, by an alkaline SDS method, and the base sequence of the objective gene can be determined. A method of determining a base sequence is well-known to those skilled in the art. Further, by using primers synthesized based on a base sequence of a DNA fragment, and using a polymerase chain reaction (PCR) employing, for example, the genomic DNA of *Streptococcus mutans, Streptococcus pneumoniae, Streptococcus sorbinus* or the like as a template, a sucrose phosphorylase gene may be directly amplified.

In the present specification, the "nucleic acid molecule" may consist only of natural nucleotides, may contain non-natural nucleotides, or may consist of only non-natural nucleotides. Examples of a non-natural nucleotide include derivatized nucleotides (also refers to as nucleotide analogs). The "derivatized nucleotide" and the "nucleotide analog" refer to those nucleotides which are different from naturally occurring nucleotides, but have a similar function to that of the original nucleotide. Such derivatized nucleotides and nucleotide analogs are well-known in the art. Examples of such derivatized nucleotides and nucleotide analogs include, but are not limited to phosphorothioate, phosphoramidate, methylphosphonate, chiral methylphosphonate, 2-O-methylribonucleotide, and peptide-nucleic acid (PNA).

(2.2 Modification of the First Nucleic Acid Molecule Comprising a Base Sequence Encoding First Sucrose Phosphorylase)

A first nucleic acid molecule comprising a base sequence encoding a first sucrose phosphorylase is modified to obtain a second nucleic acid molecule containing a modified base sequence. A first nucleic acid molecule can be a nucleic acid molecule having a base sequence encoding a natural sucrose phosphorylase, obtained as in the above (2.1). The first nucleic acid molecule may also be a nucleic acid molecule comprising a base sequence encoding sucrose phosphorylase which has substantially the same enzyme activity as the enzyme activity of the natural sucrose phosphorylase, and in which 1 or a few or more amino acids are substituted, deleted or added to the amino acid sequence of natural sucrose phosphorylase. The base sequence of SEQ ID NO: 23 is set force as an example of such a base sequence encoding a sucrose phosphorylase having substitutions and additions of amino acids to the amino acid sequence of a natural sucrose phosphorylase. In this base sequence, 4 bases in the 3'-terminal thereof are substituted, and 18 bases are added to the 3'-terminal, with respect to the natural base sequence (that is, the base sequence of SEQ ID NO: 1). In the amino acid sequence (amino acid sequence of SEQ ID NO: 24) encoded by this base sequence, 2 amino acids in the C-terminal thereof are substituted and 6 amino acids are added to the C-terminal respective to the natural amino acid sequence (that is, the amino acid sequence of SEQ ID NO: 2), but the enzyme activity of this enzyme is substantially the same as that of the natural sucrose phosphorylase. The "has substantially the same enzyme activity" refers to the enzyme activity when sucrose phosphorylase having a substitution, deletion or addition to the amino acid sequence of a natural sucrose phosphorylase measured under the same conditions as that of the natural sucrose phosphorylase is within ±20%, preferably within ±10%, more preferably within ±5% of enzyme activity of the natural sucrose phosphorylase Modification can be performed using a well-known method, such as by carrying out site-directed mutagenesis, mutagenesis using a mutagen (treatment of a subject gene with a mutagenic agent such as nitrite, ultraviolet-ray treatment), or error prone PCR. It is preferable to use site-directed mutagenesis from the viewpoint that the objective mutation is easily obtained, because the objective modification can be introduced at an object site when site-directed mutagenesis is used. Alternatively, a nucleic acid molecule having an objective sequence may be directly synthesized. Such chemical synthesis methods are well-known in the art.

The present inventors found out that, by substituting an amino acid residue at a particular position in the amino acid sequence of a sucrose phosphorylase, with another amino acid residue, the thermostability of the resulting modified sucrose phosphorylase is improved. Such a particular position can be determined by aligning any of the following motif sequences, or the amino acid sequence of SEQ ID NO: 2, and a comparison subject amino acid sequence:
motif Sequence 1: AVGGVHLLPFFPSTGDRGFAPIDY-HEVDSAFGDWDDVKRLGEKYYLMFDFMINHI S (SEQ ID NO: 25);
motif Sequence 2: RPTQEDVDLIYKRKDRAPKQEIQ-FADGSVEHLWNTFGEEQID (SEQ ID NO: 26); and
motif Sequence 3: ILPEIHEHYTIQFKIADHDYYVYD-FALPMVTLYSLYSG (SEQ ID NO: 27).

Motif sequences 1, 2 and 3 are present in the amino acid sequence (SEQ ID NO: 2) of *Streptococcus mutans*-derived sucrose phosphorylase. These motif sequences are present in the following positions in the *Streptococcus mutans*-derived sucrose phosphorylase: motif sequence 1: position 34 to position 89 of the amino acid sequence set forth in SEQ ID NO: 2; motif sequence 2: position 122 to position 163 of the amino acid sequence set forth in SEQ ID NO: 2; motif sequence 3: position 231 to position 268 of the amino acid sequence set forth in SEQ ID NO: 2. Generally, natural sucrose phosphorylase has these motif sequences, or sequences having high homology to them. The position of these motif sequences in other sucrose phosphorylases can be easily determined by those skilled in the art.

In the method according to the present invention, a nucleic acid molecule comprising a base sequence encoding a first sucrose phosphorylase is modified so that sucrose phosphorylase having improved thermostability, encoded by a modified nucleic acid molecule having an amino acid residue which is different from that of the natural sucrose phosphorylase in at least one position selected from the group consisting of: a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3. Alternatively, a nucleic acid molecule comprising a base sequence encoding a first sucrose phosphorylase is modified so that sucrose phosphorylase having improved thermostability, encoded by a modified nucleic acid molecule having an amino acid residue which is different from that of the natural sucrose phosphorylase in at least one position selected from the group consisting of: a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) in the amino acid sequence of SEQ ID NO:2). Preferably, a nucleic acid molecule comprising a base sequence encoding the first sucrose phosphorylase is modified so that sucrose phosphorylase having improved thermostability, encoded by a modified nucleic acid molecule is different from the natural sucrose phosphorylase in at least two positions, more preferably at least three positions, further preferably at least four positions, still more preferably at least five positions, still further preferably at least six positions, particularly preferably at least seven positions, and most preferably all eight positions, selected from the group consisting of: a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3 (or a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) in the amino acid sequence of SEQ ID NO: 2).

In one embodiment, a nucleic acid molecule comprising a base sequence encoding a first sucrose phosphorylase is modified so that sucrose phosphorylase having improved thermostability, encoded by a modified nucleic acid molecule is different from the natural sucrose phosphorylase in at least a position corresponding to position 14 in motif sequence 1 (or a position corresponding to threonine at position 47 (T47) in the amino acid sequence of SEQ ID NO: 2).

In one embodiment, a nucleic acid molecule comprising a base sequence encoding a first sucrose phosphorylase is modified so that the sucrose phosphorylase having improved thermostability encoded by a modified nucleic acid molecule is different from the natural sucrose phosphorylase in at least a position corresponding to position 19 in motif sequence 3 (or a position corresponding to aspartic acid in position 249 (D249) in the amino acid sequence of SEQ ID NO: 2).

In one embodiment, a nucleic acid molecule comprising a base sequence encoding a first sucrose phosphorylase is modified so that the sucrose phosphorylase having improved thermostability encoded by a modified nucleic acid molecule is different from the natural sucrose phosphorylase in at least a position corresponding to position 34 in motif sequence 2 (or a position corresponding to asparagine in position 155 (N155) in the amino acid sequence of SEQ ID NO: 2).

In one embodiment, a nucleic acid molecule comprising a base sequence encoding a first sucrose phosphorylase is modified so that the sucrose phosphorylase having improved thermostability encoded by a modified nucleic acid molecule is different from the natural sucrose phosphorylase in at least positions corresponding to a combination of the following positions in the amino acid sequence of SEQ ID NO: 2:

(1) A combination of a position corresponding to position 14 in motif sequence 1, a position corresponding to position 29 in motif sequence 1, a position corresponding to position 44 in motif sequence 1, a position corresponding to position 7 in motif sequence 2, a position corresponding to position 19 in motif sequence 2, a position corresponding to position 23 in motif sequence 2, a position corresponding to position 34 in motif sequence 2, and a position corresponding to position 19 in motif sequence 3 (that is, all of the 8 places);

(2) A combination of a position corresponding to position 14 in motif sequence 1, a position corresponding to position 29 in motif sequence 1, a position corresponding to position 44 in motif sequence 1, a position corresponding to position 7 in motif sequence 2, a position corresponding to position 23 in motif sequence 2, a position corresponding to position 34 in motif sequence 2, and a position corresponding to position 19 in motif sequence 3;

(3) A combination of a position corresponding to position 14 in motif sequence 1, a position corresponding to position 7 in motif sequence 2, a position corresponding to position 23 in motif sequence 2, and a position corresponding to position 19 in motif sequence 3;

(4) A combination of a position corresponding to position 14 in motif sequence 1, a position corresponding to position 29 in motif sequence 1, a position corresponding to position 23 in motif sequence 2, and a position corresponding to position 19 in motif sequence 3;

(5) A combination of a position corresponding to position 14 in motif sequence 1, a position corresponding to position 7 in motif sequence 2, a position corresponding to position 23 in motif sequence 2, a position corresponding to position 34 in motif sequence 2, and a position corresponding to position 19 in motif sequence 3;

(6) A combination of a position corresponding to position 14 in motif sequence 1, a position corresponding to position 29 in motif sequence 1, a position corresponding to position 7 in motif sequence 2, a position corresponding to position 34 in motif sequence 2, and a position corresponding to position 19 in motif sequence 3;

(7) A combination of a position corresponding to position 14 in motif sequence 1, a position corresponding to position 29 in motif sequence 1, a position corresponding to position 44 in motif sequence 1, a position corresponding to position 7 in motif sequence 2, a position corresponding to position 19 in motif sequence 2, and a position corresponding to position 23 in motif sequence 2;

(8) A combination of a position corresponding to position 14 in motif sequence 1, a position corresponding to position 29 in motif sequence 1, a position corresponding to position 44 in motif sequence 1, a position corresponding to position 7 in motif sequence 2, a position corresponding to position 23 in motif sequence 2, and a position corresponding to position 34 in motif sequence 2;

(9) A combination of a position corresponding to position 14 in motif sequence 1, a position corresponding to position 29 in motif sequence 1, a position corresponding to position 23 in motif sequence 2, a position corresponding to position 34 in motif sequence 2, and a position corresponding to position 19 in motif sequence 3;

(10) A combination of a position corresponding to position 14 in motif sequence 1, a position corresponding to position 44 in motif sequence 1, a position corresponding to position 19 in motif sequence 2, a position corresponding to position 23 in motif sequence 2, and a position corresponding to position 19 in motif sequence 3;

(11) A combination of a position corresponding to position 14 in motif sequence 1, a position corresponding to position 29 in motif sequence 1, a position corresponding to position 44 in motif sequence 1, a position corresponding to position 23 in motif sequence 2, a position corresponding to position 34 in motif sequence 2, and a position corresponding to position 19 in motif sequence 3;

(12) A combination of a position corresponding to position 7 in motif sequence 2, a position corresponding to position 23 in motif sequence 2, a position corresponding to position 34 in motif sequence 2, and a position corresponding to position 19 in motif sequence 3;

(13) A combination of a position corresponding to position 14 in motif sequence 1, a position corresponding to position 29 in motif sequence 1, a position corresponding to position 7 in motif sequence 2, a position corresponding to position 23 in motif sequence 2, and a position corresponding to position 34 in motif sequence 2;

(14) A combination of a position corresponding to position 7 in motif sequence 2, a position corresponding to position 34 in motif sequence 2, and a position corresponding to position 19 in motif sequence 3;

(15) A combination of a position corresponding to position 29 in motif sequence 1, a position corresponding to position 7 in motif sequence 2, a position corresponding to position 23 in motif sequence 2, and a position corresponding to position 19 in motif sequence 3;

(16) A combination of a position corresponding to position 14 in motif sequence 1, a position corresponding to position 29 in motif sequence 1, a position corresponding to position 19 in motif sequence 2, a position corresponding to position 34 in motif sequence 2, and a position corresponding to position 19 in motif sequence 3;

(17) A combination of a position corresponding to position 14 in motif sequence 1, a position corresponding to position 29 in motif sequence 1, and a position corresponding to position 19 in motif sequence 3;

(18) A combination of a position corresponding to position 14 in motif sequence 1, a position corresponding to position 29 in motif sequence 1, a position corresponding to position 34 in motif sequence 2, and a position corresponding to position 19 in motif sequence 3;

(19) A combination of a position corresponding to position 14 in motif sequence 1, a position corresponding to position 29 in motif sequence 1, a position corresponding to position 44 in motif sequence 1, a position corresponding to position 7 in motif sequence 2, and a position corresponding to position 23 in motif sequence 2;

(20) A combination of a position corresponding to position 44 in motif sequence 1, a position corresponding to position 7 in motif sequence 2, and a position corresponding to position 34 in motif sequence 2;

(21) A combination of a position corresponding to position 44 in motif sequence 1, a position corresponding to position 19 in motif sequence 2, a position corresponding to position 23 in motif sequence 2, and a position corresponding to position 19 in motif sequence 3;

(22) A combination of a position corresponding to position 14 in motif sequence 1, a position corresponding to position 29 in motif sequence 1, and a position corresponding to position 7 in motif sequence 2;

(23) A combination of a position corresponding to position 14 in motif sequence 1, a position corresponding to position 29 in motif sequence 1, a position corresponding to position 23 in motif sequence 2, and a position corresponding to position 34 in motif sequence 2; and

(24) A combination of a position corresponding to position 14 in motif sequence 1 and a position corresponding to position 19 in motif sequence 3.

In another embodiment, a nucleic acid molecule comprising a base sequence encoding a first sucrose phosphorylase is modified so that sucrose phosphorylase having improved thermostability, encoded by a modified nucleic acid molecule is different from the natural sucrose phosphorylase in at least positions corresponding to a combination of the following positions in the amino acid sequence of SEQ ID NO: 2:

(1) A combination of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) (that is, all of the 8 places);

(2) A combination of a position corresponding to threonine at position 47 (T47), a position corresponding to serine at position 62 (S62), a position corresponding to tyrosine at position 77 (Y77), a position corresponding to valine at position 128 (V128), a position corresponding to glutamine at position 144 (Q144), a position corresponding to asparagine at position 155 (N155), and a position corresponding to aspartic acid at position 249 (D249);

(3) A combination of a position corresponding to T47, a position corresponding to V128, a position corresponding to Q144, and a position corresponding to D249;

(4) A combination of a position corresponding to T47, a position corresponding to S62, a position corresponding to Q144, and a position corresponding to D249;

(5) A combination of a position corresponding to T47, a position corresponding to V128, a position corresponding to Q144, a position corresponding to N155, and a position corresponding to D249;

(6) A combination of a position corresponding to T47, a position corresponding to S62, a position corresponding to V128, a position corresponding to N155, and a position corresponding to D249;

(7) A combination of a position corresponding to T47, a position corresponding to S62, a position corresponding to Y77, a position corresponding to V128, a position corresponding to K140, and a position corresponding to Q144;

(8) A combination of a position corresponding to T47, a position corresponding to S62, a position corresponding to Y77, a position corresponding to V128, a position corresponding to Q144, and a position corresponding to N155;

(9) A combination of a position corresponding to T47, a position corresponding to S62, a position corresponding to Q144, a position corresponding to N155, and a position corresponding to D249;

(10) A combination of a position corresponding to T47, a position corresponding to Y77, a position corresponding to K140, a position corresponding to Q144, and a position corresponding to D249;

(11) A combination of a position corresponding to T47, a position corresponding to S62, a position corresponding to Y77, a position corresponding to Q144, a position corresponding to N155, and a position corresponding to D249;

(12) A combination of a position corresponding to V128, a position corresponding to Q144, a position corresponding to N155, and a position corresponding to D249;

(13) A combination of a position corresponding to T47, a position corresponding to S62, a position corresponding to V128, a position corresponding to Q144, and a position corresponding to N155;

(14) A combination of a position corresponding to V128, a position corresponding to N155, and a position corresponding to D249;

(15) A combination of a position corresponding to S62, a position corresponding to V128, a position corresponding to Q144, and a position corresponding to D249;

(16) A combination of a position corresponding to T47, a position corresponding to S62, a position corresponding to K140, a position corresponding to N155, and a position corresponding to D249;

(17) A combination of a position corresponding to T47, a position corresponding to S62, and a position corresponding to D249;

(18) A combination of a position corresponding to T47, a position corresponding to S62, a position corresponding to N155, and a position corresponding to D249;

(19) A combination of a position corresponding to T47, a position corresponding to S62, a position corresponding to Y77, a position corresponding to V128, and a position corresponding to Q144;

(20) A combination of a position corresponding to Y77, a position corresponding to V128, and a position corresponding to N155;

(21) A combination of a position corresponding to Y77, a position corresponding to K140, a position corresponding to Q144, and a position corresponding to D249;

(22) A combination of a position corresponding to T47, a position corresponding to S62, and a position corresponding to V128;

(23) A combination of a position corresponding to T47, a position corresponding to S62, a position corresponding to Q144, and a position corresponding to N155; and

(24) A combination of a position corresponding to T47 and a position corresponding to D249.

The "position corresponding to threonine at position 47 (T47) of the amino acid sequence of SEQ ID NO: 2" as used in the present specification refers to a position which is aligned with threonine at position 47 as set forth in SEQ ID NO: 2, when a subject amino acid sequence and the amino acid sequence of SEQ ID NO: 2 are aligned so that homology between the two sequences is highest, if necessary, by inserting a gap into one of sequences. When a gap is introduced into the amino acid sequence of SEQ ID NO: 2, the gap is not counted when calculating the number of amino acid residues. More preferably, the above phrase refers to position which is aligned with threonine at position 47 of SEQ ID NO: 2 when the amino acid sequence of SEQ ID NO: 2 and a subject amino acid sequence are aligned under the condition of GAP Penalty (Peptide): Insert=−8, Extend=−3, gap Extend on top position: setted (checked), Match Mode: Local Match using a score table of default, in multiple alignment of GENETYX-WIN Ver. 4.0. A score table of default with respect to amino acids is shown in the following Table 2.

TABLE 2

| | | | | | | | | | | | | | | | | | | | |
|---|---|---|---|---|---|---|---|---|---|---|---|---|---|---|---|---|---|---|---|
| C | 12, | | | | | | | | | | | | | | | | | | |
| S | 0, | 2, | | | | | | | | | | | | | | | | | |
| T | −2, | 1, | 3, | | | | | | | | | | | | | | | | |
| P | −3, | 1, | 0, | 6, | | | | | | | | | | | | | | | |
| A | −2, | 1, | 1, | 1, | 2, | | | | | | | | | | | | | | |
| G | −3, | 1, | 0, | −1, | 1, | 5, | | | | | | | | | | | | | |
| N | −4, | 1, | 0, | −1, | 0, | 0, | 2, | | | | | | | | | | | | |
| D | −5, | 0, | 0, | −1, | 0, | 1, | 2, | 4, | | | | | | | | | | | |
| E | −5, | 0, | 0, | −1, | 0, | 0, | 1, | 3, | 4, | | | | | | | | | | |
| Q | −5, | −1, | −1, | 0, | 0, | −1, | 1, | 2, | 2, | 4, | | | | | | | | | |
| H | −3, | −1, | −1, | 0, | −1, | −2, | 2, | 1, | 1, | 3, | 6, | | | | | | | | |
| R | −4, | 0, | −1, | 0, | −2, | −3, | 0, | −1, | −1, | 1, | 2, | 6, | | | | | | | |
| K | −5, | 0, | 0, | −1, | −1, | −2, | 1, | 0, | 0, | 1, | 0, | 3, | 5, | | | | | | |
| M | −5, | −2, | −1, | −2, | −1, | −3, | −2, | −3, | −2, | −1, | −2, | 0, | 0, | 6, | | | | | |
| I | −2, | −1, | 0, | −2, | −1, | −3, | −2, | −2, | −2, | −2, | −2, | −2, | −2, | 2, | 5, | | | | |
| L | −6, | −3, | −2, | −3, | −2, | −4, | −3, | −4, | −3, | −2, | −2, | −3, | −3, | 4, | 2, | 6, | | | |
| V | −2, | −1, | 0, | −1, | 0, | −1, | −2, | −2, | −2, | −2, | −2, | −2, | −2, | 2, | 4, | 2, | 4, | | |
| F | −4, | −3, | −3, | −5, | −4, | −5, | −4, | −6, | −5, | −5, | −2, | −4, | −5, | 0, | 1, | 2, | −1, | 9, | |

TABLE 2-continued

| | C | S | T | P | A | G | N | D | E | Q | H | R | K | M | I | L | V | F | Y | W | B | Z | X |
|---|---|---|---|---|---|---|---|---|---|---|---|---|---|---|---|---|---|---|---|---|---|---|---|
| Y | 0, | −3, | −3, | −5, | −3, | −5, | −2, | −4, | −4, | −4, | 0, | −4, | −4, | −2, | −1, | −1, | −2, | 7, | 10, | | | | |
| W | −8, | −2, | −5, | −6, | −6, | −7, | −4, | −7, | −7, | −5, | −3, | 2, | −3, | −4, | −5, | −2, | −6, | 0, | 0, | 17, | | | |
| B | −4, | 0, | 0, | −1, | 0, | 0, | 2, | 3, | 2, | 1, | 1, | −1, | 1, | −2, | −2, | −3, | −2, | −5, | −3, | −5, | 2, | | |
| Z | −5, | 0, | −1, | 0, | 0, | −1, | 1, | 3, | 3, | 3, | 2, | 0, | 0, | −2, | −2, | −3, | −2, | −5, | −4, | −6, | 2, | 3, | |
| X | 0, | 0, | 0, | 0, | 0, | 0, | 0, | 0, | 0, | 0, | 0, | 0, | 0, | 0, | 0, | 0, | 0, | 0, | 0, | 0, | 0, | 0, | 0 |

The multiple alignment of GENETYX-WIN Ver. 4.0 is based on the following algorithm. In this alignment program, all possible pairs of sequences are aligned, two sequence alignment is performed as a round robin (pair wise alignment) and, among that, sequences of a combination having a high conservation ratio (score in pair wise alignment) are determined as common sequences, a hypothetical sequence is produced from common sequences (a common part remains as it is and, with respect to non-common parts, any one of the sequences is selected). A round robin between all sequences except for the sequence constituting the hypothetical is sequence, and a hypothetical sequence is generated by the same procedure until the final hypothetical sequence is produced. Thereafter, by applying information on insertion and shift of GAP used to produce the hypothetical sequence, to the original sequence, to constitute a whole, and the multiple alignment is completed. A calculation equation for this pair wise alignment is as follows:

When sequences a and b, each having a sequence length of m or n, and respective sequences are expressed as:

a=a1a2a3 ... am
b=b1b2b3 ... bm, a GAP penalty g is indicated by the following equation:

$$-g=s(ai,\phi)=a(\phi,bj).$$

An equation for obtaining an alignment score is as follows:

$$G(0,0)=0$$

$$G(i,0)=i(-g)$$

$$G(0,j)=j(-g)$$

$$-gk=-[\alpha+\beta(k-1)]$$

$$E(i,j)=\{G(i-1,j)-\alpha,E(i-1,j)-\beta\}$$

$$F(i,j)=\max\{G(i,j-1)-\alpha,F(i,j-1)-\beta\}$$

$$G(i,j)=\max\{E(i,j),G(i-1,j-1)+s(ai,bj),F(i,j)\}$$

α is the GAP insertion penalty, and β is the GAP extension penalty. E, F and G are a score matrix and, based on this, a pass matrix is produced.

A position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) are similarly construed.

In multiple alignments of GENETYX-WIN Ver. 4.0, under the aforementioned condition, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20 were aligned with SEQ ID NO: 2. As a result, threonine, isoleucine, phenylalanine, or serine was aligned at a position corresponding to threonine at position 47 (T47) of the amino acid sequence set forth in SEQ ID NO: 2. Serine, alanine, proline or glutamic acid was aligned at a position corresponding to serine at position 62 (S62) of the amino acid sequence set forth in SEQ ID NO: 2. Tyrosine, valine, leucine, histidine, serine or alanine was aligned at a position corresponding to tyrosine at position 77 (Y77) of the amino acid sequence set forth in SEQ ID NO: 2. Valine, isoleucine or leucine was aligned at the position corresponding to valine at position 128 (V128) of the amino acid sequence set forth in SEQ ID NO: 2. Lysine, methionine, threonine, isoleucine, phenylalanine or glutamine was aligned at a position corresponding to lysine at position 140 (K140) of the amino acid sequence set forth in SEQ ID NO: 2. Valine, threonine, arginine, aspartic acid, lysine, serine or glutamine was aligned at the position corresponding to glutamine at position 144 (Q144) of the amino acid sequence set forth in SEQ ID NO: 2. Asparagine, threonine or valine was aligned at the position corresponding to asparagine at position 155 (N155) of the amino acid sequence set forth in SEQ ID NO: 2. Aspartic acid, glycine, valine or glutamic acid was aligned at a position corresponding to aspartic acid at position 249 (D249) of the amino acid sequence set forth in SEQ ID NO: 2. Results of this alignment are shown in FIG. 1A to FIG. 1C. In FIG. 1A to FIG. 1C, "StMuSP" represents the amino acid sequence of a *Streptococcus mutans*-derived sucrose phosphorylase. "StPSP" represents an amino acid sequence of a *Streptococcus pneumoniae*-derived sucrose phosphorylase. "StSSP" represents an amino acid sequence of a *Streptococcus sorbinus*-derived sucrose phosphorylase. "LeuSP1" represents an amino acid sequence of a *Leuconostoc mesenteroides*-derived first sucrose phosphorylase. "LeuSP2" represents an amino acid sequence of a *Leuconostoc mesenteroides*-derived second sucrose phosphorylase. "OenSP" represents an amino acid sequence of an *Oenococcus oeni*-derived sucrose phosphorylase. "LBSP1" represents an amino acid sequence of a *Lactobacillus acidophilus*-derived first sucrose phosphorylase. "LBSP2" represents an amino acid sequence of a *Lactobacillus acidophilus*-derived second sucrose phosphorylase. "ListSP2" represents an amino acid sequence of a *Listeria monocytogenes*-derived sucrose phosphorylase.

In the present specification, the percentage identity of sequences is calculated using maximum matching of GENETYX-WIN Ver. 4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takashi, K., and Gotoh, O. 1984. Sequence Relationships among Various 4.5 S RNA Species J. Biochem. 92:1173-1177). In the present specification, the percentage identity of sequences is calculated using maximum matching of GENETYX-WIN Ver. 4.0 under the condition of Matches=−1; Mismatches=1; Gaps=1; *N+=2.

Table 3 shows the percentage identity (%) obtained by aligning the amino acid sequence (SEQ ID NO: 2) of *Streptococcus mutans*-derived SP, the amino acid sequence (SEQ ID NO: 4) of *Streptococcus pneumoniae*-derived SP, the amino acid sequence (SEQ ID NO: 6) of *Streptococcus sorbinus*-derived SP, the amino acid sequence (SEQ ID NO: 8) of *Leuconostoc mesenteroide*-derived SP, the amino acid sequence (SEQ ID NO: 10) of *Oenococcus oeni*-derived SP, the amino acid sequence (SEQ ID NO: 12) of *Streptococcus mitis*-derived SP, the amino acid sequence (SEQ ID NO: 14) of *Leuconostoc mesenteroides*-derived SP, the amino acid sequence (SEQ ID NO: 16) of *Lactobacillus acidophilus*-derived first SP, the amino acid sequence (SEQ ID NO: 18) of *Lactobacillus acidophilus*-derived second SP, and the amino acid sequence (SEQ ID NO: 20) of *Listeria monocytogenes*-derived SP, by using the maximum matching of GENETYX-WIN Ver. 4.0 under conditions of Matches=−1; Mismatches=1; Gaps=1; and *N+=2.

of SEQ ID NO: 2 is position 77 in the amino acid sequence of SEQ ID: NO: 6, the position corresponding to V128 of the amino acid sequence of SEQ ID NO: 2 is position 128 in the amino acid sequence of SEQ ID NO: 6, the position corresponding to lysine at position 140 (K140) is position 140 in the amino acid sequence of SEQ ID NO: 6, the position corresponding to Q144 of the amino acid sequence of SEQ ID NO: 2 is position 144 in the amino acid sequence of SEQ ID NO: 6, the position corresponding to N155 of the amino acid sequence of SEQ ID NO: 2 is position 155 in the amino acid sequence of SEQ ID NO: 6, and the position corresponding to D249 of the amino acid sequence of SEQ ID NO: 2 is position 249 in the amino acid sequence of SEQ ID NO: 6.

TABLE 3

|  | A.A. |  | StMuSP | StPSP | StSSP | StMiSP | LeuSP1 | LeuSP2 | OenSP | LBSP1 | LBSP2 | ListMSP |
|---|---|---|---|---|---|---|---|---|---|---|---|---|
| *Streptococcus mutans* | 481 | StMuSP | 100.0 | 83.8 | 82.5 | 84.7 | 65.9 | 66.2 | 65.0 | 63.6 | 72.1 | 68.8 |
| *Streptococcus pneumoniae* | 478 | StPSP | 83.8 | 100.0 | 79.2 | 95.2 | 66.7 | 65.2 | 63.8 | 63.1 | 69.0 | 69.0 |
| *Streptococcus sorbinus* | 481 | StSSP | 82.5 | 79.2 | 100.0 | 79.7 | 65.1 | 63.9 | 65.4 | 65.5 | 72.4 | 65.9 |
| *Streptococcus mitis* | 482 | StMiSP | 84.7 | 95.2 | 79.7 | 100.0 | 66.7 | 65.4 | 64.8 | 63.5 | 69.5 | 68.7 |
| *Leuconostoc mesentroides* 1 | 490 | LeuSP1 | 65.9 | 66.7 | 65.1 | 66.7 | 100.0 | 83.5 | 72.2 | 61.0 | 65.2 | 64.9 |
| *Leuconostoc mesentroides* 2 | 485 | LeuSP2 | 66.2 | 65.2 | 63.9 | 65.4 | 83.5 | 100.0 | 70.9 | 60.8 | 64.3 | 65.2 |
| *Oenococcus oeni* | 489 | OenSP | 65.0 | 63.8 | 65.4 | 64.8 | 72.2 | 70.9 | 100.0 | 62.4 | 64.6 | 64.8 |
| *Lactobacillus acidophilus* 1 | 480 | LBSP1 | 63.6 | 63.1 | 65.5 | 63.5 | 61.0 | 60.8 | 62.4 | 100.0 | 69.6 | 61.3 |
| *Lactobacillus acidophilus* 2 | 480 | LBSP2 | 72.1 | 69.0 | 72.4 | 69.5 | 65.2 | 64.6 | 64.6 | 69.6 | 100.0 | 64.8 |
| *Listeria monocytogenes* | 480 | ListMSP | 68.8 | 69.0 | 65.9 | 68.7 | 64.9 | 64.8 | 64.8 | 61.3 | 64.8 | 100.0 |

For example, in *Streptococcus pneumoniae*-derived sucrose phosphorylase, the position corresponding to threonine at position 47 (T47) of the amino acid sequence of SEQ ID NO: 2 is position 47 of the amino acid sequence of SEQ ID NO: 4, the position corresponding to serine at position 62 (S62) of the amino acid sequence of SEQ ID NO: 2 is position 62 in the amino acid sequence of SEQ ID NO: 4, the position corresponding to tyrosine at position 77 (Y77) of the amino acid sequence of SEQ ID NO: 2 is position 77 in the amino acid sequence of SEQ ID NO: 4, the position corresponding to valine at position 128 (V128) of the amino acid sequence of SEQ ID NO: 2 is position 128 in the amino acid sequence of SEQ ID NO: 4, the position corresponding to lysine at position 140 (K140) is position 140 in the amino acid sequence of SEQ ID NO: 4, the position corresponding to glutamine at position 144 (Q144) of the amino acid sequence of SEQ ID NO: 2 is position 144 in the amino acid sequence of SEQ ID NO: 4, the position corresponding to asparagine at position 155 (N155) of the amino acid sequence of SEQ ID NO: 2 is position 155 in the amino acid sequence of SEQ ID NO: 4, and the position corresponding to aspartic acid at position 249 (D249) of the amino acid sequence of SEQ ID NO: 2 is position 249 in the amino acid sequence of SEQ ID NO: 4.

For example, in *Streptococcus sorbinus*-derived sucrose phosphorylase, the position corresponding to T47 of the amino acid sequence of SEQ ID NO: 2 is position 47 in the amino acid sequence of SEQ ID NO: 6, the position corresponding to S62 of the amino acid sequence of SEQ ID NO: 2 is position 62 in the amino acid sequence of SEQ ID NO: 6, the position corresponding to Y77 of the amino acid sequence For example, in *Leuconostoc mesenteroides*-derived sucrose phosphorylase, the position corresponding to T47 of the amino acid sequence of SEQ ID NO: 2 is position 47 in the amino acid sequence of SEQ ID NO: 8, the position corresponding to S62 of the amino acid sequence of SEQ ID NO: 2 is position 62 in the amino acid sequence of SEQ ID NO: 8, the position corresponding to Y77 of the amino acid sequence of SEQ ID NO: 2 is position 77 in the amino acid sequence of SEQ ID NO: 8, the position corresponding to V128 of the amino acid sequence of SEQ ID NO: 2 is position 131 in the amino acid sequence of SEQ ID NO: 8, the position corresponding to lysine at position 140 (K140) of the amino acid sequence of SEQ ID NO: 2 is position 143 in the amino acid sequence of SEQ ID NO: 8, the position corresponding to Q144 of the amino acid sequence of SEQ ID NO: 2 is position 147 in the amino acid sequence of SEQ ID NO: 8, the position corresponding to N155 of the amino acid sequence of SEQ ID NO: 2 is position 158 in the amino acid sequence of SEQ ID NO: 8, and the position corresponding to D249 of the amino acid sequence of SEQ ID NO: 2 is position 252 in the amino acid sequence of SEQ ID NO: 8.

For example, in *Oenococcus oeni*-derived sucrose phosphorylase, the position corresponding to T47 of the amino acid sequence of SEQ ID NO: 2 is position 47 in the amino acid sequence of SEQ ID NO: 10, the position corresponding to S62 of the amino acid sequence of SEQ ID NO: 2 is position 62 in the amino acid sequence of SEQ ID NO: 10, the position corresponding to Y77 of the amino acid sequence of SEQ ID NO: 2 is position 77 in the amino acid sequence of SEQ ID NO: 10, the position corresponding to V128 of the amino acid sequence of SEQ ID NO: 2 is position 128 in the amino acid sequence of SEQ ID NO: 10, the position corresponding to K140 of the amino acid sequence of SEQ ID NO: 2 is position 140 in the amino acid sequence of SEQ ID NO: 10, the position corresponding to Q144 of the amino acid sequence of SEQ ID NO: 2 is position 144 in the amino acid sequence of SEQ ID NO: 10, the position corresponding to N155 of the amino acid sequence of SEQ ID NO: 2 is position 155 in the amino acid sequence of SEQ ID NO: 10, and the position corresponding to D249 of the amino acid sequence of SEQ ID NO: 2 is position 249 in the amino acid sequence of SEQ ID NO: 10.

For example, in *Streptococcus mitis*-derived sucrose phosphorylase, the position corresponding to T47 of the amino acid sequence of SEQ ID NO: 2 is position 47 in the amino acid sequence of SEQ ID NO: 12, the position corresponding to S62 of the amino acid sequence of SEQ ID NO: 2 is position 62 in the amino acid sequence of SEQ ID NO: 12, the position corresponding to Y77 of the amino acid sequence of SEQ ID NO: 2 is position 77 in the amino acid sequence of SEQ ID NO: 12, the position corresponding to V128 of the amino acid sequence of SEQ ID NO: 2 is position 128 in the amino acid sequence of SEQ ID NO: 12, the position corresponding to K140 of the amino acid sequence of SEQ ID NO: 2 is position 140 in the amino acid sequence of SEQ ID NO: 12, the position corresponding to Q144 of the amino acid sequence of SEQ ID NO: 2 is position 144 in the amino acid sequence of SEQ ID NO: 12, the position corresponding to N155 of the amino acid sequence of SEQ ID NO: 2 is position 155 in the amino acid sequence of SEQ ID NO: 12, and the position corresponding to D249 of the amino acid sequence of SEQ ID NO: 2 is position 249 in the amino acid sequence of SEQ ID NO: 12.

For example, in *Leuconostoc mesenteroide*-derived second sucrose phosphorylase, the position corresponding to T47 of the amino acid sequence of SEQ ID NO: 2 is position 47 in the amino acid sequence of SEQ ID NO: 14, the position corresponding to S62 of the amino acid sequence of SEQ ID NO: 2 is position 62 in the amino acid sequence of SEQ ID NO: 14, the position corresponding to Y77 of the amino acid sequence of SEQ ID NO: 2 is position 77 in the amino acid sequence of SEQ ID NO: 14, the position corresponding to V128 of the amino acid sequence of SEQ ID NO: 2 is position 131 in the amino acid sequence of SEQ ID NO: 14, the position corresponding to K140 of the amino acid sequence of SEQ ID NO: 2 is position 143 in the amino acid sequence of SEQ ID NO: 14, the position corresponding to Q144 of the amino acid sequence of SEQ ID NO: 2 is position 147 in the amino acid sequence of SEQ ID NO: 14, the position corresponding to N155 of the amino acid sequence of SEQ ID NO: 2 is position 158 in the amino acid sequence of SEQ ID NO: 14, and the position corresponding to D249 of the amino acid sequence of SEQ ID NO: 2 is position 252 in the amino acid sequence of SEQ ID NO: 14.

For example, in *Lactobacillus acidophilus*-derived first sucrose phosphorylase, the position corresponding to T47 of the amino acid sequence of SEQ ID NO: 2 is position 47 in the amino acid sequence of SEQ ID NO: 16, the position corresponding to S62 of the amino acid sequence of SEQ ID NO: 2 is position 62 in the amino acid sequence of SEQ ID NO: 16, the position corresponding to Y77 of the amino acid sequence of SEQ ID NO: 2 is position 77 in the amino acid sequence of SEQ ID NO: 16, the position corresponding to V128 of the amino acid sequence of SEQ ID NO: 2 is position 128 in the amino acid sequence of SEQ ID NO: 16, the position corresponding to K140 of the amino acid sequence of SEQ ID NO: 2 is position 140 in the amino acid sequence of SEQ ID NO: 16, the position corresponding to Q144 of the amino acid sequence of SEQ ID NO: 2 is position 144 in the amino acid sequence of SEQ ID NO: 16, the position corresponding to N155 of the amino acid sequence of SEQ ID NO: 2 is position 155 in the amino acid sequence of SEQ ID NO: 16, and the position corresponding to D249 of the amino acid sequence of SEQ ID NO: 2 is position 249 in the amino acid sequence of SEQ ID NO: 16.

For example, in *Lactobacillus acidophilus*-derived second sucrose phosphorylase, the position corresponding to T47 of the amino acid sequence of SEQ ID NO: 2 is position 47 in the amino acid sequence of SEQ ID NO: 18, the position corresponding to S62 of the amino acid sequence of SEQ ID NO: 2 is position 62 in the amino acid sequence of SEQ ID NO: 18, the position corresponding to Y77 of the amino acid sequence of SEQ ID NO: 2 is position 77 in the amino acid sequence of SEQ ID NO: 18, the position corresponding to V128 of the amino acid sequence of SEQ ID NO: 2 is position 128 in the amino acid sequence of SEQ ID NO: 18, the position corresponding to K140 of the amino acid sequence of SEQ ID NO: 2 is position 140 in the amino acid sequence of SEQ ID NO: 18, the position corresponding to Q144 of the amino acid sequence of SEQ ID NO: 2 is position 144 in the amino acid sequence of SEQ ID NO: 18, the position corresponding to N155 of the amino acid sequence of SEQ ID NO: 2 is position 155 in the amino acid sequence of SEQ ID NO: 18, and the position corresponding to D249 of the amino acid sequence of SEQ ID NO: 2 is position 249 in the amino acid sequence of SEQ ID NO: 18.

For example, in *Listeria monocytogenes*-derived sucrose phosphorylase, the position corresponding to T47 of the amino acid sequence of SEQ ID NO: 2 is position 47 in the amino acid sequence of SEQ ID NO: 20, the position corresponding to S62 of the amino acid sequence of SEQ ID NO: 2 is position 62 in the amino acid sequence of SEQ ID NO: 20, the position corresponding to Y77 of the amino acid sequence of SEQ ID NO: 2 is position 77 in the amino acid sequence of SEQ ID NO: 20, the position corresponding to V128 of the amino acid sequence of SEQ ID NO: 2 is position 128 in the amino acid sequence of SEQ ID NO: 20, the position corresponding to K140 of the amino acid sequence of SEQ ID NO: 2 is position 140 in the amino acid sequence of SEQ ID NO: 20, the position corresponding to Q144 of the amino acid sequence of SEQ ID NO: 2 is position 144 in the amino acid sequence of SEQ ID NO: 20, the position corresponding to N155 of the amino acid sequence of SEQ ID NO: 2 is position 155 in the amino acid sequence of SEQ ID NO: 20, and the position corresponding to D249 of the amino acid sequence of SEQ ID NO: 2 is position 249 in the amino acid sequence of SEQ ID NO: 20.

A position of an amino acid residue which improves thermostability can be determined by not only alignment of a subject sequence with the sequence of 418 amino acid residue in length set forth in SEQ ID NO: 2, but also by alignment with one or more sequences selected from the group consisting of the aforementioned motif sequences 1, 2, and 3. As far as SP amino acid sequences (the amino acid sequence of SEQ ID NO: 4, the amino acid sequence of SEQ ID NO: 6, the amino acid sequence of SEQ ID NO: 8, the amino acid sequence of SEQ ID NO: 10, the amino acid sequence of SEQ ID NO: 12, the amino acid sequence of SEQ ID NO: 14, the amino acid sequence of SEQ ID NO: 16 and the amino acid sequence of SEQ ID NO: 20) having high homology with SEQ ID NO: 2 (for example, having about 40% or more homology with the amino acid sequence of SEQ ID NO: 2) were aligned, the thus determined position is the same in either the case where SEQ ID NO: 2 is used and the case where motif sequences 1, 2, and 3 are used.

Motif sequence 1 is well conserved in sucrose phosphorylases, and particularly well conserved in sucrose phosphorylases derived from the genus *Streptococcus*. It can be said that the position corresponding to threonine at position 47 (T47) of the amino acid sequence set forth in SEQ ID NO: 2 is a position corresponding to position 14 in motif sequence 1.

Motif sequence 2 is well conserved in sucrose phosphorylases. It can be said that the position corresponding to valine at position 128 (V128) of the amino acid sequence set forth in SEQ ID NO: 2 is a position corresponding to position 7 in motif sequence 2.

Motif sequence 3 is conserved in sucrose phosphorylases. It can be said that the position corresponding to aspartic acid at position 249 (D249) of the amino acid sequence set forth in SEQ ID NO: 2 is a position corresponding to position 19 in motif sequence 3.

In this manner, the position of an amino acid residue which improves thermostability can be also specified using the motif sequences. A position of an amino acid residue which improves thermostability can be at least one position selected from the group consisting of a position corresponding to position 14, a position corresponding to position 29 and a position corresponding to position 44 in motif sequence 1: AVGGVHLLPFFPSTGDRGFAPIDYHEVDSAFGDWDDVKRLGEKYYLMFDFMINHIS (SEQ ID NO. 25); a position corresponding to position 7, a position corresponding to position 19, a position corresponding to position 23 and a position corresponding to position 34 in motif sequence 2: RPTQEDVDLIYKRKDRAPKQEIQFADGSVEHLWNTFGEEQID (SEQ ID NO. 26); and a position corresponding to position 19 in motif sequence 3: ILPEIHEHYTIQFKIADHDYYVYDFALPMVTLYSLYSG (SEQ ID NO. 27).

Therefore, in the method according to the present invention, it can be said that a nucleic acid molecule comprising a base sequence encoding first sucrose phosphorylase is modified so that the sucrose phosphorylase having improved thermostability, encoded by a modified nucleic acid has an amino acid residue which is different from an amino acid residue of the natural sucrose phosphorylase in at least one position selected from the group consisting of a position corresponding to position 14, a position corresponding to position 29 and a position corresponding to position 44 in motif sequence 1: AVGGVHLLPFFPSTGDRGFAPIDYHEVDSAFGDWDDVKRLGEKYYLMFDFMINHIS (SEQ ID NO. 25); a position corresponding to position 7, a position corresponding to position 19, a position corresponding to position 23 and a position corresponding to position 34 in motif sequence 2: RPTQEDVDLIYKRKDRAPKQEIQFADGSVEHLWNTFGEEQID (SEQ ID NO. 26); and a position corresponding to position 19 in motif sequence 3: ILPEIHEHYTIQFKIADHDYYVYDFALPMVTLYSLYSG (SEQ ID NO. 27).

In the present specification, the "motif sequence" refers to a partial sequence which is seen between amino acid sequences of a plurality of proteins, and is commonly or highly conserved. Generally, the motif sequence has particular function in many cases, but in the present specification, even when a particular function is not identified, as long as the sequences is conserved between a plurality of amino acid sequences, this is called motif sequence.

An amino acid residue "at position 14 in a motif sequence 1" refers to an amino acid residue which is 14th when counted in order, when the amino acid residue at an N-terminus (left end) of the motif sequence 1 is taken to be position 1. "Position 29 in motif sequence 1", "position 44 in motif sequence 1", "position 7 in motif sequence 2", "position 19 in motif sequence 2", "position 23 in motif sequence 2", "position 34 in motif sequence 2", "position 19 in motif sequence 3" and the like are similar.

These motif sequences are generally well conserved in sucrose phosphorylases. The position of motif sequence 1, the position of motif sequence 2 and the position of motif sequence 3 (first half) are shown in FIG. 1A. The position of motif sequence 3 (latter half) is shown in FIG. 1B.

As used herein, "a position corresponding to position 14 in a motif sequence 1: AVGGVHLLPFFPSTGDRGFAPIDYHEVDSAFGDWDDVKRLGEKYYLMFDFMINHIS" (SEQ ID NO. 25) refers to position which is aligned with amino acid residue at position 14 in motif sequence 1 when a subject amino acid sequence and motif sequence 1 are aligned, without inserting a gap, so that homology between sequences is greatest. More preferably, it refers to the position which is aligned with the amino acid residue at position 14 in motif sequence 1 when the amino acid sequence of motif sequence 1 and a subject amino acid sequence are aligned under the condition of GAP Penalty (Peptide): Insert=−8, Extend=−3, gap Extend on top position: setted (checked), Match Mode: Local Match using a score table of default, in multiple alignment of GENETYX-WIN Ver. 4.0.

Position 29 in motif sequence 1, position 44 in motif sequence 1, position 7 in motif sequence 2, position 19 in motif sequence 2, position 23 in motif sequence 2, position 34 in motif sequence 2, and position 19 in motif sequence 3 are similarly construed.

Using multiple alignment of GENETYX-WIN Ver. 4.0 under the aforementioned conditions, the amino acid sequence (SEQ ID NO: 4) of *Streptococcus pneumoniae*-derived SP, the amino acid sequence (SEQ ID NO: 6) of *Streptococcus sorbinus*-derived second SP, the amino acid sequence (SEQ ID NO: 8) of *Leuconostoc mesenteroides*-derived SP, the amino acid sequence (SEQ ID NO: 10) of *Oenococcus oeni*-derived SP, the amino acid sequence (SEQ ID NO: 12) of *Streptococcus mitis*-derived SP, the amino acid sequence (SEQ ID NO: 14) of *Leuconostoc mesenteroides*-derived second SP, the amino acid sequence (SEQ ID NO: 16) of *Lactobacillus acidophilus*-derived first SP, the amino acid sequence (SEQ ID NO: 18) of *Lactobacillus acidophilus*-derived second SP and the amino acid sequence (SEQ ID NO: 20) of *Listeria monocytogenes*-derived SP were aligned with the amino acid sequence (SEQ ID NO: 2) of *Streptococcus mutans*-derived SP.

Further, using multiple alignment of GENETYX-WIN Ver. 4.0 under the aforementioned conditions, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20 were aligned with each motif sequence (motif sequence 1, 2 or 3). As a result, threonine or asparagine was aligned with a position corresponding to position 14 in motif sequence 1, serine, proline or alanine was aligned with a position corresponding to position 29 in motif sequence 1, tyrosine was aligned with a position corresponding to position 44 in motif sequence 1, valine, isoleucine or leucine was aligned with a position corresponding to position 7 in motif sequence 2, lysine, methionine, threonine, isoleucine, tyrosine or phenylalanine was aligned with a position corresponding to position 19 in motif sequence 2, glutamine, valine, threonine, lysine or glutamic acid was aligned with a position corresponding to position 23 in motif sequence 2, asparagine was aligned with a position corresponding to position 34 in motif sequence 2, and aspartic acid or glycine was aligned with a position corresponding to position 19 in motif sequence 3. Motif sequences 1, 2 and 3 are partial sequences in SEQ ID NO: 2.

Regarding each of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, the results of an alignment using a full length of SEQ ID NO: 2, and results of an alignment using motif sequences 1, 2 and 3 were compared. As a result, in each of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, a position corresponding to position 47 of SEQ ID NO: 2, and a position corresponding to position 14 in motif sequence 1 were the same. A position corresponding to position 62 of SEQ ID NO: 2, and a position corresponding to position 29 in motif 1 were the same. A position corresponding to position 77 of SEQ ID NO: 2, and a position corresponding to position 44 in motif 1 were the same. A position corresponding to position 128 of SEQ ID NO: 2, and a position corresponding to position 7 in motif 2 were the same. A position corresponding to position 140 of SEQ ID NO: 2, and a position corresponding to position 19 in motif 2 were the same. A position corresponding to position 144 of SEQ ID NO: 2, and a position corresponding to position 23 in motif 2 were the same. A position corresponding to position 155 of SEQ ID NO: 2, and a position corresponding to position 34 in motif 2 were the same. A position corresponding to position 249 of SEQ ID NO: 2, and a position corresponding to position 19 in motif 3 were the same. In this manner, it was confirmed that, even when alignment was performed using motif sequences, the same positions are specified as those specified when the amino acid sequence of SEQ ID NO: 2 is used.

A nucleic acid molecule comprising a modified base sequence obtained by modifying a nucleic acid molecule comprising a base sequence encoding the amino acid sequence represented in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 or SEQ ID NO: 20 set forth in the Sequence Listing is within the scope of the present invention.

A nucleic acid molecule comprising a modified base sequence obtained by modifying a nucleic acid molecule comprising a base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19 set forth in the Sequence Listing is within the scope of the present invention.

A nucleic acid molecule comprising a modified base sequence obtained by modifying a nucleic acid molecule comprising a base sequence encoding an amino acid sequence having at least 40% (preferably at least 60%) identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20 as set forth in the Sequence Listing is within the scope of the present invention.

In the present invention, "identity" of a sequence (such as an amino acid sequence and a base sequence) refers to the degree of occurrence of the same amino acid (base when base sequences are compared) between two sequences. Identity is generally determined by comparing two amino acid sequences or two base sequences, and comparing these two sequences which are aligned in an optimal format, which can contain additions or deletions. Percentage identity is calculated by determining the number of positions where an amino acid (base when base sequences are compared) is the same between these two sequences, dividing the number of the same positions by a total number of compared positions, and multiplying the obtained result by 100 in order to obtain a percentage identity between the two sequences.

As an example, an amino acid sequence of first (for example, natural) sucrose phosphorylase used for obtaining sucrose phosphorylase having improved thermostability of the present invention may, in one embodiment, be the same as, that is, 100% identical with an amino acid sequence (i.e. control amino acid sequence) selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18 and SEQ ID NO: 20; or this amino acid sequence may, in another embodiment, be altered in up to certain number of amino acid residues as compared with a control amino acid sequence. Such alterations can be selected from the group consisting of a deletion, a substitution including conservative and non-conservative substitution, or an insertion of at least one amino acid. This alteration may occur at a position of an amino terminus or a carboxyl terminus of a control amino acid sequence, or may occur at any position other than these terminuses. Alteration of an amino acid residue may be interspersed with one residue, or a few residues may be contiguous.

Similarly, a base sequence encoding an amino acid sequence of first (for example, natural) sucrose phosphorylase used for obtaining sucrose phosphorylase having improved thermostability of the present invention may be altered in up to certain number of amino acid residues as compared with a nucleotide sequence encoding a control amino acid sequence (that is, a control amino acid sequence). Such alterations can be selected from the group consisting of a deletion, a substitution including transition and transversion, or an insertion of at least one nucleotide. This alteration may occur at a position of the 5' terminus or the 3' terminus of a control base sequence, or may occur at any position other than these terminuses. Alteration of a base may be interspersed with one residue, or a few bases may be contiguous.

A nucleotide change can generate a nonsense, missense or frame shift mutation in a code sequence, and can thus change the SP encoded by such a changed base sequence.

When two amino acid sequences are directly compared with each other, these amino acid sequences are preferably identical between these amino acid sequences, in typically at least 20%, preferably at least 30%, more preferably at least 40%, still more preferably at least 50%, particularly preferably at least 60%, 70%, 80%, 90%, 95%, 96%, 97%, 98% or 99% of amino acids.

As a first (for example, natural) enzyme or nucleic acid molecule, an enzyme or nucleic acid molecule having a sequence that is not identical with, but is homologous to, the base sequence encoding the first sucrose phosphorylase or the amino acid sequence of the first sucrose phosphorylase, as specifically described in the present specification (for example, SEQ ID NOS: 1, 2 and the like) can be used. Such an enzyme or nucleic acid molecule having homology with the first (for example, natural) enzyme or nucleic acid molecule includes, but are not limited to, in the case of a nucleic acid, nucleic acid molecules containing a base sequence having at least about 30%, about 35%, about 40%, about 45%, about 50%, about 55%, about 60%, about 65%, about 70%, about 75%, about 80%, about 85%, about 90%, about 95%, or about 99% identity with a comparison subject sequence, and, in the case of a enzyme, includes, but are not limited to, enzymes having an amino acid sequence having at least about 40%, about 45%, about 50%, about 55%, about 60%, about 65%, about 70%, about 75%, about 80%, about 85%, about 90%, about 95%, or about 99% identity with a comparison subject sequence, when compared in maximum matching in for example GENETYX-WIN Ver. 4.0 under the conditions described above.

A nucleic acid molecule comprising a modified base sequence obtained by modifying a nucleic acid molecule which hybridizes under stringent condition with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19 as set forth in the Sequence Listing is within the scope of the present invention. A nucleic acid molecule comprising a modified base sequence obtained by modifying a nucleic acid molecule which hybridizes under stringent conditions with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19 as set forth in the Sequence Listing is also within the scope of the present invention. Those skilled in the art can easily select a desired sucrose phosphorylase gene.

As used herein, the term "stringent conditions" refers to conditions under which a sequence hybridizes with a specific sequence, but not with a non-specific sequence. Selection of appropriate stringent conditions is well-known to those skilled in the art, and is described, for example, in Molecular Cloning (Sambrook, et al., supra). Specifically, the conditions mean, for example, that a polynucleotide which can be identified using the conditions under which hybridization is performed at 65° C. in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyviny pyrrolidone), 10% dextran sulfate, and 20 μg/ml denatured sheared salmon sperm DNA using a filter on which a DNA derived from a colony or a plaque has been immobilized, and a filter is washed under the condition of 65° C. using a SSC (saline-sodium citrate) solution having a 0.1 to 2-fold concentration (a composition of a SSC solution having a 1-fold concentration is 150 mM sodium chloride, 15 mM sodium citrate).

A modified nucleic acid molecule used in the method of the present invention may be a nucleic acid molecule which was conservatively modified relative to a nucleic acid molecule comprising a base sequence encoding a first sucrose phosphorylase. In a specific embodiment. The conservatively modified nucleic acid molecule preferably has a conservative modification other than the objective modification in the present invention. The "nucleic acid molecule which was conservatively modified relative to a nucleic acid molecule comprising a base sequence encoding first sucrose phosphorylase" refers to a nucleic acid molecule comprising a base sequence encoding an amino acid sequence which is the same or essentially the same as an amino acid sequence encoded by a base sequence encoding the first sucrose phosphorylase. The "amino acid sequence which is essentially the same as an amino acid sequence encoded by a base sequence encoding first sucrose phosphorylase" refers to an amino acid sequence having essentially the same enzyme activity as that of first sucrose phosphorylase. Due to degeneracy of a genetic code, many functionally equivalent base sequences encode a prescribed amino acid sequence. For example, codons GCA, GCC, GCG and GCU all encode the amino acid alanine. Therefore, at all positions where alanine is specified by a GCA codon, the codon can be changed to GCC, GCG or GCU without changing the encoded alanine. Similarly, regarding an amino acid which can be encoded by a plurality of codons, at all positions where the amino acid is specified by a codon, the codon can be changed to any another codon encoding the amino acid without changing the particular amino acid coded. Such a variation in a base sequence is a "silent mutation" which is one kind of conservatively modified mutation. All base sequences in the present specification which encode a polypeptide also include all possible silent alterations of the nucleic acid. Silent mutation includes "silent substitution" in which a coding nucleic acid is not changed, and the case where a nucleic acid does not originally encode an amino acid. When a certain nucleic acid encodes an amino acid, silent mutation has the same meaning as that of silent substitution. In the present specification, "silent substitution" refers to substitution of a base sequence encoding a certain amino acid with another base sequence encoding the same amino acid, in a base sequence. Based on the phenomenon of degeneracy in a genetic code, in the case where there are a plurality of base sequences encoding a certain amino acid (e.g. glycine), such a silent substitution is possible. Therefore, a polypeptide having an amino acid sequence encoded by a base sequence produced by silent substitution has the same amino acid sequence as that of the original polypeptide. Thus, a polypeptide having an amino acid sequence encoded by a base sequence formed by silent substitution has the same amino acid sequence as the original polypeptide. Therefore, the sucrose phosphorylase having improved thermostability of the present invention can include silent substitutions at a base sequence level, in addition to modification which is aimed a by the present invention (substitution is performed so that the sucrose phosphorylase has an amino acid residue which is different from an amino acid residue of the natural sucrose phosphorylase in at least one position selected from the group consisting of a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3; or at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249), in the amino acid sequence of SEQ ID NO: 2). In the art, it is understood that each codon in a nucleic acid (except for AUG which is only one codon usually encoding methionine, and TGG which is only one codon usually encoding tryptophan) can be modified in order to produce the functionally same molecule. Therefore, each silent mutation of a nucleic acid encoding a polypeptide is implicitly included in each described sequence. Preferably, such the alteration can be performed so that substitution of cysteine, which is an amino acid that greatly influences the conformation of a polypeptide, is avoided.

A base sequence encoding sucrose phosphorylase having improved thermostability of the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (e.g. Sharp, et al., Nucleic Acids Research 16, No. 17, p. 8207 (1988)).

(2.3 Making Expression Vectors)

An expression vector is made using a nucleic acid molecule comprising the base sequence modified as described above. A method for preparing an expression vector using a particular nucleic acid sequence is well-known to those skilled in the art.

When a nucleic acid molecule is referred in the present specification, a "vector" refers to a nucleic acid molecule which can transfer an objective base sequence into an objective cell. Examples of such vectors include a vector which can autonomously replicate in an objective cell, or can be incorporated into a chromosome of an objective cell, and has a promoter at a position suitable for transcribing a modified base sequence. In the present specification, the vector may be a plasmid.

As used herein, the "expression vector" refers to a vector which can express a modified base sequence (i.e. base sequence encoding modified sucrose phosphorylase) in an objective cell. An expression vector contains, in addition to a modified base sequence, various regulation elements such as a promoter regulating expression thereof and, if necessary, factors necessary for replication in an objective cell and selection of a recombinant (e.g. origin of replication (ori), and a selectable marker such as a drug resistant gene). In an expression vector, a modified base sequence is operably linked so that it is transcribed and translated. Regulation elements include a promoter, a terminator and an enhancer. In addition, when secretion of an expressed enzyme outside a cell is intended, a base sequence encoding a secretion signal peptide is linked upstream of a modified base sequence in the correct reading frame. It is a matter well-known to those skilled in the art, that both the type of an expression vector used for introduction into a particular organism (e.g. bacterium), and the kind of a regulation element and other factors used in the expression vector, can vary depending on an objective cell.

As used herein, the "terminator" is a sequence which is situated downstream of a protein coding region, and is involved in termination of transcription upon transcription of a base sequence into an mRNA, and in the addition of a poly A sequence. It is known that the terminator influences the expression level of a gene by involving the stability of an mRNA.

As used herein, the "promoter" refers to a region on a DNA which determines a transcription initiation site of a gene, and directly regulates the transcription frequency, and is a base sequence to which a RNA polymerase binds, thereby, initiating transcription. Since the region of a promoter is usually a region about 2 kbp or less upstream of a first exon of a putative protein coding region in many cases, when a protein coding region in a genome base sequence is predicted using a DNA analyzing software, a promoter region can be putative. A putative promoter region varies with every structural gene, and is usually upstream of a structural gene without limitation, and may be downstream of a structural gene. Preferably, a putative promoter region is present about 2 kbp or less upstream of a first exon translation initiation point.

As used herein, the "enhancer" can be used for enhancing the expression efficiency of an objective gene. Such an enhancer is well-known in the art. A plurality of enhancers can be used, but only one may be used, or may not be used at all.

As used herein, "operably linked" refers to when a desired base sequence is placed under the control of a transcription and translation regulating sequence (e.g. promoter, enhancer and the like) or a translation regulating sequence which effect expression (i.e. operation). In order that a promoter is operably linked to a gene, usually, a promoter is disposed immediately upstream of the gene, but it is not necessary that a promoter is disposed adjacent to the gene.

In order to operably link a modified nucleic acid sequence to the aforementioned regulation element, an objective sucrose phosphorylase gene should be processed in some cases. Examples include the case where the distance between a promoter and a coding region is too long, and reduction in a transcription efficiency is predicted, the case where the distance between a ribosome binding site and a translation initiation codon is not suitable, and the like. Examples of the procession means include digestion with a restriction enzyme, digestion with an exonuclease such as Bal31 and ExoIII, or introduction of site-directed mutagenesis using a single-stranded DNA such as M13 or PCR.

(2.4 Expression of Sucrose Phosphorylase Having Improved Thermostability)

Then, the expression vector prepared as described above is introduced into a cell, thereby, the sucrose phosphorylase having improved thermostability is expressed.

In the present specification, "expression" of an enzyme refers to in vivo or in vitro transcription and translation of a base sequence encoding the enzyme, and production of the encoded enzyme.

A cell into which an expression vector is introduced (also referred to as a host) includes prokaryotes and eukaryotes. A cell into which an expression vector is introduced can be easily selected, taking various conditions such as ease of expression of sucrose phosphorylase, ease of culturing, growth rate, and safety into consideration. For example, when sucrose phosphorylase is used in synthesizing amylose having a high molecular weight, since it is preferable that the sucrose phosphorylase does not contain amylase as a contaminant, it is preferable to use a cell which does not produce amylase or produce amylase only at a low level. Examples of such a cell include microorganisms such as bacteria and fungi. Examples of more preferable cells include mesophilic microorganisms (e.g. *Escherichia coli, Bacillus subtilis*). In the present specification, the "mesophilic microorganism" is a microorganism having a growth temperature in a normal temperature environment, and particularly refers to a microorganism having an optimal growth temperature of 20° C. to 40° C. A cell may be such as a microorganism cell, or may be a plant or animal cell. Depending on a cell to be used, an enzyme of the present invention can be an enzyme which has undergone post-translational processing. A plant includes, but is not limited to, for example, a dicot, and a monocot such as rice, wheat, barley and corn. A cereal such as rice has a nature of accumulating a storage protein in a seed and, using a storage protein system, the cereal can be expressed so that sucrose phosphorylase having improved thermostability of the present invention is accumulated in a seed (see Japanese Laid-Open Publication No. 2002-58492 specification).

In the method of the present invention, the technique of introducing an expression vector into a cell may be any technique known in the art. Examples of such the technique include, for example, transformation, transduction, and transfection. Such the technique of introducing a nucleic acid molecule is well-known in the art, and is conventional, and described, for example, in Ausubel F. A., et al. ed. (1988), Current Protocols in Molecular Biology, Wiley, New York, N.Y.; Sambrook J, et al. (1987) Molecular Cloning: A Laboratory Manual, 2$^{nd}$ Ed., Cold Spring Harbor Laboratory Press, Cold Spring Harbor, N.Y., and Bessatsu Jikken-igaku "Idenshidounyu & Hatsugen kaiseki jikkenhou", Yodosha, 1997.

When a plant cell is used as a cell, a method of re-differentiating a transformant into a tissue or a plant is well-known in the art. Examples of such a method are described in following: Rogers, et al., Methods in Enzymology 118:627-640 (1986); Tabata, et al., Plant Cell Physiol., 28:73-82 (1987); Shaw, Plant Molecular Biology: APractical Approach. IRL press (1988); Shimamoto, et al., Nature 338: 274 (1989); and Maliga, et al., Methods in Plant Molecular Biology: A laboratory course. Cold Spring Harbor Laboratory Press (1995). A method of transforming a woody plant is described in Molecular Biology of Woody Plants (Vol. I, II) (ed. S. Mohan Jain, Subhash C. Minocha), Kluwer Academic Publishers, (2000). In addition, a method of transforming a woody plant is described in detail, for example, in Plant Cell Reports (1999) 19:106-110. Therefore, those skilled in the art can re-differentiate a transformant by appropriately using the aforementioned well-known method depending on an objective transgenic plant. An objective gene is introduced in the thus obtained transgenic plant, and the introduction of the gene can be confirmed using known methods such as Northern blotting, and Western blot analysis or other well-known conventional techniques.

By culturing a cell into which an expression vector has been introduced, and has acquired the ability to express a sucrose phosphorylase having improved thermostability (also referred to as transformed cell), sucrose phosphorylase having improved thermostability can be expressed in a cell. The) condition of culturing a transformed cell is appropriately selected depending on a kind of a host cell to be used, and a kind of an expression regulating factor in an expression vector. For example, a usual shaking culture method can be used.

A medium used for culturing a transformed cell is not particularly limited as long as the cell used is grown, and can express objective sucrose phosphorylase having improved thermostability. In a medium, in addition to a carbon source and a nitrogen source, inorganic salts such as salts of phosphoric acid, $Mg^{2+}$, $Ca^{2+}$, $Mn^{2+}$, $Fe^{2+}$, $Fe^{3+}$, $Zn^{2+}$, $Co^{2+}$, $Ni^{2+}$, $Na^+$, $K^+$ and the like can be used alone, or by appropriately mixing them, if necessary. In addition, if necessary, various inorganic substances or organic substances necessary for growing a transformed cell, or expressing objective sucrose phosphorylase having improved thermostability may be added.

A temperature for culturing a transformed cell can be selected so as to be suitable for growing a transformed cell to be used. Usually, the temperature is 15° C. to 60° C. Culturing of a transformed cell is continued for a sufficient time to express sucrose phosphorylase having improved thermostability.

When an expression vector having an inducible promoter is used, expression can be controlled by addition of an inducer, change of a culturing temperature, and adjustment of medium components. For example, when an expression vector having a lactose inducible promoter is used, expression can be induced by adding isopropyl-β-D-thiogalactopyranoside (IPTG).

(2.5 Recovery of Sucrose Phosphorylase Having Improved Thermostability)

The thus expressed sucrose phosphorylase having improved thermostability can be then recovered. For example, when the expressed sucrose phosphorylase having improved thermostability is accumulated in a transformed cell, the transformed cells are cultured under an appropriate condition, then, a cell is recovered from a culture of the transformed cells by centrifuging or filtering the culture. The recovered cell is suspended in a suitable buffer, and is crushed using, for example, ultrasound and by centrifuging or filtering to obtain a supernatant. When the expressed sucrose phosphorylase having improved thermostability is accumulated in a cell, and when the expressed sucrose phosphorylase having improved thermostability is secreted to the outside of the transformed cells, the transformed cells are cultured as described above, and then the culture is centrifuged or filtered thereby separating the cells to obtain a supernatant. When sucrose phosphorylase having improved thermostability is accumulated in the transformed cells or secreted into the outside of the transformed cells, the resulting supernatant which contains the sucrose phosphorylase having improved thermostability is concentrated by a usual means (for example, salting-out, solvent precipitation, ultrafiltration) to obtain a fraction containing the sucrose phosphorylase having improved thermostability. This fraction is subjected to filtration, centrifugation or desalting to obtain a crude enzyme solution. Further, a crude enzyme or a purified enzyme having improved specific activity is obtained by purifying the crude enzyme solution by a method of appropriately combining conventional enzyme purifying means such as lyophilization, isoelectric focusing, ion exchange chromatography and crystallization. When an enzyme hydrolyzing an α-glucan such as α-amylase is not contained, a crude enzyme as it is can be used, for example, in preparation of an α-glucan having a high-molecular weight.

By producing sucrose phosphorylase having improved thermostability as described above, it becomes possible to considerably improve thermostability of natural sucrose phosphorylase. In addition, the expressed sucrose phosphorylase having improved thermostability can be simply purified utilizing the thermostability thereof. In brief, by heat-treating a cell extract containing sucrose phosphorylase having improved thermostability at about 60° C., contaminating enzymes are insolubilized. By centrifuging the insolubilized substances to remove them, and performing dialysis treatment, purified sucrose phosphorylase having improved thermostability is obtained.

In a preferred embodiment, sucrose phosphorylase can be heated in the presence of sucrose (typically about 4% to about 30%, preferably about 8% to about 30%, more preferably about 8% to about 25%) in any purification step. The temperature of a solution in this heating step is preferably a temperature at which when this solution is heated for 30 minutes, 50% or more, more preferably 80% or more, of the activity of the sucrose phosphorylase contained in the solution before heating remains in the solution. This temperature is preferably about 50° C. to about 70° C., more preferably about 55° C. to about 65° C. In the case of a *S. mutant*-derived sucrose phosphorylase having improved thermostability, for example, this temperature is preferably about 50° C. to about 70° C., more preferably about 55° C. to about 65° C. When heating is carried out, by taking the reaction temperature into consideration, the heating time can be set at any term as long as the activity of sucrose phosphorylase is not significantly deteriorated. The heating time is typically about 10 minutes to about 90 minutes, more preferably about 30 minutes to about 60 minutes.

(3. Sucrose Phosphorylase Having Improved Thermostability)

(3.1 Properties of Sucrose Phosphorylase Having Improved Thermostability)

The enzyme according to the present invention obtained by a method such as those described above has an amino acid residue which is different from an amino acid residue of the natural sucrose phosphorylase in at least one position selected from the group consisting of a position corresponding to position 14, a position corresponding to position 29 and a position corresponding to position 44 in motif sequence 1; a position corresponding to position 7, a position corresponding to position 19, a position corresponding to position 23 and a position corresponding to position 39 in motif sequence 2; and a position corresponding to position 19 in motif sequence 3 (or in at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249) in the amino acid sequence of SEQ ID NO: 2), wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating.

The enzymes of the present invention have an amino acid residue which is different from those of the natural sucrose phosphorylase in preferably at least 2 positions, more preferably at least 3 positions, still more preferably at least 4 positions, further more preferably at least 5 positions, even more preferably at least 6 positions, especially more preferably at least 7 positions, most preferably all of 8 positions, selected from the group consisting of a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3 (or a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249), in the amino acid sequence of SEQ ID NO: 2). For example, an example of the amino acid sequence having substitutions in all of the 8 positions in the sucrose phosphorylase having the amino acid sequence of SEQ ID NO: 2 is set forth in SEQ ID NO: 22, and the base sequence encoding this amino acid sequence is set forth in SEQ ID NO: 21. By these substitutions, the substituted sucrose phosphorylase has improved thermostability as compared with that of the sucrose phosphorylase before substitution. The sucrose phosphorylase having improved thermostability of the present invention may contain an amino acid sequence having not only the substitution of amino acid residues at these positions but also the deletion, substation or addition of one or several amino acid to the amino acid sequence of a natural sucrose phosphorylase.

It is thought that the aforementioned 8 positions of natural sucrose phosphorylase interact with surrounding amino acids in the steric structure of sucrose phosphorylase to form a steric partial structure which destabilizes the enzyme. By changing a residue at these positions to another amino acid residue, thermostability is improved. In addition, since residues at these positions steric-structurally interact with surrounding amino acid residues, substitution of the amino acid residues has important significant effects. For example, in the case of *Streptococcus mutans*-derived sucrose phosphorylase, substitution of T at a position of T47 with other residues has important significant consequences. In addition, for example, in *Lactobacillus acidophilus*-derived sucrose phosphorylase, an amino acid at a position corresponding to position 14 in motif sequence 1 (or T47) is N, and substitution of N with other amino acids has important significant effects. For example, if N is substituted with T, the substituted sequence will be similar to that of the *Streptococcus mutans*-derived sucrose phosphorylase, and improvement in thermostability can be seen in this sequence as well.

In the enzyme according to the present invention, the amino acid residue at a position corresponding to position 14 in motif sequence 1 (or a position corresponding to T47) can be an amino acid other than the amino acid residue found in the natural sucrose phosphorylase. The amino acid residue at a position corresponding to position 14 in motif sequence 1 (or a position corresponding to T47) is most preferably serine. In another embodiment, the amino acid residue at a position corresponding to position 14 in motif sequence 1 (or a position corresponding to T47) is particularly preferably serine or isoleucine, and most preferably isoleucine.

In the enzyme of the present invention, the amino acid residue at a position corresponding to position 29 in motif sequence 1 (or the amino acid residue in a position corresponding to S62) can be an amino acid other than the amino acid residue found in the natural sucrose phosphorylase. The amino acid residue at a position corresponding to position 29 in motif sequence 1 (or a position corresponding to S62) is most preferably proline. In another embodiment, the amino acid residue at a position corresponding to position 29 in motif sequence 1 (or a position corresponding to S62) is particularly preferably proline, alanine or lysine, and most preferably alanine.

In the enzyme of the present invention, the amino acid residue at a position corresponding to position 44 in motif sequence 1 (or a position corresponding to Y77) can be an amino acid other than the amino acid residue found in the natural sucrose phosphorylase. The amino acid residue at a position corresponding to position 44 in motif sequence 1 (or a position corresponding to Y77) is particularly preferably histidine or tryptophan, and most preferably histidine. In another embodiment, the amino acid residue at a position corresponding to position 44 in motif sequence 1 (or a position corresponding to Y77) is particularly preferably histidine or arginine, and most preferably arginine.

In the enzyme according to the present invention, the amino acid residue at a position corresponding to position 7 in motif sequence 2 (or a position corresponding to V128) can be an amino acid other than the amino acid residue found in the natural sucrose phosphorylase. The amino acid residue at a position corresponding to position 7 in motif sequence 2 (or a position corresponding to V128) is most preferably leucine. In another embodiment, the amino acid residue in a position corresponding to position 7 in motif sequence 2 (or a position corresponding to V128) is particularly preferably leucine or isoleucine, and most preferably isoleucine.

In the enzyme according to the present invention, the amino acid residue in a position corresponding to position 19 at motif sequence 2 (or a position corresponding to K140) can be an amino acid other than the amino acid residue found in the natural sucrose phosphorylase. The amino acid residue at a position corresponding to position 19 in motif sequence 2 (or a position corresponding to K140) is particularly preferably methionine or cysteine, and most preferably methionine. In another embodiment, the amino acid residue at a position corresponding to position 19 in motif sequence 2 (or a position corresponding to K140) is more preferably methionine, cysteine, phenylalanine, isoleucine, valine or tyrosine, still more preferably methionine, cysteine, phenylalanine, valine or tyrosine, further more preferably cysteine, phenylalanine, valine or tyrosine, even more preferably phenylalanine, valine or tyrosine, even more preferably valine or tyrosine, and most preferably tyrosine.

In the enzyme according to the present invention, the amino acid residue at a position corresponding to position 23 in motif sequence 2 (or a position corresponding to Q144) can be an amino acid other than the amino acid residue found in the natural sucrose phosphorylase. The amino acid residue at a position corresponding to position 23 in motif sequence 2 (or a position corresponding to Q144) is particularly preferably arginine or lysine, and most preferably arginine. In another embodiment, the amino acid residue in a position corresponding to position 23 in motif sequence 2 (or a position corresponding to Q144) is preferably arginine, histidine, isoleucine, lysine or valine, more preferably histidine, isoleucine, lysine or valine, still more preferably histidine, isoleucine or valine, further more preferably histidine or isoleucine, and most preferably histidine.

In the enzyme according to the present invention, the amino acid residue at a position corresponding to position 34 in motif sequence 2 (or a position corresponding to N155) can be an amino acid other than the amino acid residue found in the natural sucrose phosphorylase. The amino acid residue in a position corresponding to position 34 in motif sequence 2 (or a position corresponding to N155) is particularly preferably serine or threonine, and most preferably serine.

In the enzyme according to the present invention, the amino acid residue at a position corresponding to position 19 in motif sequence 3 (or a position corresponding to D249) can be an amino acid other than the amino acid residue found in the natural sucrose phosphorylase. The amino acid residue at a position corresponding to position 19 in motif sequence 3 (or a position corresponding to D249) is particularly preferably glycine or alanine, and most preferably glycine. The amino acid residue at a position corresponding to position 19 in motif sequence 3 (or a position corresponding to D249) is more preferably glycine, cysteine, histidine, lysine, leucine, asparagine, proline, glutamine, arginine or serine, still more preferably glycine, histidine or asparagine, further more preferably glycine or asparagine, and most preferably glycine.

In a method according to the present invention, to prepare the sucrose phosphorylase having improved thermostability, amino acid substitution, addition, deletion or modification can be carried out, in addition to the objective modification in the present invention (a substitution such that the sucrose phosphorylase having improved thermostability has a different amino acid residue from the amino acid residue of the natural sucrose phosphorylase in at least one position selected from the group consisting of a position corresponding to position 14, a position corresponding to position 29 and a position corresponding to position 44 in motif sequence 1; a position corresponding to position 7, a position corresponding to position 19, a position corresponding to position 23 and a position corresponding to position 34 in motif sequence 2; and a position corresponding to position 19 in motif sequence 3 (or in at least one position selected from the group consisting of a position corresponding to threonine at position 47 (T47), a position corresponding to serine at position 62 (S62), a position corresponding to tyrosine at position 77 (Y77), a position corresponding to valine at position 128 (V128), a position corresponding to lysine at position 140 (K140), a position corresponding to glutamine at position 144 (Q144), a position corresponding to asparagine at position 155 (N155), and a position corresponding to aspartic acid at position 249 (D249), in the amino acid sequence of SEQ ID NO: 2).

An amino acid substitution refers to replacement of one amino acid by another amino acid. Any number of amino acids in any positions can be substituted as long as the resulting sucrose phosphorylase has substantially the same enzyme activity as an enzyme activity of the natural sucrose phosphorylase. For example, preferably 1 to 30, more preferably 1 to 20, still more preferably 1 to 10, especially preferably 1 to 5, and most preferably 1 to 3 substitutions are possible. This amino acid substitution may be interspersed with one residue, or substitutions of 2 or more residues may be contiguous. Particularly, when a substitution is carried out at the N terminus or C terminus, since this substitution has less influence on an activity compared with substitutions at other positions, more amino acid residues than in substitution at other positions may be substituted. Substitutions at the vicinity of a position at which objective mutation are created (a position corresponding to T47, a position corresponding to S62, a position corresponding to Y77, a position corresponding to V128, a position corresponding to K140, a position corresponding to Q144, a position corresponding to N155, and a position corresponding to D249 in the amino acid sequence of SEQ ID NO: 2) may influence thermostability, and are thus not very preferable.

An amino acid addition refers to insertion of one or more amino acids, for example, 1 to 30, more preferably 1 to 20, still more preferably 1 to 10, even more preferably 1 to 5, and most preferably 1 to 3 amino acids into some place in the original amino acid sequence. An amino acid addition may also be interspersed with one residue, or additions of 2 or more residues may be contiguous. Particularly, when an amino acid is added at the N-terminus or C-terminus, since this addition has less influence on an activity compared with additions at other positions, more amino acid residues than in addition at other positions may be added. For example, 1 to 100, more preferably 1 to 50, still more preferably 1 to 30, further more preferably 5 to 30, most preferably 5 to 10 amino acid residues may be added. Additions at the vicinity of the positions at which objective mutation are created may influence thermostability, and are thus not very preferable.

An amino acid deletion refers to deletion of one or more amino acids, for example, 1 to 30, more preferably 1 to 10, especially preferably 1 to 5, and most preferably 1 to 3 amino acids from the original amino acid sequence. The amino acid deletion may also be interspersed with one residue, or deletions of 2 or more residues may be contiguous. Particularly, when a deletion is carried out at the N-terminus or C-terminus, since this deletion has less influence on an activity compared with deletions at other positions, more amino acid residues than in substitution at other positions may be deleted. Deletions at the vicinity of a position at which objective mutation are created may influence thermostability, and are thus not very preferable.

Examples of amino acid modification include but are not limited to amidation, carboxylation, sulfation, halogenation, alkylation, glycosylation, phosphorylation, hydroxylation, and acylation (e.g. acetylation). The sucrose phosphorylase having improved thermostability of the present invention may be synthesized by a peptide synthesis method and, in such the case, an amino acid to be substituted or added may be a natural amino acid, a non-natural amino acid or an amino acid analog. A natural amino acid is preferable.

The sucrose phosphorylase having improved thermostability of the present invention may be an enzyme analog having the same enzyme activity as sucrose phosphorylase. As used herein, a term "enzyme analog" refers to an entity which is a different compound from a natural enzyme, but has equivalent in at least one chemical function or biological function to that of a natural enzyme. Therefore, the enzyme analog includes an entity in which one or more amino acid analogs are added or substituted relative to the original natural enzyme. The enzyme analog has such an addition or substitution, that its function (e.g. sucrose phosphorylase activity) is substantially the same as, or better than, the function of the original natural enzyme. Such an enzyme analog can be prepared using techniques well-known in the art. Therefore, the enzyme analog can be a polymer containing an amino acid analog. In the present specification, the "enzyme" includes this enzyme analog unless otherwise indicated.

In the present specification, the "amino acid" may be a natural amino acid, a non-natural amino acid, a derivative amino acid, or an amino acid analog. A natural amino acid is preferable.

The term "natural amino acid" means an L-isomer of a natural amino acid. A natural amino acid is glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless otherwise is indicated, all amino acids referred in the present specification are in L form, and an embodiment using an amino acid in D form is also within the scope of the present invention.

The term "non-natural amino acid" means an amino acid which is not usually found in a protein in nature. Examples of the non-natural amino acid include norleucine, para-nitrophenylalanine, homophenylalanine, para-fluorophenylalanine, 3-amino-2-benzylpropionic acid, a D form or an N form of homoarginine, and D-phenylalanine.

The term "derivative amino acid" refers to an amino acid which is obtained by derivatizing an amino acid.

The term "amino acid analog" refers to a molecule which is not an amino acid, but is similar to an amino acid in physical properties and/or function. Examples of the amino acid analog include, for example, ethionine, canavanine, and 2-methylglutamine.

In the present specification, an amino acid can be referred by any of the generally known three letter symbol, and one letter symbol recommended by IUPAC-IUB Biochemical Nomenclature Commission. A nucleotide can be referred by a generally-accepted one letter code, similarly.

Sucrose phosphorylase having improved thermostability including modification due to substitution, addition or deletion of one or a few or more plural amino acids relative to an amino acid sequence of natural sucrose phosphorylase, in addition to the objective modification is within the scope of the present invention. Such a modification of amino acid other than objective modifications is preferably conservative modification, more preferably conservative substitution. In addition, it is considered that amino acid addition or deletion at the N-terminus or C-terminus of the natural sucrose phosphorylase has less influence on enzyme activity of the sucrose phosphorylase than substitution, addition or deletion at other regions. Therefore, an amino acid substitution, addition or deletion at the N-terminus or C-terminus is preferable. Such a sucrose phosphorylase having improved thermostability including substitution, addition or deletion of one or a few or more amino acid can be prepared according to the methods described in, for example, Molecular Cloning, A Laboratory Manual, Second Edition, Cold Spring Harbor Laboratory Press (1989), Current Protocols in Molecular Biology, Supplement 1-38, John Wiley & Sons (1987-1997), Nucleic Acids Research, 10, 6487 (1982), Proc. Natl. Acad. Sci., USA, 79, 6409 (1982), Gene, 34, 315 (1985), Nucleic Acids Research 13, 443 (1985), Proc. Natl. Acad. Sci. USA, 82, 488 (1985), Proc. Natl. Acad. Sci., USA, 81, 5662 (1984), Science, 224, 1431 (1984), PCT WO85/00817 (1985), Nature, 316, 601 (1985).

A sucrose phosphorylase having improved thermostability according to the present invention can be prepared by utilizing methods well-known in the art. For example, deletion, substitution or addition of an amino acid in the sucrose phosphorylase having improved thermostability of the present invention can be performed by site-directed mutagenesis which is a well-known technique. The technique of site-directed mutagenesis is well-known in the art. For example, see Nucl. Acid Research, Vol. 10, pp. 6487-6500 (1982).

In the present specification, the "substitution, addition or deletion of one or a few or more plural amino acids" or the "substitution, addition or deletion of at least one amino acid", when used regarding a modification other than objective modification of sucrose phosphorylase having improved thermostability, refers to a number of substitutions, additions or deletions, to such a degree that the enzyme activity of sucrose phosphorylase is not lost, preferably, the enzyme activity becomes equivalent or superior over a standard (e.g. natural sucrose phosphorylase). Those skilled in the art can easily select sucrose phosphorylase having improved thermostability having the desired nature. Alternatively, objective sucrose phosphorylase having improved thermostability may be directly chemically synthesized. Such chemical synthesis method is well-known in the art.

The thus prepared sucrose phosphorylase having improved thermostability of the present invention has preferably about 40%, more preferably about 45%, more preferably about 50%, more preferably about 55%, more preferably about 60%, more preferably about 65%, more preferably about 70%, more preferably about 75%, more preferably about 80%, more preferably about 85%, more preferably about 90%, more preferably about 95%, and most preferably about 99% identity to the amino acid sequence of first (for example, natural) sucrose phosphorylase (preferably, *Streptococcus mutans*-derived or *Streptococcus pneumoniae*-derived sucrose phosphorylase).

Upon design of the aforementioned modification, the hydrophobicity index of an amino acid can be considered. Significance of a hydrophobic amino acid index upon impartation interacting biological function to a protein is generally recognized in the art (Kyte. J and Doolittle, R. F., J. Mol. Biol. 157 (1): 105-132, 1982). The hydrophobic nature of an amino acid contributes to the secondary structure of a produced protein and, then, defines interaction between the protein and other molecule (e.g. enzyme, substrate, receptor, DNA, antibody, antigen and the like). An amino acid is assigned a hydrophobicity index based on hydrophobicity and a nature of a charge thereof. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well-known in the art to substitute a certain amino acid with another amino acid having a similar hydrophobicity index, thereby, a protein still having substantially similar biological functions (e.g. protein substantially equivalent in enzyme activity) can be produced. In such an amino acid substitution, a hydrophobicity index is preferably within ±2, more preferably within ±1, further preferably within ±0.5. It is understood in the art that such the substitution of an amino acid based on hydrophobicity is efficient. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted with another amino acid which has a similar hydrophilicity index, and can still provide a biological equivalent. In such the amino acid substitution, the hydrophilicity index is preferably within ±2, more preferably within ±1, and further preferably within ±0.5.

In the present invention, "conservative substitution" refers to substitution in which a hydrophilicity index or/and a hydrophobicity index are similar as described above, between the original amino acid and an amino acid to be substituted, in amino acid substitution. Examples of conservative substitution are well-known to those skilled in the art, and include, but are not limited to substitution among the following each group, for example: arginine and lysine; glutamic acid and aspartic acid; serine and threonine; glutamine and asparagines; and valine, leucine, and isoleucine.

(3.2 Method of Assessing Thermostability)

The sucrose phosphorylase having improved thermostability of the present invention has one characteristic, in that enzyme activity of sucrose phosphorylase having improved thermostability at 37° C., after it is heated in a 20 mM Tris buffer (pH 7.0) at 55° C. for 20 minutes, is 20% or more of enzyme activity of the sucrose phosphorylase having improved thermostability at 37° C., before heating. Enzyme activity of the sucrose phosphorylase having improved thermostability at 37° C., after heating the sucrose phosphorylase having improved thermostability in a 20 mM Tris buffer (pH 7.0) at 55° C. for 20 minutes, is preferably about 20% or more, more preferably about 30% or more, more preferably about 40% or more, more preferably about 50% or more, more preferably about 55% or more, more preferably about 60% or more, further preferably about 65% or more, further preferably about 70% or more, particularly preferably about 80% or more, and most preferably about 90% or more of the enzyme activity of the sucrose phosphorylase having improved thermostability at 37° C. before the heating.

Enzyme activity of sucrose phosphorylase having improved thermostability at 37° C., after heating the sucrose phosphorylase having improved thermostability in a 20 mM Tris buffer (pH 7.0) at 57° C. for 20 minutes is preferably about 10% or more, more preferably about 20% or more, more preferably about 30% or more, more preferably about 40% or more, more preferably about 50% or more, more preferably about 55% or more, further preferably about 60% or more, even more preferably about 65% or more, even further preferably about 70% or more, particularly preferably about 80% or more, and most preferably about 90% or more of the enzyme activity at 37° C. of the sucrose phosphorylase having improved thermostability before the heating.

Enzyme activity of sucrose phosphorylase having improved thermostability at 37° C., after heating the sucrose phosphorylase having improved thermostability in a 20 mM Tris buffer (pH 7.0) at 60° C. for 20 minutes is preferably about 5% or more, more preferably about 10% or more, more preferably about 15% or more, more preferably about 20% or more, more preferably about 25% or more, more preferably about 30% or more, further preferably about 35% or more, even more preferably about 40% or more, even further preferably about 50% or more, particularly preferably about 60% or more, and most preferably about 70% or more of the enzyme activity at 37° C. of the sucrose phosphorylase having improved thermostability before the heating.

Enzyme activity of sucrose phosphorylase having improved thermostability at 37° C., after heating the sucrose phosphorylase having improved thermostability in a 20 mM Tris buffer (pH 7.0) at 65° C. for 20 minutes is more preferably about 10% or more, more preferably about 20% or more, more preferably about 30% or more, more preferably about 40% or more, more preferably about 50% or more, more preferably about 55% or more, further preferably about 60% or more, even more preferably about 65% or more, even further preferably about 70% or more, particularly preferably about 80% or more, and most preferably about 90% or more of the enzyme activity at 37° C. of the sucrose phosphorylase having improved thermostability before the heating. In this specification, a concentration of sucrose is calculated in weight/volume, that is, (sucrose weight)×100/(solution volume).

(3.2.1 Method of Measuring Sucrose Phosphorylase (SP) Activity)

The activity unit of sucrose phosphorylase can be measured by any method known in the art. For example, it can be determined by a method described in Example 1.7 described later.

(3.2.2 Method of Measuring Thermostability)

Thermostability can be measured according to the following procedures:

(i) 2.5 to 3.5 U/ml enzyme solution (in 20 mM Tris buffer (pH 7.0)) containing or not containing 20% sucrose is incubated at 55° C., 57° C., 60° C. or 65° C. for 20 minutes.

(ii) After 20 minutes, the enzyme is removed and then cooled on ice for 10 minutes.

(iii) The enzyme solution in (ii) is measured for its enzyme activity at 37° C. according to the method of measuring SP activity. The ratio of the enzyme activity $A_{after}$ of the sucrose phosphorylase having improved thermostability at 37° C., after heating the sucrose phosphorylase having improved thermostability in 20 mM Tris buffer (pH 7.0) at 55° C. for 20 minutes, to enzyme activity $A_{before}$ of the sucrose phosphorylase having improved thermostability at 37° C., before the heating, is calculated from following: $(A_{after})/(A_{before}) \times 100$ (%). The ratio of enzyme activity $A_{after}$ of the sucrose phosphorylase having improved thermostability after heating, to the enzyme activity $A_{before}$ of the sucrose phosphorylase having improved thermostability before heating is also referred to as remaining activity.

(3.3 Yield of Amylose Under High-Temperature Conditions)

Using the sucrose phosphorylase having improved thermostability of the present invention, amylose can be synthesized under high-temperature conditions. In the present specification, the phrase "amylose can be synthesized under high-temperature conditions" refers to that, when amylose is synthesized by incubation at 50° C. for 18 hours by using 58.5 mM sucrose, 1 mM maltotetraose, 10 mM inorganic phosphoric acid, 1 U/ml *Thermus aquaticus*-derived α-glucan phosphorylase (prepared according to Example 2.2 below) and 1 U/ml sucrose phosphorylase having improved, thermostability the yield of the amylose synthesized is 50% or more. When amylose is synthesized under this condition, the yield of amylose is preferably 60% or more, more preferably 70% or more, still more preferably 80% or more, and most preferably 90% or more.

(3.4 Specific Activity of the Sucrose Phosphorylase Having Improved Thermostability of the Present Invention)

The sucrose phosphorylase having improved thermostability of the present invention has high specific activity at high temperatures (preferably 55° C.). The specific activity refers to activity per weight of sucrose phosphorylase (U/g).

The specific activity of the sucrose phosphorylase having improved thermostability of the present invention, when reacted at 55° C. for 15 minutes in 250 mM phosphate buffer (pH 7.0) containing 5% sucrose, is preferably at least 20 U/mg, more preferably at least 0.30 U/mg, even more preferably at least 40 U/mg, even more preferably at least 50 U/mg, even more preferably at least 60 U/mg, even more preferably at least 70 U/mg, even more preferably at least 80 U/mg, even more preferably at least 90 U/mg, even more preferably at least 100 U/mg, even more preferably at least 110 U/mg, even more preferably at least 120 U/mg, even more preferably at least 130 U/mg, even more preferably at least 140 U/mg, even more preferably at least 150 U/mg, especially preferably at least 160 U/mg, and most preferably at least 180 U/mg.

The SP enzyme having improved thermostability of the present invention preferably has higher specific activity at high temperatures and higher remaining activity at high temperatures compared with those of the natural SP enzyme.

(4. Method for Producing α-Glucan Using the Enzyme of the Present Invention)

The sucrose phosphorylase having improved thermostability of the present invention can be advantageously used in a method of producing an α-glucan. A method of producing a glucan using the sucrose phosphorylase having improved thermostability of the present invention can be any method of producing an α-glucan known in the art, but it is preferable to use the present sucrose phosphorylase in a method (also referred to as SP-GP method) of reacting sucrose phosphorylase and α-glucan phosphorylase on sucrose and a primer at the same time. The SP-GP method has an advantage that a linear glucan can be produced using an inexpensive substrate.

A method of synthesizing an α-glucan of the preset invention includes reacting a reaction solution containing the sucrose phosphorylase having improved thermostability according to the present invention, an α-glucan phosphorylase, sucrose, a primer, and inorganic phosphoric acid or glucose-1-phosphate, to produce an α-glucan.

In the present specification, the "α-glucan" refers to a saccharide containing D-glucose as a constituent unit, and having at least two saccharide units or more of a saccharide unit linked with an α-1,4-glucoside bond. An α-glucan can be a linear, branched or cyclic molecule. A linear glucan has the same meaning as that of α-1,4-glucan. In a linear α-glucan, saccharide units are linked only with an α-1,4-glucoside bond. A α-glucan containing one or more α-1,6-glucoside bonds is a branched α-glucan. An α-glucan preferably contains a linear section to some extent. A linear α-glucan having no branching is more preferable.

It is preferably that an α-glucan has a small number of branches (i.e. the number of α-1,6-glucoside bonds) in some cases. In such the case, the number of branches is typically 0 to 10000, preferably 0 to 1000, more preferably 0 to 500, further preferably 0 to 100, further preferably 0 to 50, further preferably 0 to 25, further preferably 0.

In the glucan of the present invention, the ratio of the number of α-1,4-glucoside bonds relative to the number of α-1,6-glucoside bonds letting α-1,6-glucoside bond to be 1, is preferably 1 to 10000, more preferably 10 to 5000, further preferably 50 to 1000, further preferably 100 to 500.

α-1,6-glucoside bond may be distributed in an α-glucan randomly, or may be distributed uniformly. A distribution to such an extent that a linear part of 5 or more of saccharide units is formed in an α-glucan is preferable.

A glucan may be constructed only of D-glucose, or may be a derivative modified to such an extent that the nature of such an α-glucan is not deteriorated. It is preferable that the α-glucan is not modified.

An α-glucan has a molecular weight of typically about $8 \times 10^3$ or more, preferably about $1 \times 10^4$ or more, more preferably about $5 \times 10^4$ or more, further preferably about $1 \times 10^5$ or more, further preferably about $6 \times 10^5$ or more. An α-glucan has a molecular weight of typically about $1 \times 10^8$ or less, preferably about $1 \times 10^7$ or less, more preferably about $5 \times 10^6$ or less, further preferably about $1 \times 10^6$ or less.

Those skilled in the art easily understands that an α-glucan having a desired molecular weight is obtained by appropriately selecting an amount of a substrate, an amount of an enzyme, a reaction time and the like used in the production method of the present invention.

The SP-GP method having excellent productivity is described in International Publication WO 02/097107 pamphlet.

In the production method of the present invention, for example, sucrose phosphorylase having improved thermostability, α-glucanphosphorylase, sucrose, a primer, inorganic phosphoric acid or glucose-1-phosphate, a buffer, and a solvent dissolving it are used as main materials. Usually, these materials are all added at reaction initiation, and any material among them may be additionally added during the reaction. In the production method of the present invention, if necessary, an enzyme selected from the group consisting of a debranching enzyme, a branching enzyme, 4-α-glucanotransferase and glycogen debranching enzyme can be used. An enzyme selected from the group consisting of: a debranching enzyme, a branching enzyme, 4-α-glucan transferase and a glycogen debranching enzyme may be added to a reaction solution from beginning of the production method of the present invention, or may be added to a reaction solution midway, depending upon the desired structure of α-glucan.

The amount of sucrose phosphorylase contained in a solution when the reaction is initiated is typically about 0.05 to 1,000 U/grams sucrose, preferably about 0.1 to 500 U/grams sucrose, more preferably about 0.5 to 100 U/grams sucrose relative to sucrose in the solution when the reaction is initiated. If the weight of sucrose phosphorylase is too large, the enzyme denatured during the reaction may be easily aggregated. If the amount of sucrose phosphorylase used is too small, the yield of α-glucan may be lowered.

In the present specification, "α-glucan phosphorylase" means an enzyme having α-glucan phosphorylase activity. α-glucan phosphorylase is classified into EC2.4.1.1. α-glucan phosphorylase activity refers to the activity of catalyzing a reaction making glucose-1-phosphate and a partial degradation product of α-1,4-glucan from inorganic phosphoric acid and α-1,4-glucan, or a reverse reaction thereof. α-glucan phosphorylase is called phosphorylase, starch phosphorylase, glycogen phosphorylase, maltodextrin phosphorylase, and the like, in some cases. α-glucan phosphorylase can also catalyze a α-1,4-glucan synthesis reaction which is the reverse reaction of phosphorolysis. In which direction any particular reaction progresses depend on the amount of a substrate. In vivo, since the amount of inorganic phosphoric acid is large, the reaction of α-glucan phosphorylase proceeds towards the direction of phosphorolysis. When the amount of inorganic phosphoric acid is small, the reaction proceeds towards the synthesis of α-1,4-glucan.

It seems that all known α-glucan phosphorylases need pyridoxal 5'-phosphate for activation, and share a similar catalytic mechanism. Although enzymes derived from different origins are different with respect to preference of substrate and form of regulation, all α-glucan phosphorylases belong to a large group including many α-glucan phosphorylases. This large group includes glycogen phosphorylase derived from bacteria, yeast and animals, starch phosphorylase derived from plants, and maltooligosaccharide phosphorylase derived from bacteria.

It has been reported that a minimum primer molecule for an α-glucan synthesis reaction of α-glucan phosphorylase is maltotetraose. It has been also reported that a minimum substrate effective for an α-glucan degradation reaction is maltopentaose. Generally, it had been thought that these are characteristics common to α-glucan phosphorylases. However, in recent years, it has been reported that α-glucan phosphorylase derived from *Thermus thermophilus* and α-glucan phosphorylase derived from *Thermococcus litoralis* have different substrate specificity from that of other α-glucan phosphorylases. Regarding these α-glucan phosphorylases, a minimum primer for α-glucan synthesis is maltotriose, and a minimum substrate for α-glucan degradation is maltotetraose.

It is thought that α-glucan phosphorylase is ubiquitously present in various plants, animals and microorganisms which can store starch or glycogen.

Examples of a plant producing α-glucan phosphorylase include root and tuber crops such as potatoes (also referred to as Irish potato), sweet potatoes, yam, taro, and cassava; vegetables such as cabbage, and spinach; cereals such as corn, rice, wheat, barley, rye, and foxtail millet; beans such as Fava beans, peas, soybeans, adzuki beans, and mottled kidney beans; experimental plants such as *Arabidopsis thaliana*; Citrus; algae; and the like.

Examples of animals producing α-glucan phosphorylase include mammals such as humans, rabbits, rats and swine.

Examples of microorganisms producing α-glucan phosphorylase include *Thermus aquaticus, Bacillus stearothermophilus, E. coli* and the like An organism-producing α-glucan phosphorylase is not limited to the these examples. The α-glucan phosphorylase may be a natural α-glucan phosphorylase or an α-glucan phosphorylase having improved thermostability which has improved its thermostability by introducing a mutation into a natural α-glucan phosphorylase.

It is preferable that an α-glucan phosphorylase used in the method of the present invention is derived from a plant or animal, and is more preferably derived from a plant. Generally, natural α-glucan phosphorylase derived from a plant has the ability to synthesize amylose having a high molecular weight. However, the thermostability of these α-glucan phosphorylases is low. For this reason, they cannot catalyze reactions at high temperatures (e.g. about 60° C. or higher). For this reason, when a reaction is performed at about 30° C. to about 40° C., which is the optimal reaction temperature of GP derived from potato, the problem of contamination with various microbes or aging of the α-glucan arises, and α-glucan or G-1-P can not be effectively produced.

An α-glucan phosphorylase can be derived from any organism producing an α-glucan phosphorylase. An α-glucan phosphorylase preferably has a certain thermostability. Higher thermostability of an α-glucan phosphorylase is more preferable. For example, it is preferable that enzyme activity of an α-glucan phosphorylase at 37° C., after heating the sucrose phosphorylase having improved thermostability in a 20 mM Tris buffer (pH 7.0) at 60° C. for 10 minutes, is 20% or more of the enzyme activity of the α-glucan phosphorylase at 37° C. before heating.

An α-glucan phosphorylase may be a natural α-glucan phosphorylase, or may be a α-glucan phosphorylase having improved thermostability which have a mutation introduced in a specific position to improve thermostability. Such position can be at least one position selected from the group consisting of: a position corresponding to position 4 in GP motif sequence 1L: H-A-E-F-T-P-V-F-S or a position corresponding to position 4 in GP motif sequence 1H: H-A-Q-Y-S-P-H-F-S; a position corresponding to position 4 in GP motif sequence 2: A-L-G-N-G-G-L-G; and a position corresponding to position 7 in GP motif sequence 3L: R-I-V-K-F-I-T-D-V; or a position corresponding to position 7 in GP motif sequence 3H: R-1-V-K-L-V-N-D-V (or a position corresponding to phenylalanine at position 39 (F39), a position corresponding to asparagine at position 135 (N135) and a position corresponding to threonine at position 706 (T706) in a mature amino acid sequence of natural potato type-L α-glucan phosphorylase). These specific positions in α-glucan phosphorylase can be determined by using multiple alignment in the same manner as for SP. Positions corresponding to the specific positions in the GP motif sequences can be determined by multiple alignment of GENETYX-WIN Ver. 4.0 (Genetics Co., Ltd.) under the conditions described above, or can be determined by conducting maximum matching under conditions of Matches=−1; Mismatches=1; Gaps=0; and *N+=2.

An amino acid residue at a position corresponding to position 4 in the GP motif sequence 1L or 1H, or to F39 is preferably an aliphatic amino acid or a heterocyclic amino acid, more preferably an aliphatic amino acid, particularly preferably a branched amino acid (i.e. valine, leucine or isoleucine), specially preferably isoleucine or leucine, most preferably leucine.

An amino acid residue at a position corresponding to position 4 in the GP motif sequence 2 or to N135 is preferably an aliphatic amino acid or a heterocyclic amino acid, more preferably alanine, cysteine, aspartic acid, glutamic acid, glycine, histidine, isoleucine, leucine, methionine, phenylalanine, serine, threonine, valine or tyrosine, particularly preferably cysteine, glycine, serine or valine.

An amino acid residue at a position corresponding to position 7 in the GP motif sequence 3L or 3H, or to T706 is preferably an aliphatic amino acid, more preferably a branched amino acid (i.e. valine, leucine or isoleucine) or a sulfur-containing amino acid (i.e. cysteine, cystine, methionine), particularly preferably cysteine, isoleucine, leucine, valine or tryptophan, particularly preferably cysteine, isoleucine, leucine or valine, most preferably isoleucine.

An α-glucan phosphorylase is preferably modified in all of these 3 positions.

An α-glucan phosphorylase is preferably derived from potato, sweet potato, Fava bean, *Arabidopsis thaliana*, spinach, corn, rice, wheat or a citrus, is more preferably derived from potato, sweet potato, Fava bean, *Arabidopsis thaliana*, spinach, corn or rice, and is most preferably derived from potato. It is preferable that an α-glucan phosphorylase is derived from a type L α-glucan phosphorylase. An α-glucan phosphorylase is preferably derived from an α-glucan phosphorylase of type L, L2 or H derived from potato, type L or H derived from sweet potato, type L or H derived from Fava bean, type L or H derived from *Arabidopsis thaliana*, type L derived from spinach, type L derived from corn, type L or H derived from rice, type H derived from wheat, or type H derived from a citrus, is more preferably derived from an α-glucan phosphorylase of type L or L2 derived from potato, type L derived from sweet potato, type L derived from Fava bean, type L derived from *Arabidopsis thaliana*, type L derived from spinach, type L derived from corn, or type L derived from rice, is more preferably derived from an α-glucan phosphorylase of type L derived from potato or type L derived from *Arabidopsis thaliana*, and is most preferably derived from an α-glucan phosphorylase of type L derived from potato. An α-glucan phosphorylase has preferably improved thermostability.

An α-glucan phosphorylase used in the method of the present invention can be prepared for example in the following manner. Firstly, a microorganism (for example, bacterium, fungus and the like) producing an α-glucan phosphorylase is cultured. This microorganism may be a microorganism directly producing α-glucan phosphorylase. Alternatively, a gene encoding an α-glucan phosphorylase is cloned, a microorganism (for example, bacterium, fungus and the like) advantageous to expression of α-glucan phosphorylase is genetically recombined with the obtained gene to produce a recombinant microorganism, and the α-glucan phosphorylase may be obtained from the obtained microorganisms. Alternatively, the obtained gene is modified to contain modifications at the specific amino acid positions such as those described above, then a microorganism (for example, bacterium, fungus and the like) advantageous to expression of α-glucan phosphorylase is genetically recombined with the modified gene to produce a recombinant microorganism, and an α-glucan phosphorylase having improved thermostability may be obtained from the obtained microorganism. For example, a method for producing a recombinant potato α-glucan phosphorylase obtained by genetic recombination of *Escherichia coli* with a potato derived α-glucan phosphorylase gene is described in International Publication No. 02/097107 pamphlet.

A microorganism used for genetic recombination with an α-glucan phosphorylase gene can be easily selected, taking various conditions such as ease of expression of α-glucan phosphorylase, ease of culturing, growth rate, and safety into consideration. Since it is preferable that α-glucan phosphorylase does not contain amylase as a contaminant, it is preferable to use a microorganism (for example, bacterium, fungus and the like) which does not produce amylase or produces amylase only at a low level in the genetic recombination. It is preferable to use mesophilic microorganisms such as *Escherichia coli* and *Bacillus subtilis* in the genetic recombination for an α-glucan phosphorylase. α-Glucan phosphorylase produced by a microorganism (for example, bacterium, fungus and the like) which does not produce amylase or produces amylase only at a low level substantially does not contain amylase, and thus is preferably used in the method of the present invention.

The gene encoding a first (for example, natural) α-glucan phosphorylase can be modified by methods known in the art in order to change amino acid residues at a specific position contributing to thermostability. Examples of such modification methods include, for example, site-directed mutagenesis, mutagenesis using a mutagen (treatment of a subject gene with a mutagenic agent such as nitrite, ultraviolet-ray treatment), or error prone PCR.

Genetic recombination of a microorganism (for example, bacterium, fungus and the like) with a cloned gene can be carried out by methods well known to those skilled in the art. When the cloned gene is used, the gene is preferably operably linked with a constitutive promoter or an inducible promoter. The terms "operably linked" refers to when a promoter and a gene are linked in such a manner as to allow the gene to be regulated by the promoter. When an inducible promoter is used, culture is preferably conducted under inducible conditions. Various inducible promoters are known to those skilled in the art.

Regarding a cloned gene, a base sequence encoding a signal peptide can be linked with the cloned gene such that α-glucan phosphorylase produced can be secreted into the outside of the microorganism. The base sequence encoding a signal peptide is known to those skilled in the art.

Those skilled in the art can suitably set conditions for culture of a microorganism (for example, bacterium, fungus and the like) to produce an α-glucan phosphorylase. Mediums suitable for culture of a microorganism, and inducing conditions suitable for each inducible promoter, are known to those skilled in the art.

After being cultured for a suitable term, an α-glucan phosphorylase is recovered from a culture. When a produced α-glucan phosphorylase is secreted into the outside of a microorganism, the α-glucan phosphorylase can be obtained in a supernatant by removing the microbial bodies by centrifugation. When α-glucan phosphorylase produced in a microorganism is not secreted into the outside of the microbial body, the microorganism is disrupted by treatment such as sonication, mechanical milling, and chemical disruption, to give a liquid containing disrupted cells.

In the method of the present invention, the liquid containing disrupted cells may be used without purification. Then, the liquid containing disrupted cells can be centrifuged, thereby removing cell debris, to give a supernatant. From the resulting supernatant, the enzyme of the present invention can be recovered by well known methods including ammonium sulfate precipitation or ethanol precipitation, acid extraction, anion or cation exchange chromatography, phosphocellulose chromatography, hydrophobic interaction chromatography, affinity chromatography, hydroxylapatite chromatography and lectin chromatography. The recovered product can be purified as necessary.

In a preferred embodiment, an α-glucan phosphorylase can be heated in any stage during the purification step. The temperature of the solution in this heating step is preferably a temperature at which when this solution is heated for 30 minutes, preferably 50% or more, more preferably 80% or more, of the activity of the α-glucan phosphorylase contained in the solution before heating, remains in the solution. This temperature is preferably about 50° C. to about 70° C., more preferably about 55° C. to about 65° C. In the case of potato-derived type-L α-glucan phosphorylase having improved thermostability, for example, this temperature is preferably about 50° C. to about 60° C. When heating is carried out, it is possible to set, by taking the reaction temperature into consideration, the heating time arbitrarily insofar as the activity of α-glucan phosphorylase is not significantly deteriorated. The heating time is typically about 10 minutes to about 90 minutes, more preferably about 30 minutes to about 60 minutes.

The amount of α-glucan phosphorylase contained in the solution when the reaction is initiated is typically about 0.05 to 1,000 U/grams sucrose, preferably about 0.1 to 500 U/grams sucrose, more preferably about 0.5 to 100 U/grams sucrose relative to sucrose in the solution when the reaction is initiated. If the weight of α-glucan phosphorylase is too large, the enzyme denatured during the reaction may be easily aggregated. If the amount of α-glucan phosphorylase used is too small, the yield of α-glucan may be lowered.

Sucrose is a disaccharide having a molecular weight of about 342, represented by $C_{12}H_{22}O_{11}$. Sucrose is present in all plants having photosynthetic ability. Sucrose may be isolated from a plant, or may be chemically synthesized. From the viewpoint of cost, it is preferable that sucrose is isolated from a plant. Examples of a plant containing a large amount of sucrose include sugarcane and sugar beet. Sugarcane juice contains about 20% sucrose. Sugar beet juice contains about 10 to 15% sucrose. Sucrose may be provided at any purification stage from the sap or juice of a sucrose containing plant, to purified sugar.

A sucrose phosphorylase having improved thermostability and an α-glucan phosphorylase used in the production method of the present invention can be used in a reaction, respectively, even when immobilized whether it is a purified enzyme or a crude enzyme, and a reaction format may be a batch format or a continuous format. As a method of immobilization, a carrier binding method (e.g. covalent binding method, ion binding method, or physical adsorbing method), a crosslinking method or an inclusion method (lattice type or microcapsule type) can be used.

Examples of a primer include maltooligosaccharide, amylose, amylopectin, glycogen, dextrin, pullulan, coupling sugar, starch, and a derivative thereof.

In the present specification, inorganic phosphoric acid refers to a substance which can donate a phosphate substrate in the reaction of SP. In the present specification, a phosphate substrate refers to a substance which is a raw material for the phosphate moiety of glucose-1-phosphate. It is thought that, in sucrose phosphorolysis which is catalyzed by sucrose phosphorylase, inorganic phosphoric acid acts as a substrate in a form of a phosphate ion. Since this substrate is conventionally called inorganic phosphoric acid in the art, this substrate is called inorganic phosphoric acid also in the preset specification. Inorganic phosphoric acid includes phosphoric acid and an inorganic salt of phosphoric acid. Usually, inorganic phosphoric acid is used in water containing a cation such as an alkali metal ion. In this case, since phosphoric acid, a phosphate salt and a phosphate ion are in an equilibrium state, it is not possible to discriminate between phosphoric acid and a phosphate salt. Therefore, for convenience, phosphoric acid and a phosphate salt are collectively called inorganic phosphoric acid. In the present invention, inorganic phosphoric acid is preferably any metal salt of phosphoric acid, more preferably an alkali metal salt of phosphoric acid. Preferable specific examples of inorganic phosphoric acid include sodium dihydrogen phosphate, disodium hydrogen phosphate, trisodium phosphate, potassium dihydrogen phosphate, dipotassium hydrogen phosphate, tripotassium phosphate, phosphoric acid ($H_3PO_4$), ammonium dihydrogen phosphate, and diammonium hydrogen phosphate.

Only one kind of, or a plurality of kinds of inorganic phosphoric acids may be contained in a SP-GP reaction system at reaction initiation.

Inorganic phosphoric acid can be provided, for example, by degrading a phosphoric acid condensate such as polyphosphoric acid (e.g. pyrophosphoric acid, triphosphoric acid and tetraphosphoric acid) or a salt thereof, by a physical, chemical or enzymatic reaction, and adding this to a reaction solution.

In the present specification, glucose-1-phosphate refers to glucose-1-phosphoric acid ($C_6H_{13}O_9P$) and a salt thereof. Glucose-1-phosphate is preferably any metal salt of glucose-1-phosphoric acid ($C_6H_{13}O_9P$) in a narrow sense, more preferably any alkali metal salt of glucose-1-phosphoric acid ($C_6H_{13}O_9P$). Preferable specific examples of glucose-1-phosphate include disodium glucose-1-phosphate, dipotassium glucose-1-phosphate, and glucose-1-phosphoric acid ($C_6H_{13}O_9P$). In the present specification, glucose-1-phosphate whose chemical formula is not drawn in a parenthesis indicates glucose-1-phosphate in a wide sense, that is, glucose-1-phosphoric acid ($C_6H_{13}O_9P$) in a narrow sense and a salt thereof.

Only one kind of, or a plurality of kinds of glucose-1-phosphates may be contained in a SP-GP reaction system, at reaction initiation.

In the method for producing an α-glucan according to the present invention, when a branch is generated in the product, such as when a starting material containing α-1,6-glucoside bond is used, a debranching enzyme can be used, if necessary.

A debranching enzyme which can be used in the present invention is an enzyme which can cut an α-1,6-glucoside bond. A debranching enzyme is classified into two of isoamylase (EC 3.2.1.68) which acts well on both of amylopectin and glycogen, and α-dextrin endo-1,6-α-glucosidase (also referred to as pullulanase) (EC3.2.1.41) which acts on amylopectin, glycogen and pullulan.

A debranching enzyme is present in microorganisms, bacteria, and plants. Examples of a microorganism producing a debranching enzyme include *Saccharomyces cerevisiae*, and *Chlamydomonas* sp. Examples of a bacterium producing a debranching enzyme include *Bacillus brevis, Bacillus acidopullulyticus, Bacillus macerans, Bacillus stearothermophilus, Bacillus circulans, Thermus aquaticus, Klebsiella pneumoniae, Thermoactinomyces thalpophilus, Thermoanaerobacter ethanolicus*, and *Pseudomonas amyloderamosa*. Examples of a plant producing a debranching enzyme include potato, sweet potato, corn, rice, wheat, barley, oat, and sugar beet. An organism producing a debranching enzyme is not limited to the above examples.

In the method according to the invention, when it is desired to generate a branch in the product, a branching enzyme can be used, if necessary.

A branching enzyme which can be used in the present invention is an enzyme which can transfer a part of an α-1,4-glucan chain to position 6 of a certain glucose residue in this α-1,4-glucan chain to make a branch. A branching enzyme is also called a 1,4-α-glucan branching enzyme, a branch making enzyme or a Q enzyme.

A branching enzyme is present in a microorganism, an animal, and a plant. Examples of a microorganism producing a branching enzyme include *Bacillus stearothermophilus, Bacillus subtilis, Bacillus caldolyticus, Bacillus lichecniformis, Bacillus amyloliquefaciens, Bacillus coagulans, Bacillus caldovelox, Bacillus thermocatenulatus, Bacillus smithii, Bacillus megaterium, Bacillus brevis, Alkalophillic Bacillus* sp., *Streptomyces coelicolor, Aquifex aeolicus, Synechosystis* sp., *E. coli, Agrobacterium tumefaceins, Thermus aquaticus, Rhodothermus obamensis, Neurospora crassa*, and yeast. Examples of an animal producing a branching enzyme include mammals such as human, rabbit, rat, and pig. Examples of plants producing a branching enzyme include algae; tuber and root crops such as potatoes, sweet potato, yam, and cassava; vegetables such as spinach; cereals such as corn, rice, wheat, barley, rye, and foxtail millet; and beans such as peas, soybeans, adzuki beans, and mottled kidney beans. An organism producing a branching enzyme is not limited to the above examples.

In the method according to the invention, when a cyclic structure is generated in the product, 4-α-glucanotransferase can be used, if necessary.

4-α-glucanotransferase which can be used in the present invention is also called a disproportionating enzyme, a D-enzyme, or amylomaltase, and is an enzyme which can catalyze a sugar transferring reaction (disproportionating reaction) of maltooligosaccharide. 4-α-glucanotransferase is an enzyme which transfers a glucosyl group, or a maltosyl or maltooligosyl unit from a non-reducing terminal of a donor molecule to a non-reducing terminal of an acceptor molecule. Therefore, an enzyme reaction leads to disproportion of a polymerization degree of maltooligosaccharide which was first given. When a donor molecule and an acceptor molecule are the same, an intramolecular transfer is caused and, as a result, a product having a cyclic structure is obtained.

4-α-glucanotransferase is present in microorganisms and plants. Examples of a microorganism producing 4-α-glucanotransferase include *Aquifex aeolicus, Streptococcus pneumoniae, Clostridium butylicum, Deinococcus radiodurans, Haemophilus influenzae, Mycobacterium tuberculosis, Thermococcus litralis, Thermotoga maritima, Thermotoga neapolitana, Chlamydia psittaci, Pyrococcus* sp., *Dictyoglomus thermophilum, Borrelia burgdorferi, Synechosystis* sp., *E. coli,* and *Thermus aquaticus*. Examples of plants producing 4-α-glucanotransferase include tuber and root crops such as potatoes, sweet potatoes, yam, and cassava; cereals such as corn, rice, and wheat; and beans such as peas and soybeans. An organism producing 4-α-glucanotransferase is not limited to the above examples.

In the method of the present invention, when a cyclic structure is generated in a product, a glycogen debranching enzyme can be used, if necessary.

A glycogen debranching enzyme which can be used in the present invention is an enzyme having two kinds of activities, α-1,6-glucosidase activity and 4-α-glucanotransferase activity. Due to 4-α-glucanotransferase activity possessed by a glycogen debranching enzyme, a product having a cyclic structure is obtained.

A glycogen debranching enzyme is present in microorganisms and animals. Examples of a microorganism producing a glycogen debranching enzyme include yeast. Examples of animals producing a glycogen debranching enzyme include mammals such as human, rabbit, rat, and pig. An organism producing a glycogen debranching enzyme is not limited to the above examples.

A solvent used in the production method of the present invention can be any solvent as far as it is a solvent which does not deteriorate the enzyme activity of sucrose phosphorylase and α-glucan phosphorylase.

As far as a reaction producing a α-glucan can proceed, it is not necessary that a solvent completely dissolves materials used in the production method according to the present invention. For example, when an enzyme is carried on a solid carrier, it is not necessary that an enzyme is dissolved in a solvent. Further, it is not necessary that all of reaction materials such as sucrose are dissolved, and it is enough that a part of materials, to such an extent that a reaction can proceed, is dissolved.

A representative solvent is water. A solvent may be water in a cell lysate, accompanying sucrose phosphorylase or α-glucan phosphorylase upon the preparation of sucrose phosphorylase or α-glucan phosphorylase.

Any other substance may be contained in a solution containing a sucrose phosphorylase, an α-glucan phosphorylase, sucrose, a primer, and inorganic phosphoric acid or glucose-1-phosphate, as long as interaction between the sucrose phosphorylase and sucrose, and interaction between the α-glucan phosphorylase and the primer are not hampered. Examples of such a substance include a buffer, a component of a microorganism producing sucrose phosphorylase (e.g. bacterium, fungus), a component of a microorganism producing α-glucan phosphorylase (e.g. bacterium, fungus), salts, and a medium component.

Amounts of these materials to be used are the known, and can be appropriately selected by those skilled in the art.

In the production method according to the present invention, firstly, a reaction solution is prepared. A reaction solution can be prepared, for example, by adding a sucrose phosphorylase, an α-glucan phosphorylase, solid sucrose, a primer, and inorganic phosphoric acid or glucose-1-phosphate to a suitable solvent. Alternatively, a reaction solution may be prepared by mixing solutions each containing a sucrose phosphorylase, an α-glucan phosphorylase, sucrose, a primer, or inorganic phosphoric acid or glucose-1-phosphate. Alternatively, a reaction solution may be prepared by mixing other solid components into a solution containing some components amongst a sucrose phosphorylase, an α-glucan phosphorylase, sucrose, a primer, and inorganic phosphoric acid or glucose-1-phosphate. Any buffer may be added to this reaction solution, if necessary, for the purpose of adjusting a pH as long as it does not inhibit an enzyme reaction. To this reaction solution may be added an enzyme selected from the group consisting of: a debranching enzyme, a branching enzyme, 4-α-glucanotransferase and a glycogen debranching enzyme, if necessary.

A reaction solution is then heated, if necessary, by the methods known in the art, to react it. A reaction temperature can be any temperature as long as the effect of the invention is obtained. When a sucrose concentration in a reaction solution at reaction initiation is about 5% to about 100%, a reaction temperature can be typically a temperature of about 40° C. to about 70° C. It is preferable that the temperature of a solution in this reaction step is such a temperature that activity (activities) which is about 50% or more, more preferably about 80% or more of activity of at least one of, preferably activities of both of sucrose phosphorylase and α-glucan phosphorylase contained in this solution before a reaction remain(s) after a predetermined reaction time. This temperature is preferably about 50° C. to about 70° C., more preferably about 55° C. to about 70° C., further preferably about 55° C. to about 65° C.

The reaction time can be selected taking the reaction temperature, the molecular weight of α-glucan produced by the reaction, and the remaining activity of the enzymes into consideration. The reaction time is typically about 1 hour to about 100 hours, more preferably about 1 hour to about 72 hours, more preferably about 2 hours to about 36 hours, most preferably about 2 hours to about 24 hours.

In this manner, a solution containing α-glucan is produced.

As an SP having improved thermostability of the present invention, an SP is preferred which, when the reaction is carried out using the SP at 55° C. under the same conditions as in Example 4, gives a higher amylose yield than those by the natural SP. In this case, the amylose yield is preferably 5% or more, more preferably 10% or more, still more preferably 20% or more, most preferably 30% or more. An SP having improved thermostability which meets this condition can be selected by carrying out a reaction under the same conditions as in Example 4 to determine the amylose yield.

(5. Method of Synthesizing Glucose-1-Phosphate Using an Enzyme of the Present Invention)

A sucrose phosphorylase having improved thermostability of the present invention can also be used advantageously in a method of synthesizing glucose-1-phosphate. A method of synthesizing glucose-1-phosphate using a sucrose phosphorylase having improved thermostability of the present invention can be any method of synthesizing glucose-1-phosphate which is known in the art.

The method of synthesizing glucose-1-phosphate in the present invention comprises reacting a reaction solution containing the sucrose phosphorylase having improved thermostability of the present invention, sucrose and inorganic phosphoric acid to produce glucose-1-phosphate.

The definition of sucrose and inorganic acid used in the method of synthesizing glucose-1-phosphate according to the present invention is the same as in the above item 4.

The amount of the materials used in the method of synthesizing glucose-1-phosphate is known and can be suitably selected by those skilled in the art.

In the method of synthesizing glucose-1-phosphate according to the present invention, firstly, a reaction solution is prepared. A reaction solution can be prepared, for example, by adding a sucrose phosphorylase, sucrose and inorganic phosphoric acid to a suitable solvent. Alternatively, a reaction solution may be prepared by mixing solutions each containing a sucrose phosphorylase, sucrose or inorganic phosphoric acid. Alternatively, a reaction solution may be prepared by mixing other solid components into a solution containing some components amongst a sucrose phosphorylase, sucrose, a primer, and inorganic phosphoric acid. Any buffer may be added to this reaction solution, if necessary, for the purpose of adjusting a pH as long as it does not inhibit an enzyme reaction.

A reaction solution is then heated, if necessary, by the methods known in the art, to react it. A reaction temperature can be any temperature as long as the effect of the invention is obtained. It is preferable that the temperature of a solution in this reaction step is such a temperature that activity which is about 50% or more, preferably about 80% or more of activity of sucrose phosphorylase contained in this solution before a reaction remain(s) after a predetermined reaction time. This temperature is preferably about 50° C. to 70° C., more preferably about 55° C. to 70° C., and further more preferably about 55° C. to 65° C.

A reaction time can be set to be any time, in view of the reaction temperature and the remaining activity of an enzyme. A reaction time is representatively about 1 hour to about 100 hours, more preferably about 1 hour to about 72 hours, further more preferably about 2 hours to about 36 hours, most preferably about 2 hours to about 24 hours.

In this manner, a solution containing glucose-1-phosphate is produced.

As an SP having improved thermostability of the present invention, an SP is preferred which, when the reaction is carried out using the SP at 55° C. under the same conditions as in Example 5, gives a higher glucose-1-phosphate yield than those by the natural SP. In this case, the glucose-1-phosphate yield is preferably 5% or more, more preferably 10% or more, still more preferably 20% or more, further more preferably 30% or more, even more preferably 40% or more, even more preferably 50% or more, even more preferably 60% or more, especially preferably 70% or more, and most preferably 80%. An SP having improved thermostability which meets this condition can be selected by carrying out a reaction under the same conditions as in Example 5 to determine the glucose-1-phosphate yield.

(6. Other Production Methods Using an Enzyme According to the Present Invention)

A sucrose phosphorylase having improved thermostability according to the present invention can be used in any production methods known in the art using sucrose phosphorylase, in addition to the aforementioned production methods. Such a method is for example a method of synthesizing a glucose polymer. This method comprises reacting a reaction solution containing a sucrose phosphorylase having improved thermostability of the present invention; a second phosphorylase using α-glucose-1-phosphate as a substrate; sucrose; a primer; and inorganic phosphoric acid or glucose-1-phosphate to produce a glucose polymer. In the present specification, the "glucose polymer" refers to a polymer partially containing glucose residues. Examples of the glucose polymer include glucan (for example, α-glucan and β-1,3-glucan), cellobiose, cellooligosaccharide, laminaribiose, laminarioligosaccharide, and trehalose. In the case where the glucose polymer is α-glucan, the production method is as described in the above item "4. Method for producing α-glucan using enzyme of the present invention".

Examples of production methods for a glucose polymer other than α-glucan include the following: for example, production of cellobiose and cellooligosaccharide by a combination of cellobiose phosphorylase and cellodextrin phosphorylase (see "A production method for cellobiose" in Japanese Patent No. 2815023); production of laminaribiose and laminarioligosaccharide by a combination of laminaribiose phosphorylase and laminaridextrin phosphorylase (see "A production method for laminarioligosaccharide" in Japanese Laid-Open Publication No. 6-343484); production of β-1,3-glucan by combination with β-1,3-glucan phosphorylase (see "A production method for laminarioligosaccharide" in Japanese Laid-Open Publication No. 6-343484); and production of trehalose by combination with trehalose phosphorylase (see "A production Method for trehalose" in JP-A 7-327691). These methods can be used. Utilization of a sucrose phosphorylase having improved thermostability of the present invention to these production methods can be easily carried out by those skilled in the art. If a sucrose phosphorylase having improved thermostability of the present invention is used in these production methods, the reaction can be carried out at higher temperatures than conventional, thus improving the yield of the product.

(7. Use of α-Glucan Obtained by a Production Method According to the Present Invention)

An α-glucan obtained by the production method according to the present invention can be used in uses known in the art regarding a glucan. Among an α-glucan, particularly, with regard to insoluble amylose, the same function as that of dietary fiber is predicted, and utilization in a health food can be expected. Further, since amylose has the characteristic of being capable of including, for example, iodine or fatty acids in a molecule, use in the field of medicaments, cosmetics or sanitary products is expected. Amylose can be utilized as a raw material for producing cyclodextrin and cycloamylose having the same inclusion ability as that of amylose. Further, a film containing amylose has a tensile strength comparable to that of a general-use plastic, and is very promising as a material for a biodegradable plastic. High-molecular-weight amyloses are also suitable for chiral fractionation. In this manner, many uses are expected in amylose.

(8. Use of Glucose-1-Phosphate Obtained by Synthesis Method According to the Present Invention)

Glucose-1-phosphate obtained by the synthesis method according to the present invention can be used in uses known in the art regarding glucose-1-phosphate. Glucose-1-phosphate is utilized, for example, as a medical antibacterial agent, an anti-tumor agent (a platinum complex), a drug to treat heart disease (an amine salt), a substrate for synthesizing a glucan (for example, α-1,4-glucan or β-1,3-glucan), a substrate for synthesizing a cellobiose, a substrate for synthesizing a cellooligosaccharide, a substrate for synthesizing a laminaribiose, a substrate for synthesizing a laminarioligosaccharide, and a substrate for synthesizing a trehalose.

The present invention will be explained below based on Examples, but the following Examples are provided only for the purpose of exemplification. Therefore, the scope of the present invention is not limited by the aforementioned Detailed Description of the Invention and the following Examples, but is limited only by claims.

EXAMPLES

1. Measurement Method and Calculation Method

Respective substances in the present invention were measured using the following measurement methods.

(1.1 Quantitation of Glucose)

Glucose was quantitated using a commercially available measuring kit. Glucose is measured using a glucose AR-II color developing reagent (manufactured by Wako Pure Chemical Industries, Ltd.).

(1.2 Quantitation of Fructose)

Fructose was quantitated using a commercially available measuring kit. Fructose is measured using F-kit, D-glucose/D-fructose (manufacture by Roche).

(1.3 Quantitation of glucose-1-phosphate)

Glucose-1-phosphate was quantitated by the following method. To 300 μl of a measuring reagent (200 mM Tris-HCl (pH 7.0), 3 mM NADP, 15 mM magnesium chloride, 3 mM EDTA, 15 μM glucose-1,6-diphosphate, 6 μg/ml phosphoglucomutase, 6 μg/ml glucose-6-phosphate dehydrogenase) is added 600 μl of a solution containing properly diluted glucose-1-phosphate, this is stirred, and the resulting reaction mixture is reacted at 30° C. for 30 minutes. Thereafter, absorbance at 340 nm is measured using a spectrophotometer. Absorbance is measured similarly using sodium glucose-1-phosphate having a known concentration, to produce a standard curve. An absorbance obtained for a sample is fitted to this standard curve to obtain a glucose-1-phosphate concentration in a sample. Usually, activity of producing one μmol glucose-1-phosphate for 1 minute is defined as one unit. In this quantitation method, only glucose-1-phosphate is quantitated, and an amount of inorganic phosphoric acid is not quantitated.

(1.4 Quantitation of Inorganic Phosphoric Acid)

Inorganic phosphoric acid was obtained as phosphate ions by the following method. Into a solution (200 μl) containing inorganic phosphoric acid is mixed 800 μl of a molybdenum reagent (15 mM ammonium molybdate, 100 mM zinc acetate), subsequently, 200 μl of 568 mM ascorbic acid (pH 5.0) is added, this is stirred, and the resulting reaction mixture is reacted at 30° C. for 30 minutes. Thereafter, absorbance at 850 nm is measured using a spectrophotometer. Absorbance is measured similarly using inorganic phosphoric acid having the known concentration, to produce a standard curve. An absorbance obtained for a sample is fitted to this standard curve, to obtain a measure of the inorganic phosphoric acid in a sample. In this quantitation method, the amount of inorganic phosphoric acid is quantitated, and the amount of a glucose-1-phosphate is not quantitated.

(1.5 Method of Calculating Yield of Glucan)

When a glucan is synthesized by the SP-GP method, the yield of a glucan (for example, an amylose) produced using inorganic phosphoric acid as a starting material is obtained from the amounts of glucose, fructose and glucose-1-phosphate in the solution after reaction termination, according to the following equation:

Glucan (mM glucose equivalent)=(fructose (mM)−(glucose-1-phosphate (mM))−(glucose (mM))

This equation is based on the following principle.

In the production method of the present invention, firstly, a reaction (A) according to the following equation can occur.

sucrose+inorganic phosphoric acid→glucose-1-phosphate+fructose     (A)

This reaction is catalyzed by sucrose phosphorylase. In this reaction, sucrose and inorganic phosphoric acid are reacted to produce the same molar amounts of glucose-1-phosphate and fructose. Since the resulting fructose reacts with other substance no longer, a molar amount of produced glucose-1-phosphate is known by measuring a molar amount of fructose.

Sucrose phosphorylase can catalyze hydrolysis of sucrose of the following reaction (B) as a side reaction in addition to the aforementioned reaction (A).

Sucrose→glucose+fructose     (B)

An amount of glucose incorporated into a glucan is calculated as follows.

Amount of glucose incorporated into a glucan=
(amount of glucose-1-phosphate produced by reaction (A))−(amount of unreacted glucose-1-phosphate)=(amount of fructose produced by reaction (A))−(amount of unreacted glucose-1-phosphate)

In view of the fructose produced by a reaction (B), the amount of fructose produced by a reaction (A) is calculated as follows:

(Amount of fructose produced by reaction (A))=
(amount of fructose after reaction termination)−(amount of glucose after reaction termination)

Therefore, a yield of a glucan is obtained by the following equation.

(Glucan (mM glucose equivalent))=(fructose(mM))−(glucose-1-phosphate(mM))−(glucose(mM))

A yield of a glucan produced using glucose-1-phosphate as a starting material is obtained by the following equation from an amount of initial glucose-1-phosphate, as well as amounts of glucose, fructose and glucose-1-phosphate in a solution after reaction termination.

(Glucan (mM glucose equivalent))=(initial glucose-1-phosphate (mM))+(fructose (mM))−(glucose (mM))−(glucose-1-phosphate after reaction (mM))

This equation is based on the following principle.

In a reaction solution, in addition to initial glucose-1-phosphate, glucose-1-phosphate is produced by a reaction (A). That is, initial glucose-1-phosphate and produced glucose-1-phosphate can be used in glucan synthesis. By subtracting the amount of glucose-1-phosphate remaining in a reaction solution after reaction termination, from the amount of glucose-1-phosphate which can be used in glucan synthesis, the amount of glucose-1-phosphate used in a reaction, that is, an amount of glucose incorporated into a glucan can be calculated. Therefore, an amount of glucose incorporated into a glucan can be obtained by the aforementioned equation. This equation can be also applied when inorganic phosphoric acid and glucose-1-phosphate are used together as a starting material in a SP-GP-reaction system.

(1.6 Yield of Glucan)

A yield of a glucan when produced using inorganic phosphoric acid as a starting material is obtained by the following equation.

(Glucan yield (%))=(glucan (mM glucose equivalent))/(initial sucrose (mM))×100

A yield of a glucan when produced using glucose-1-phosphate as a starting material is obtained by the following equation.

(Glucan yield (%))={(initial glucose-1-phosphate (mM))+(fructose (mM))−(glucose (mM))−(glucose-1-phosphate after reaction (mM))}/{(initial sucrose (mM))+(initial glucose-1-phosphate (mM))}×100

This equation can be also applied when inorganic phosphoric acid and glucose-1-phosphate are used together as a starting material in a SP-GP reaction system.

(1.7 Method of Measuring Sucrose Phosphorylase Activity)

The units of activity of sucrose phosphorylase are obtained for example by the following method.

25 μl of 10% sucrose is mixed with 20 μl of 500 mM phosphate buffer (pH 7.0). To this mixture, 5 μl of a properly diluted enzyme solution from which insoluble proteins were removed is added, this is stirred to give a reaction system. This reaction system is reacted at 37° C. for 20 minutes and then heated at 100° C. for 5 minutes to terminate the reaction. Thereafter, glucose-1-phosphate in the solution after the reaction is quantitated. Usually, the amount of the enzyme that forms 1 mmol glucose-1-phosphate per minute is defined as 1 Unit.

(1.8 Method of Measuring Phosphatase Activity)

The units of activity of phosphatase are obtained for example by the following method. A reaction solution which contains 100 μl of enzyme solution properly diluted with 20 mM Tris-HCl buffer (pH 7.0) and 100 μl of 50 mM aqueous glucose-1-phosphate solution, is kept at 37° C. for 60 minutes, and then free inorganic phosphoric acid generated from glucose-1-phosphate in the reaction solution is quantitated to determine the activity of phosphatase. The amount of the enzyme that forms 1 μmol inorganic phosphoric acid per minute was defined to be 1 Unit.

(1.9 Method of Measuring Amylase Activity)

The units of activity of amylase are obtained for example by the following method. A reaction solution which contains 25 μl of enzyme solution properly diluted with 20 mM Tris-HCl buffer (pH 7.0) and 25 μl of 0.5% aqueous amylose solution (weight-average molecular weight of about 70,000, manufactured by Ajinoki Co., Ltd.) is kept at 37° C. for 60 minutes, then 1 ml aqueous iodine solution (0.1% potassium iodide, 0.01% iodine) is added, and the reaction solution is measured for absorbance at 660 nm. The amount of the enzyme that reduces absorbance at 660 nm by 10% per minute was defined to be 1 Unit.

2. Method of Preparing the Enzymes

Each enzyme used in the Examples of the present invention was prepared by the following methods.

(2.1 Preparation of Sucrose Phosphorylase)

The objective sucrose phosphorylase gene, together with selectable marker genes $Amp^r$ and $Tet^r$, was integrated into pKK388-1 to give plasmid pKK388-SMSP. In this plasmid, the sucrose phosphorylase gene was operably linked under the control of isopropyl-β-D-thiogalactopyranoside (IPTG)-inducible promoter. This plasmid was introduced into *Escherichia coli* TG-1 (manufactured by STRATAGENE) by a competent cell method. This *Escherichia coli* was plated on an antibiotic ampicillin-containing LB medium (1% trypton, 0.5% yeast extract, 1% NaCl, 50 μg/ml ampicillin, 1.5% agar) plate, and then cultured overnight at 37° C. The *Escherichia coli* that had grown on this plate was selected to give *Escherichia coli* into which the sucrose phosphorylase gene had been introduced. By analyzing the sequence of the introduced gene, it was confirmed that the resulting *Escherichia coli* contains the sucrose phosphorylase gene. In addition, by activity measurement, it was confirmed that the resulting *Escherichia coli* expresses sucrose phosphorylase.

The resulting *Escherichia coli* was cultured in 5 ml LB liquid medium (1% trypton, 0.5% yeast extract, 1% NaCl, 50 μg/ml ampicillin) for 18 hours, and the whole culture was inoculated to 1 L of additional LB liquid medium and cultured under shaking at 120 rpm at 37° C. for 6 to 7 hours. Thereafter, IPTG was added to a concentration of 0.04 mM to this medium, and then the *Escherichia coli* was cultured under shaking at 30° C. for additional 18 hours to express sucrose phosphorylase, and the culture was centrifuged at 5,000 rpm for 5 minutes to collect the *Escherichia coli* cells. The resulting *Escherichia coli* cells were suspended in 50 ml of 20 mM Tris-HCl buffer (pH 7.0) and then disrupted by sonication to give 50 ml of liquid containing disrupted microbial cells. Then, sucrose was added to the liquid containing disrupted cells to give a liquid containing disrupted cells containing 20% sucrose. This liquid containing disrupted cells was heated for 20 minutes in a water bath at 55° C. After heating, the liquid was centrifuged at 8,500 rpm for 20 minutes by a centrifuge (AVANTI J-25I, manufactured by BECKMANN) thereby removing insoluble proteins, to give a supernatant.

The resulting supernatant was loaded to pre-equilibrated anion-exchange resin Q-Sepharose (Amersham Pharmacia) to allow sucrose phosphorylase to be adsorbed onto the resin. The resin was washed with a buffer containing 100 mM sodium chloride to remove impurities. Then, the sucrose phosphorylase was eluted with a buffer containing 300 mM sodium chloride, to give an enzyme solution of sucrose phosphorylase having improved thermostability. Then, the enzyme solution of sucrose phosphorylase having improved thermostability which contains 1.5 M ammonium sulfate was applied and adsorbed onto pre-equilibrated Phenyl-TOYO-PEARL resin (manufactured by Tosoh Corporation). The resin was washed with a buffer containing 1.05 M ammonium sulfate to remove impurities. Subsequently, the sucrose phosphorylase was eluted with a buffer containing 0.75 M ammonium sulfate to give purified sucrose phosphorylase. The sucrose phosphorylase-containing solution in this stage can be used in the present invention, but when further purification is necessary, fractionation with gel filtration chromatography on Sephacryl S-200HR (manufactured by Amersham Pharmacia) and the like can be carried out to give a purified enzyme solution.

About 1 μg of the resulting purified sucrose phosphorylase enzyme solution was subjected to SDS-PAGE (SDS-polyacrylamide gel electrophoresis). As a result, any purified sucrose phosphorylase enzyme solution indicated a single band at a position corresponding to a molecular weight of about 55,000, and no band was observed in any other place. It was thus revealed that the sucrose phosphorylase was purified to homogeneity.

(2.2 Method of Preparing Recombinant *Thermus aquaticus* α-glucan Phosphorylase)

*Thermus aquaticus* α-glucan phosphorylase gene (J. Appl. Glycosci., 48(1) (2001) 71), together with selectable marker genes $Amp^r$ and $Tet^r$, was integrated into pKK388-1 (manufactured by CLONTECH) to give plasmid pKK388-GP. In this plasmid, the α-glucan phosphorylase gene was operably linked under the control of isopropyl-β-D-thiogalactopyranoside (IPTG)-inducible promoter. This plasmid was introduced into *Escherichia coli* MC1061 (manufactured by Pharmacia) by a competent cell method. This *Escherichia coli* was plated on an antibiotic ampicillin-containing LB medium (1% trypton, 0.5% yeast extract, 1% NaCl, 50 μg/ml ampicillin, 1.5% agar) plate, and then cultured overnight at 37° C. The *Escherichia coli* that had grown on this plate was selected to give *Escherichia coli* into which the α-glucan phosphorylase gene had been introduced. By analyzing the sequence of the introduced gene, it was confirmed that the resulting *Escherichia coli* contains the α-glucan phosphorylase gene.

In addition, by activity measurement, it was confirmed that the resulting *Escherichia coli* expresses α-glucan phosphorylase.

The resulting *Escherichia coli* was cultured in 5 ml LB liquid medium (1% trypton, 0.5% yeast extract, 1% NaCl, 50 µg/ml ampicillin) for 18 hours, and the whole culture was inoculated to 1 L of additional LB liquid medium and cultured under shaking at 120 rpm at 37° C. for 4 to 5 hours. Thereafter, IPTG was added to a concentration of 0.01 mM to this medium, and then the *Escherichia coli* was cultured under shaking at 37° C. for an additional 20 hours. Then, the culture was centrifuged at 5,000 rpm for 5 minutes to collect the *Escherichia coli* dells. The obtained *Escherichia coli* cells were suspended in 50 ml of 20 mM Tris-HCl buffer (pH 7.0) and then disrupted by sonication to give 50 ml of liquid containing disrupted microbial cells.

Then, the liquid containing disrupted cells was heated at 70° C. for 30 minutes. After heating, this liquid containing disrupted cells was centrifuged at 8,500 rpm for 20 minutes thereby removing insoluble proteins and the like, to give a supernatant. The resulting supernatant was used as a recombinant *Thermus aquaticus* α-glucan phosphorylase solution.

Example 1

Preparation, Screening and Sequencing of a Gene of a Sucrose Phosphorylase Having Improved Thermostability Briefly, a random mutation was introduced into a *Streptococcus mutans*-derived sucrose phosphorylase gene, and the randomly mutated gene was introduced into *Escherichia coli* to express a randomly mutated sucrose phosphorylase, and selected a *Escherichia coli* which expresses, among the expressed sucrose phosphrylases, a sucrose phosphorylase having improved thermostability which has glucan synthesizing ability, after heating at 52.5° C. for 15 minutes, and from this *Escherichia coli*, a gene of the sucrose phosphorylase having improved thermostability was isolated and its sequence was determined.

The details are as follows.

Firstly, a random mutation was introduced into the natural *Streptococcus mutans*-derived sucrose phosphorylase gene set forth in SEQ ID NO: 1 by error-prone PCR method known to those skilled in the art to give a randomly mutated SP gene. Under this condition, generally, 1 to 2 random mutations are introduced into one sucrose phosphorylase gene. The randomly mutated SP gene, together with selectable marker genes Amp$^r$ and Tet$^r$, was integrated into pKK388-1 to give plasmid library pKK388-SMSP. In this plasmid library, the sucrose phosphorylase gene was operably linked under the control of isopropyl-β-D-thiogalactopyranoside (IPTG)-inducible promoter.

This plasmid library was introduced into *Escherichia coli* TG-1by a competent cell method. This *Escherichia coli* was plated on an antibiotic ampicillin-containing LB medium (1% trypton, 0.5% yeast extract, 1% NaCl, 50 g/ml ampicillin, 1.5% agar) plate, and then cultured overnight at 37° C. The *Escherichia coli* that had grown on this plate was selected to give about 100,000 *Escherichia coli* into which the sucrose phosphorylase gene had been introduced.

Each of these *Escherichia coli* was inoculated into separate 150 µl terrific broth liquid medium (manufactured by GIBCO BRL) containing 50 µg/ml ampicillin, followed by stationary culture at 37° C. for 18 hours. Thereafter, 150 µl of lyzing solution (10 mg/ml egg white lysozyme, 1 U/ml deoxyribonuclease, 200 mM magnesium chloride, 0.5% Triton X-100) was added to the culture and then frozen at −80° C. for 1 hour and then thawed at 37° C. for 1 hour to give a microbial cell extract. The resulting microbial cell extract was centrifuged at 13,000 rpm for 10 minutes by a centrifuge (CT-13R manufactured by Hitachi) thereby removing insoluble proteins and the like, to give a supernatant.

50 µl of the resulting supernatant was placed into a 1.5-ml microtube, then heated at 52.5° C. for 15 minutes and then transferred rapidly onto ice to terminate heating. Then, to this, 50 µl assay solution (4% sucrose, 100 mM phosphate buffer (pH 7.0), 0.5 mM maltotetraose, 2 U/ml potato-derived α-glucan phosphorylase) was added, mixed and incubated at 45° C. for 2 hours. Thereafter, this was color developed by adding 100 µl iodine solution (1.3% potassium iodide, 0.13% iodine). If sucrose phosphorylase is present in the supernatant, amylose is synthesized from sucrose during incubation, and the amylose turns blue by iodine, while sucrose is not colored, so the supernatant turning blue by the iodine solution contains the sucrose phosphorylase having improved thermostability. By screening in the method described above, about 100 *Escherichia coli* containing a gene of a sucrose phosphorylase having improved thermostability were obtained from about 80,000 *Escherichia Coli* transformants containing the randomly mutated sucrose phosphorylase gene.

From the *Escherichia coli* containing a gene of a sucrose phosphorylase having improved thermostability, obtained by the screening described above, the plasmid was recovered by a method known in the art, and the sequence of the gene of the sucrose phosphorylase having improved thermostability in this plasmid was determined by a DNA sequencer (manufactured by ABI).

By comparing the amino acid sequence encoded by this gene of the sucrose phosphorylase having improved thermostability with the amino acid sequence (amino acid sequence of SEQ ID NO: 2) of the natural sucrose phosphorylase, a mutation was introduced at amino acid positions corresponding to positions 47, 62, 77, 128, 140, 144, 155 and 249 in the natural sucrose phosphorylase, and the amino acid substitutions at these positions are as follows, respectively: T47→S, S62→P, Y77→H, V128→L, K140→M, Q144→R, N155→S, and D249→G. Thus, 8 amino acid positions are confirmed which are considered effective in improving the thermostability of a sucrose phosphorylase. Among these, especially, the mutations T47→S and V128→L are the so-called conservative substitutions. Because an improvement in thermostability is observed even when an amino acid is substituted with another similar amino acid, which is referred to as conservative substitution, this position was putative to be a position particularly related to thermostability, so it is expected that further improvement in the thermostability can be brought about by substitution of the amino acid with another amino acid not similar thereto. Further, since, except for these 8 positions, no mutations which influence thermostability were found, it is considered that mutations in other positions are not effective for thermostability.

Further, improvement of thermostability is brought about by amino acids other than S at T47, amino acids other than P at S62, amino acids other than H at Y77, amino acids other than L at V128, amino acids other than M at K140, amino acids other than R at Q144, amino acids other than S at N155, or amino acids other than G at D249.

Example 2A

Preparation of Sucrose Phosphorylase Having Improved Thermostability by Site-Directed Mutagenesis and Measurement of Thermostability (1) Preparation of Sucrose Phosphorylase Having Improved Thermostability by Site-Directed Mutagenesis Briefly, a library having a combination of the 8 mutations described above was prepared. The library was screened to provide sucrose phosphorylase with further improved thermostability.

To be described in detail, an expression vector of sucrose phosphorylase having improved thermostability was prepared in the same manner as in Example 1. In this example, genes encoding SP having improved thermostability which has only one substitution in a position revealed to contribute to improvement of thermostability, genes encoding SP having improved thermostability which has a any combination of 2 to 7 substitutions, and a gene encoding SP having improved thermostability which has all the 8 substitutions were prepared. By way of example, the base sequence encoding SP having improved thermostability which has all the 8 mutations (T47S, S62P, Y77H, V128L, K140K, Q144R, N155S and D249G) is shown in SEQ ID NO: 21, and the amino acid sequence of this SP having improved thermostability is shown in SEQ ID NO: 22. These amino acid substitutions were created by using site-directed mutagenesis known in the art.

Each of the thus obtained genes which encodes an SP having improved thermostability was used to integrate into pKK388-1 in the same manner as in above Example 1 to give plasmid pKK388-SPMS. This plasmid was introduced into *Escherichia coli* TG-1 by a competent cell method, and this *Escherichia coli* was plated on an antibiotic ampicillin-containing LB medium (1% trypton, 0.5% yeast extract, 1% NaCl, 50 μg/ml ampicillin, 1.5% agar) plate and then cultured overnight at 37° C. The *Escherichia coli* that had grown on this plate was selected to give *Escherichia coli* into which a gene encoding a sucrose phosphorylase having improved thermostability had been introduced. By analyzing the sequence of the introduced gene, it was confirmed that the resulting *Escherichia coli* contains the sucrose phosphorylase gene. The *Escherichia coli* expressing a SP having improved thermostability could be prepared in this manner.

From the resulting *Escherichia coli* expressing sucrose phosphorylase having improved thermostability, a solution of a sucrose phosphorylase enzyme having improved thermostability was prepared according to the method described in 2.1.

(1-2) Preparation of Natural Sucrose Phosphorylase

Using the gene of SEQ ID NO: 1, a natural sucrose phosphorylase enzyme solution was prepared according to the method described in 2.1.

(1-3) Preparation of Sucrose Phosphorylase (No. 33) Having Substitution and Addition in the C Terminal of Natural Sucrose Phosphorylase Using the gene set forth in SEQ ID NO: 23, a solution of sucrose phosphorylase (referred to for the sake of convenience as No. 33) enzyme wherein compared with the sucrose phosphorylase of SEQ ID NO: 2, the C-terminal two amino acids FE were substituted with SL, and methionine, isoleucine, serine, cysteine, glutamine and threonine were added in this order to the C terminal, was prepared according to the method described in 2.1.

(1-4) Preparation of Sucrose Phosphorylases (Nos. 1a, 2a, 3a, 4a, 5a and 6a) Having Substitution and Addition in the C Terminal of Mutant SP The C-terminal of a SP enzyme having improved thermostability which has an objective mutation was subjected to amino acid substitution and addition, and it was confirmed that the thermostability is not influenced by such substitution and addition.

Specifically, solutions of C-modified SP enzymes wherein in SP enzyme No. 1, 2, 3, 4, 5 or 6 having improved thermostability in Table 4A, the C-terminal two amino acids (phenylalanine and glutamic acid) were substituted with leucine and serine respectively, and 6 amino acids, that is, methionine, isoleucine, serine, cysteine, glutamine and threonine were added in this order to the C terminal, were prepared and measured for their thermostability.

(2) Measurement of the Thermostability of Various Sucrose Phosphorylases

The solutions of a SP enzyme having improved thermostability prepared in (1) to (1-4) above or other SP enzyme solutions were measured for their thermostability. The measurement was carried out in the following manner.

(i) Thermostability of SP in the Absence of Sucrose

Firstly, each SP enzyme solution was appropriately diluted to be 2.5 to 3.5 U/ml at 37° C. with 20 mM Tris buffer (pH 7.0). 50 μl of the diluted enzyme solution was heated at 55° C. for 20 minutes or at 57° C. for 20 minutes, or at 60° C. for 20 minutes. Immediately after heating, each sample was cooled on ice for 10 minutes. The activity of the enzyme solution after cooling and the activity of the enzyme solution before heating were measured at 37° C. according to the method of measuring SP activity described in 1.7. The thermostability of each enzyme was measured by determining the ratio (remaining activity) of the enzyme activity of the sucrose phosphorylase after heating, to the enzyme activity of the sucrose phosphorylase before heating.

(ii) Thermostability of SP in the Presence of Sucrose

Finally, each SP enzyme solution was appropriately diluted to be 5.0 to 7.0 U/ml with 20 mM Tris buffer (pH 7.0). 25 μl of the diluted enzyme solution was mixed with 25 μl of 40% sucrose containing 20 mM Tris buffer (pH 7.0). 50 μl of this mixed solution was heated at 65° C. for 20 minutes. Immediately after heating, each solution was cooled on ice for 10 minutes. The activity of the enzyme solution after cooling and the activity of the enzyme solution before heating were measured at 37° C. according to the method of measuring SP activity described in 1.7. The thermostability of each enzyme was measured by determining the ratio (remaining activity) of the enzyme activity of the sucrose phosphorylase after heating, to the enzyme activity of the sucrose phosphorylase before heating. The results obtained in the case when SP was heated at 55° C., 57° C. or 60° C. in the absence of sucrose and the case when SP was heated at 65° C. in the presence of sucrose are shown in Table 4A below. Table 4A also shows the respective mutants which have a mutation.

TABLE 4A

| No. | 55° C. −Suc | 57° C. −Suc | 60° C. −Suc | 65° C. +Suc | T47S | S62P | Y77H | V128L | K140M | Q144R | N155S | D249G | C-terminal modification |
|---|---|---|---|---|---|---|---|---|---|---|---|---|---|
| 1 | 99.3 | 98.3 | 80.6 | 99.3 | yes | yes | yes | yes | yes | yes | yes | yes | — |
| 1a | 99.1 | 97.4 | 80.5 | 98.9 | yes | yes | yes | yes | yes | yes | yes | yes | yes |
| 2 | 99.4 | 95.2 | 67.2 | 99.1 | yes | yes | yes | — | yes | yes | yes | — |
| 2a | 99.1 | 96.1 | 66.4 | 98.3 | yes | yes | yes | — | yes | yes | yes | yes |
| 3 | 98.3 | 86.5 | 20.9 | 98.2 | yes | — | — | yes | — | yes | — | yes | — |
| 3a | 98.7 | 85.1 | 21.3 | 97.4 | yes | — | — | yes | — | yes | — | yes | yes |
| 4 | 94.2 | 86.5 | 14.8 | 91.7 | yes | yes | — | — | — | yes | — | yes | — |

TABLE 4A-continued

| No. | 55° C. −Suc | 57° C. −Suc | 60° C. −Suc | 65° C. +Suc | T47S | S62P | Y77H | V128L | K140M | Q144R | N155S | D249G | C-terminal modification |
|---|---|---|---|---|---|---|---|---|---|---|---|---|---|
| 4a | 95.8 | 88.1 | 15.3 | 93.3 | yes | yes | — | — | — | yes | — | yes | yes |
| 5 | 95.8 | 93.7 | 35.9 | 94.8 | yes | — | — | yes | — | yes | yes | yes | — |
| 5a | 94.9 | 94.2 | 37.4 | 92.9 | yes | — | — | yes | — | yes | yes | yes | yes |
| 6 | 98.4 | 99.3 | 38.4 | 95.4 | yes | yes | — | yes | — | — | yes | yes | — |
| 6a | 97.3 | 96.3 | 36.1 | 93.2 | yes | yes | — | yes | — | — | yes | yes | yes |
| 7 | 95.5 | 94.1 | 30.6 | 93.3 | yes | yes | yes | yes | yes | yes | — | — | — |
| 8 | 91.8 | 80.8 | 28.9 | 88.9 | yes | yes | yes | yes | — | yes | — | — | — |
| 9 | 99.4 | 83.5 | 22.0 | 84.3 | yes | yes | — | — | — | yes | yes | yes | — |
| 10 | 95.4 | 83.2 | 27.1 | 88.4 | yes | — | yes | — | yes | yes | — | yes | — |
| 11 | 96.2 | 89.4 | 26.1 | 89.6 | yes | yes | yes | — | — | yes | yes | yes | — |
| 12 | 96.3 | 83.0 | 25.4 | 69.4 | — | — | — | yes | — | yes | yes | yes | — |
| 13 | 91.8 | 70.3 | 19.1 | 78.3 | yes | yes | — | yes | — | yes | yes | — | — |
| 14 | 90.5 | 78.0 | 20.5 | 62.4 | — | — | — | yes | — | — | yes | yes | — |
| 15 | 90.0 | 77.1 | 17.7 | 82.6 | — | yes | — | yes | — | yes | — | yes | — |
| 16 | 94.3 | 80.6 | 18.3 | 85.0 | yes | yes | — | — | yes | — | yes | yes | — |
| 17 | 92.2 | 75.9 | 11.5 | 85.0 | yes | yes | — | — | — | — | — | yes | — |
| 18 | 98.5 | 81.9 | 14.6 | 83.5 | yes | yes | — | — | — | — | yes | yes | — |
| 19 | 88.7 | 60.7 | 11.9 | 83.2 | yes | yes | yes | yes | — | yes | — | — | — |
| 20 | 80.3 | 49.4 | 7.6 | 38.7 | — | — | yes | yes | — | — | yes | — | — |
| 21 | 80.8 | 48.8 | 7.1 | 53.4 | — | — | yes | — | yes | yes | — | yes | — |
| 22 | 81.2 | 47.5 | 4.1 | 79.1 | yes | yes | — | yes | — | — | — | — | — |
| 23 | 85.2 | 40.2 | 3.6 | 55.8 | yes | yes | — | — | — | yes | yes | — | — |
| 24 | 77.4 | 30.1 | 1.1 | 38.2 | yes | — | — | — | — | — | — | yes | — |
| 25 | 47.3 | 11.5 | 1.1 | 30.4 | yes | — | — | — | — | — | — | — | — |
| 26 | 33.4 | 4.4 | 1.4 | 9.5 | — | yes | — | — | — | — | — | — | — |
| 27 | 22.6 | 2.2 | 1.4 | 6.9 | — | — | yes | — | — | — | — | — | — |
| 28 | 26.6 | 3.0 | 1.7 | 10.8 | — | — | — | yes | — | — | — | — | — |
| 29 | 39.9 | 6.1 | 1.1 | 12.3 | — | — | — | — | yes | — | — | — | — |
| 30 | 23.2 | 2.1 | 1.3 | 5.2 | — | — | — | — | — | yes | — | — | — |
| 31 | 37.8 | 6.3 | 1.0 | 6.3 | — | — | — | — | — | — | yes | — | — |
| 32 | 47.7 | 11.1 | 1.2 | 27.5 | — | — | — | — | — | — | — | yes | — |
| 33 | 10.6 | 2.3 | 1.8 | 1.9 | — | — | — | — | — | — | — | — | yes |
| WT | 11.3 | 2.3 | 1.8 | 1.9 | — | — | — | — | — | — | — | — | — |

In Table 4A above, WT represents an unmutated natural *Streptococcus mutans*-derived sucrose phosphorylase. The mutant No. 33 represents a sucrose phosphorylase wherein in the natural *Streptococcus mutans*-derived sucrose phosphorylase, the C-terminal two amino acids FE were substituted with SL, and methionine, isoleucine, serine, cysteine, glutamine and threonine were added in this order to the C terminal. "Yes" represents the presence of a mutation in that position. For example, the mutant No. 3 has the mutations T47S, V128L, Q144R and D249G. In this table, an activity value of less than 5% is very near to the detection limit of glucose-1-phosphate quantitated by activity measurement, and can be assumed to be almost 0 because of its very low reliability.

In "yes" with respect to C-terminal modification, phenylalanine at position 480 is substituted with leucine, glutamic acid at position 481 is substituted with serine, and methionine, isoleucine, serine, cysteine, glutamine and threonine are added to the continuing positions (positions 482 to 487).

As a result, it was found that as compared with the natural SP, thermostability was improved by substitution in only one position out of the amino acids at 8 positions contributing to thermostability. It was also found that the thermostability of the sucrose phosphorylase was further improved by multiple substitution of amino acid residues at some or all of these 8 positions.

On the other hand, thermostability was hardly influenced by amino acid substitution and addition at the C-terminal. Thus, it was found that substitution or addition of amino acids can be carried out to such an extent that the effect of the invention is not inhibited, and also that substitutions at the positions found by the present inventors are important for thermostability, while substitutions at other positions are meaningless.

Each of mutant sucrose phosphorylase measured for thermostability in the presence of sucrose was improved in their thermostability as compared with that in the absence of sucrose by the presence of sucrose.

Example 2B

Preparation of Sucrose Phosphorylase Having Improved Thermostability Substituted with Various Amino Acid Residues and Measurement of Thermostability A plasmid containing a modified sucrose phosphorylase gene was prepared in the same manner as in Example 2A except that a primer designed to substitute one of T47, S62, Y77, V128, K140, Q144, N155 and D249 with another amino acid residue was used, and various modified SP enzyme solutions were obtained.

The thermostability of these modified SP enzyme solutions was determined by measuring the remaining activity after heating was conducted in the same manner as in Example 2A (2) (i) except that the heating condition was 55° C. for 20 minutes. The results are shown in Table 4B below.

TABLE 4B

| Enzyme solution | remaining activity (%) |
|---|---|
| T47S | 47.3 |
| T47I | 50.0 |
| S62P | 33.4 |
| S62A | 31.0 |
| S62K | 26.3 |
| Y77H | 22.6 |

TABLE 4B-continued

| Enzyme solution | remaining activity (%) |
|---|---|
| Y77R | 34.8 |
| V128L | 26.6 |
| V128I | 49.5 |
| N155S | 37.8 |
| WT | 11.3 |
| K140M | 39.9 |
| K140C | 45.9 |
| K140F | 47.4 |
| K140I | 23.0 |
| K140V | 51.4 |
| K140Y | 53.8 |
| Q144R | 23.2 |
| Q144H | 38.2 |
| Q144I | 33.6 |
| Q144K | 30.3 |
| Q144V | 33.1 |
| D249G | 47.7 |
| D249C | 22.5 |
| D249H | 35.4 |
| D249K | 29.3 |
| D249L | 21.3 |
| D249N | 43.3 |
| D249P | 26.5 |
| D249Q | 24.5 |
| D249R | 21.3 |
| D249S | 22.4 |

In this table, T47S represents a mutant wherein threonine at position 47 in *Streptococcus mutans*-derived SP was substituted with serine. With respect to other mutants, their substitutions are interpreted in this manner. WT represents to *Streptococcus mutans*-derived natural SP.

As a result, it was found that by substituting amino acid residues at each of the 8 positions contributing to thermostability with another amino acid residue, thermostability is improved as compared with that of the natural SP.

Example 2C

Improvement of Thermostability of *Leuconostoc mesenteroides*-Derived Sucrose Phosphorylase and Measurement of Thermostability A plasmid containing a modified sucrose phosphorylase gene was prepared in the same manner as in Example 2A except that a gene (SEQ ID NO: 7) encoding *Leuconostoc mesenteroides*-derived SP was used in place of the gene encoding *Streptococcus mutans*-derived SP, and a primer designed to give each amino acid substitution A62P, V128I or N155S was used, and then various modified SP enzyme solutions were obtained. An enzyme solution of *Leuconostoc mesenteroides*-derived natural SP was used as the control.

The thermostability of these modified SP enzyme solutions was determined by measuring the remaining activity after heating was carried out in the same manner as in above Example 2A(2) (i) except that the heating conditions were 50° C., 52° C. or 55° C. for 20 minutes. The results are shown in Table 4C below. The result of the *Leuconostoc mesenteroides*-derived natural SP is shown as WT.

TABLE 4C

| Sample | 50° C. | 52° C. | 55° C. |
|---|---|---|---|
| WT | 82.7 | 58.3 | 8.6 |
| A62P | 90.5 | 71.2 | 23.9 |
| V128I | 93.0 | 70.8 | 27.3 |
| N155S | 91.3 | 69.2 | 37.9 |

A62 is a position corresponding to S62 in SEQ ID NO: 2. V128 is a position corresponding to V128 in SEQ ID NO: 2. N155 is a position corresponding to N155.

As a result, it was found that also by substituting amino acid residues in the positions contributing to improvement of thermostability with another amino acid residue in the *Leuconostoc mesenteroides*-derived SP, SP having improved thermostability can be obtained.

Example 3

Specific Activity of Sucrose Phosphorylase Having Improved Thermostability at High Temperatures The specific activity of the sucrose phosphorylase having improved thermostability of the present invention at 55° C. was examined.

Specifically, firstly, the solution of the purified sucrose phosphorylase enzyme having improved thermostability No. 2, 3, 4, 5 or 6 or control natural (WT) *Streptococcus mutans* sucrose phosphorylase enzyme solution was appropriately diluted to 1 U/ml at 37° C. with 20 mM Tris buffer (pH 7.0). The activity of the diluted enzyme solution was measured according to the method of measuring SP activity described in 1.7 except that the reaction temperature was 55° C.

Separately, an amount of the sucrose phosphorylase in the enzyme solution which was the same volume as used in the above reaction was quantitated by using a protein assay kit (manufactured by Bio-Rad) according to manufacture's instructions. A calibration curve for measurement was prepared by using IgG.

From the SP activity (A (U/ml)) and SP weight (W (mg/ml)) thus determined, the specific activity of SP was determined by calculating A/W (U/mg).

The results are shown in Table 5 below.

TABLE 5

| No. | Specific activity (U/mg protein) |
|---|---|
| 2 | 44.1 |
| 3 | 96.4 |
| 4 | 163.9 |
| 5 | 32.2 |
| 6 | 40.3 |
| WT | 10.7 |

As a result, it was found that the specific activity at 55° C. is significantly improved by the introduction of a mutation.

Example 4

Amylose Synthesis Using Sucrose Phosphorylase Having Improved Thermostability

The amylose yield in amylose synthesis using the sucrose phosphorylase having improved thermostability of the present invention was examined. As the sucrose phosphorylase having improved thermostability, various SPs having improved thermostability (Nos. 1 to 6, 25 and 32) prepared in Example 3 were used.

As the control, Streptococcus mutans-derived natural sucrose phosphorylase was used.

The amylose synthesis reaction was carried out at 50° C. or 55° C. for 18 hours in a reaction system having the composition shown in Table 6 below.

TABLE 6

| Composition for amylose synthesis reaction | Amount |
|---|---|
| Sucrose | 292.3 mM |
| Maltotetraose (G4) | 1 mM |
| Inorganic phosphoric acid (Pi) | 10 mM |
| α-Glucan phosphorylase | 1 U/ml |
| Sucrose phosphorylase | 1 U/ml |

As the α-glucan phosphorylase, the recombinant *Thermus aquaticus*-derived glucan phosphorylase prepared in 2.2 was used.

The yield of amylose synthesized by this reaction was calculated according to the above-described "1. Measurement method and calculation method".

The yield of amylose synthesized by this method is shown in Table 7 below.

TABLE 7

| | Yield of synthesized amylose | |
|---|---|---|
| | Amylose yield (%) | |
| No. | 50° C. | 55° C. |
| 1 | 91.3 | 35.3 |
| 2 | 91.9 | 34.1 |
| 3 | 90.3 | 30.5 |
| 4 | 87.4 | 26.3 |
| 5 | 88.8 | 24.7 |
| 6 | 91.1 | 27.7 |
| 25 | 61.3 | 7.3 |
| 32 | 59.5 | 5.4 |
| WT | 27.8 | 2.1 |

As shown above, it was found that the SPs having improved thermostability of the present invention can synthesize amylose under high-temperature conditions (for example, 50° C. to 55° C.). It was found that when the SP having improved thermostability of the present invention is used, amylose can be synthesized at yields that are about twice to about 18 times as high as that when using the wild-type SP.

Example 5

Synthesis of glucose-1-phosphate Using a Sucrose Phosphorylase Having Improved Thermostability The yield of glucose-1-phosphate in glucose-1-phosphate synthesis using the sucrose phosphorylase having improved thermostability of the present invention was examined. As the sucrose phosphorylase having improved thermostability, various sucrose phosphorylase having improved thermostability (Nos. 1 to 6, 25 and 32) prepared in Example 3 were used. As the control, *Streptococcus mutans*-derived natural sucrose phosphorylase (SEQ ID NO: 2) was used. The glucose-1-phosphate synthesis reaction was carried out at 50° C. or 55° C. for 18 hours in a reaction system having the composition shown in Table 8 below.

TABLE 8

| Composition for G-1-P synthesis reaction | Amount |
|---|---|
| Sucrose | 300 mM |
| Inorganic phosphoric acid (Pi) | 300 mM |
| Sucrose phosphorylase | 1 U/ml |

The amount of glucose-1-phosphate synthesized by this reaction was quantitated by the method described in "1. Measurement method and calculation method" above. The yield of glucose-1-phosphate thus obtained was determined according to the following formula:

Yield (%)=glucose-1-phosphate yield (mM)/initial sucrose concentration (300 mM)×100

The results are shown in Table 9 below.

TABLE 9

| | Yield of glucose-1-phosphate (%) | |
|---|---|---|
| No. | Reaction at 50° C. | Reaction at 55° C. |
| 1 | 88.2 | 88.5 |
| 2 | 89.3 | 87.2 |
| 3 | 87.6 | 89.4 |
| 4 | 88.1 | 87.3 |
| 5 | 85.8 | 80.3 |
| 6 | 81.1 | 82.2 |
| 25 | 78.0 | 19.0 |
| 32 | 79.9 | 7.8 |
| WT | 70.4 | 5.4 |

As shown above, it was found that the SPs having improved thermostability of the present invention can synthesize glucose-1-phosphate under high-temperature conditions. It was found that when the SP having improved thermostability of the present invention is used particularly under the reaction condition at 55° C., glucose-1-phosphate can be synthesized at yields that are about 1.5 times to about 16 times as high as that when using the wild-type SP.

Example 6

Confirmation of Removal of Contaminating Proteins by Heating Treatment

It was confirmed by the following method that the sucrose phosphorylase having improved thermostability can be easily purified by heat treatment.

Each *Escherichia coli* expressing the sucrose phosphorylase having improved thermostability No. 1, 2, 3, 4 or 5 shown in the Table 4A and *Escherichia coli* expressing the natural (SEQ ID NO: 2) *Streptococcus mutans*-derived sucrose phosphorylase as the control was cultured in the same manner as in the method described in Example 2A(1). Each culture was centrifuged to recover the microbial cells which were then suspended in a buffer and sonicated to give a microbial cell extract. Sucrose was added to this microbial cell extract to give a mixture containing sucrose at a concentration of 20%, and this mixture was heated at 65° C. for 20 minutes and then centrifuged to remove insoluble proteins, whereby an SP enzyme solution was obtained. The specific activity of this SP enzyme solution at 37° C. was determined. The results are shown in Table 10. Measurement of the protein amount used in calculation of the specific activity was carried out in the same manner as in the method described in Example 3. The phosphatase activity and amylase activity contained in the SP enzyme solution before and after heating were measured to determine the ratio of the residual phosphatase and amylase activities, relative to those before heating. The results are shown in Table 11.

TABLE 10

| | Specific activity | |
|---|---|---|
| No. | Before heating (U/mg protein) | After heating (U/mg protein) |
| 1 | 11.8 | 37.2 |
| 2 | 8.5 | 42.2 |
| 3 | 9.3 | 33.8 |
| 4 | 14.1 | 56.8 |
| 5 | 8.0 | 27.2 |
| 6 | 13.9 | 41.1 |
| WT | 10.5 | 0.1 |

TABLE 11

Phosphatase activity and amylase activity in SP enzyme solution

| No. | Phosphatase activity (%) | Amylase activity (%) |
|---|---|---|
| 1 | 2.6 | 0.6 |
| 2 | 2.1 | 0.2 |
| 3 | 1.7 | 0.4 |
| 4 | 2.7 | 0.6 |
| 5 | 2.5 | 0.2 |
| 6 | 1.8 | 0.4 |
| WT | 2.2 | 0.5 |

The enzyme solution containing the SP having improved thermostability was heated at 65° C. to remove denatured proteins, whereby the specific activity of the resulting purified enzyme solution became about 3 times to about 5 times as high as that before heating. This indicates that a majority of contaminating proteins were denatured and removed without denaturing the SP having improved thermostability. On the other hand, the specific activity of natural (WT; SEQ ID NO: 2) SP was reduced to about 1/100. This indicates that not only contaminating proteins but also the SP protein were denatured. Further, by heating at 65° C., the phosphatase activity and amylase activity derived from the microbial host could be reduced respectively to about 3.0t or less and about 1.0% or less of those before heating. It was thus found that by heat treatment of the SP having improved thermostability, the SP having improved thermostability can be easily purified.

Example 7

Influence, on Specific Activity, of Amino Acid Substitution in the C-Terminal and Amino Acid Addition to the C-Terminal The C-terminal of the SP enzyme was subjected to amino acid substitution and addition besides the objective mutation, and it was confirmed that the specific activity was not influenced by such amino acid substitution and addition.

Specifically, DNA having the base sequence set forth in SEQ ID NO: 23 was used, and a C-terminal-modified SP enzyme (No. 33 prepared in Example 2A (1-3) above) having the amino acid sequence set forth in SEQ ID NO: 24 was prepared in the same manner as in the method described in 2.1 and measured for specific activity.

The specific activities of the C-terminal-modified SP enzyme and the natural SP enzyme at 37° C. were measured in the same manner as in the method described in Example 3 except that the reaction temperature was 37° C. The results are shown in Table 12 below. As a result, a difference between the specific activity of the C-terminal-modified SP enzyme and the specific activity of the natural SP enzyme was hardly recognized. Accordingly, it was found that the activity of the sucrose phosphorylase was hardly influenced by substitution of amino acids in the C-terminal and addition of amino acids to the C-terminal.

TABLE 12

| Enzyme | Specific activity (U/mg protein) |
|---|---|
| Natural SP enzyme | 62.5 |
| C-terminal-modified SP enzyme (No. 33) | 60.4 |

As described above, the present invention was exemplified using preferable embodiments of the present invention, but it should not be construed to limit the present invention to those embodiments. It is understood that the scope of the present invention should be construed only by claims. It is understood that those skilled in the art can practice an equivalent scope based on the description of the present invention and common technical knowledge, from the specific description of preferable embodiments of the present invention. It is understood that the content itself of patents, patent applications and references cited in the present specification should be incorporated by reference, as if the content thereof are specifically described in the present specification.

INDUSTRIAL APPLICABILITY

According to the present invention, there can be provided sucrose phosphorylase having improved thermostability which can be utilized in efficient production of glucan, G-1-P and the like at high temperatures.

The invention claimed is:

1. A purified sucrose phosphorylase having improved thermostability, which is obtained by modifying a natural sucrose phosphorylase, wherein the sucrose phosphorylase having improved thermostability has an amino acid residue which is different from that of the natural sucrose phosphorylase in at least one position selected from the group consisting of:

a position corresponding to position 14, a position corresponding to position 29 and a position corresponding to position 44 in motif sequence 1: AVGGVHLL-PFFPSTGDRGFAPIDYHEVDSAFGDWDDVKRL GEKYYLMFDFMINHIS (SEQ ID NO. 25);

a position corresponding to position 7, a position corresponding to position 19, a position corresponding to position 23 and a position corresponding to position 34 in motif sequence 2: RPTQED-VDLIYKRKDRAPKQEIQFADGSVEHL-WNTFGEEQID (SEQ ID NO. 26); and a position corresponding to position 19 in motif sequence 3: ILPEIHEHYTIQFKIADHDYYVYD-FALPMVTLYSLYSG (SEQ ID NO. 27); and wherein enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of enzyme activity of the sucrose phosphorylase having improved thermostability at 37° C., before heating wherein the amino acid sequence of the natural sucrose phosphorylase has at least 95% sequence identity to the sequence of SEQ ID N: 2.

2. The sucrose phosphorylase having improved thermostability according to claim 1, wherein the amino acid sequence of the natural sucrose phosphorylase is encoded by a nucleic acid molecule which hybridizes under stringent conditions to a nucleic acid molecule consisting of a base sequence encoding SEQ ID NO: 2, using the conditions under which hybridization is performed at 65° C. in a solution containing 50% formamide, 750 mM NaCl, 75 mM trisodium citrate and 50 mM sodium phosphate.

3. The sucrose phosphorylase having improved thermostability according to claim 1, wherein the amino acid sequence of the natural sucrose phosphorylase is selected from the group consisting of SEQ ID NO: 2, SEQ ID NO: 4, SEQ ID NO: 6 and SEQ ID NO: 12.

4. The sucrose phosphorylase having improved thermostability according to claim 1, wherein the natural sucrose phosphorylase is obtained from a bacterium selected from the group consisting of *Streptococcus mutans*, *Streptococcus pneumoniae*, *Streptococcus sorbinus*, *Streptococcus mitis*, *Leuconostoc mesenteroides*, *Oenococcus oeni*, *Lactobacillus acidophilus* and *Listeria monocytogenes*.

5. The sucrose phosphorylase having improved thermostability according to claim 1, wherein the natural sucrose phosphorylase is obtained from *Streptococcus mutans*, *Streptococcus pneumoniae*, *Streptococcus sorbinus* or *Streptococcus mitis*.

6. The sucrose phosphorylase having improved thermostability according to claim 1, wherein the natural sucrose phosphorylase is obtained from *Streptococcus mutans* or *Leuconostoc mesenteroides*.

7. The sucrose phosphorylase having improved thermostability according to claim 1, wherein the amino acid residue in a position corresponding to position 14 in motif sequence 1 is serine or isoleucine.

8. The sucrose phosphorylase having improved thermostability according to claim 1, wherein the amino acid residue in a position corresponding to position 29 in motif sequence 1 is proline, alanine or lysine.

9. The sucrose phosphorylase having improved thermostability according to claim 1, wherein the amino acid residue in a position corresponding to position 44 in motif sequence 1 is histidine, arginine or tryptophan.

10. The sucrose phosphorylase having improved thermostability according to claim 1, wherein the amino acid residue in a position corresponding to position 44 in motif sequence 1 is arginine.

11. The sucrose phosphorylase having improved thermostability according to claim 1, wherein the amino acid residue in a position corresponding to position 7 in motif sequence 2 is leucine or isoleucine.

12. The sucrose phosphorylase having improved thermostability according to claim 1, wherein the amino acid residue in a position corresponding to position 19 in motif sequence 2 is methionine, cysteine, phenylalanine, isoleucine, valine or tyrosine.

13. The sucrose phosphorylase having improved thermostability according to claim 1, wherein the amino acid residue in a position corresponding to position 19 in motif sequence 2 is valine or tyrosine.

14. The sucrose phosphorylase having improved thermostability according to claim 1, wherein the amino acid residue in a position corresponding to position 23 in motif sequence 2 is arginine, histidine, isoleucine, lysine or valine.

15. The sucrose phosphorylase having improved thermostability according to claim 1, wherein the amino acid residue in a position corresponding to position 23 in motif sequence 2 is histidine.

16. The sucrose phosphorylase having improved thermostability according to claim 1, wherein the amino acid residue in a position corresponding to position 34 in motif sequence 2 is serine or threonine.

17. The sucrose phosphorylase having improved thermostability according to claim 1, wherein the amino acid residue in a position corresponding to position 34 in motif sequence 2 is serine.

18. The sucrose phosphorylase having improved thermostability according to claim 1, wherein the amino acid residue in a position corresponding to position 19 in motif sequence 3 is glycine, cysteine, histidine, lysine, leucine, asparagine, proline, glutamine, arginine or serine.

19. The sucrose phosphorylase having improved thermostability according to claim 1, wherein the amino acid residue in a position corresponding to position 19 in motif sequence 3 is glycine.

20. The sucrose phosphorylase having improved thermostability according to claim 1, wherein the enzyme activity of the sucrose phosphorylase having improved thermostability at 37° C., after heating the sucrose phosphorylase having improved thermostability in 20 mM Tris buffer (pH 7.0) at 57° C. for 20 minutes is 10% or more of the enzyme activity of the sucrose phosphorylase having improved thermostability at 37° C. before heating.

21. The sucrose phosphorylase having improved thermostability according to claim 1, wherein the enzyme activity of the sucrose phosphorylase having improved thermostability at 37° C., after heating the sucrose phosphorylase having improved thermostability in 20 mM Tris buffer (pH 7.0) at 57° C. for 20 minutes, is 20% or more of the enzyme activity of the sucrose phosphorylase having improved thermostability at 37° C. before heating.

22. The sucrose phosphorylase having improved thermostability according to claim 1, wherein the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes is 10% or more of the enzyme activity of the sucrose phosphorylase having improved thermostability at 37° C. before heating.

23. The sucrose phosphorylase having improved thermostability according to claim 1, wherein the enzyme activity of the sucrose phosphorylase having improved thermostability at 37° C., after heating the sucrose phosphorylase having improved thermostability in 20 mM Tris buffer (pH 7.0) containing 20% sucrose at 65° C. for 20 minutes, is 20% or more of the enzyme activity of the sucrose phosphorylase having improved thermostability at 37° C. before heating.

24. The sucrose phosphorylase having improved thermostability according to claim 1, which has an amino acid residue which is different from that of the natural sucrose phosphorylase in a position corresponding to position 14 in motif sequence 1.

25. The sucrose phosphorylase having improved thermostability according to claim 1, which has an amino acid residue which is different from that of the natural sucrose phosphorylase in a position corresponding to position 19 in motif sequence 3.

26. A method of synthesizing glucose-1-phosphate, comprising reacting a reaction solution containing the sucrose phosphorylase having improved thermostability according to claim 1, sucrose and inorganic phosphoric acid to produce glucose-1-phosphate.

27. The method according to claim 26, wherein the reaction is carried out at a temperature of 50° C. to 70° C.

28. A method of synthesizing a glucose polymer, comprising reacting a reaction solution containing the sucrose phosphorylase having improved thermostability according to claim 1; a second phosphorylase using α-glucose-1-phosphate as a substrate; sucrose; a primer; and inorganic phosphoric acid or glucose-1-phosphate to produce a glucose polymer.

29. The method according to claim 28, wherein the glucose polymer is an α-glucan.

30. The method according to claim 28, wherein the second phosphorylase is an α-glucan phosphorylase.

31. The method according to claim 28, wherein the second phosphorylase is selected from the group consisting of cellobiose phosphorylase, cellodextrin phosphorylase, laminaribiose phosphorylase, laminaridextrin phosphorylase, β-1,3-glucan phosphorylase and trehalose phosphorylase.

32. The method according to claim 28, wherein the reaction is carried out at a temperature of 50° C. to 70° C.

33. A purified sucrose phosphorylase having improved thermostability, obtained by modifying a natural sucrose phosphorylase,
wherein the sucrose phosphorylase having improved thermostability has an amino acid residue which is different from that of the natural sucrose phosphorylase in at least one position selected from the group consisting of:
a position corresponding to threonine at position 47 (T47); a position corresponding to serine at position 62 (S62); a position corresponding to tyrosine at position 77 (Y77); a position corresponding to valine at position 128 (V128); a position corresponding to lysine at position 140 (K140); a position corresponding to glutamine at position 144 (Q144); a position corresponding to asparagine at position 155 (N155);
and a position corresponding to aspartic acid at position 249 (D249);
in the amino acid sequence of SEQ ID NO: 2; and
wherein the enzyme activity of the sucrose phosphorylase having improved thermostability at 37° C., after heating the sucrose phosphorylase having improved thermostability in 20 mM Tris buffer (pH 7.0) at 55° C. for 20 minutes, is 20% or more of the enzyme activity of the sucrose phosphorylase having improved thermostability at 37° C. before heating wherein the amino acid sequence of the natural sucrose phosphorylase has at least 95% sequence identity to the sequence of SEQ ID NO: 2.

34. A method of synthesizing glucose-1-phosphate, comprising reacting a reaction solution containing the sucrose phosphorylase having improved thermostability according to claim 33, sucrose and inorganic phosphoric acid to produce glucose-1-phosphate.

35. A method of synthesizing a glucose polymer comprising reacting a reaction solution containing: the sucrose phosphorylase having improved thermostability according to claim 33; a second phosphorylase using α-glucose-1-phosphate as a substrate; sucrose; a primer; and inorganic phosphoric acid or glucose-1-phosphate; to produce a glucose polymer.

* * * * *

SEQUENCE LISTING

```
<160> NUMBER OF SEQ ID NOS: 27

<210> SEQ ID NO 1
<211> LENGTH: 1443
<212> TYPE: DNA
<213> ORGANISM: Streptococcus mutans
<220> FEATURE:
<221> NAME/KEY: CDS
<222> LOCATION: (1)..(1443)

<400> SEQUENCE: 1
```

```
atg cca att aca aat aaa aca atg ttg att act tac gca gac agt ttg      48
Met Pro Ile Thr Asn Lys Thr Met Leu Ile Thr Tyr Ala Asp Ser Leu
 1               5                  10                  15 ggt aaa aat ttg aaa gaa ttg aat gaa aat att gag aat tat ttt gga      96
Gly Lys Asn Leu Lys Glu Leu Asn Glu Asn Ile Glu Asn Tyr Phe Gly
             20                  25                  30 gat gct gtt ggc ggt gtc cat ttg ctg cca ttc ttt cct tcc aca ggt     144
Asp Ala Val Gly Gly Val His Leu Leu Pro Phe Phe Pro Ser Thr Gly
         35                  40                  45 gat cgt ggc ttt gca ccg att gat tac cat gaa gtt gac tct gct ttt     192
Asp Arg Gly Phe Ala Pro Ile Asp Tyr His Glu Val Asp Ser Ala Phe
     50                  55                  60 ggc gat tgg gat gat gtc aaa cgt ttg ggt gaa aaa tat tac ctc atg     240
Gly Asp Trp Asp Asp Val Lys Arg Leu Gly Glu Lys Tyr Tyr Leu Met
 65                  70                  75                  80 ttt gat ttc atg att aat cat att tcg cgt cag tct aaa tat tat aaa     288
Phe Asp Phe Met Ile Asn His Ile Ser Arg Gln Ser Lys Tyr Tyr Lys
                 85                  90                  95 gat tac caa gaa aag cat gaa gca agt gct tat aaa gat cta ttt tta     336
Asp Tyr Gln Glu Lys His Glu Ala Ser Ala Tyr Lys Asp Leu Phe Leu
            100                 105                 110 aat tgg gat aaa ttt tgg cct aaa aat cgc ccg aca caa gaa gat gtg     384
Asn Trp Asp Lys Phe Trp Pro Lys Asn Arg Pro Thr Gln Glu Asp Val
        115                 120                 125 gac ctg att tat aag cgt aag gat cga gca cct aag cag gaa atc caa     432
Asp Leu Ile Tyr Lys Arg Lys Asp Arg Ala Pro Lys Gln Glu Ile Gln
    130                 135                 140 ttt gca gat ggc agt gtt gaa cat ctc tgg aac act ttt ggg gag gaa     480
Phe Ala Asp Gly Ser Val Glu His Leu Trp Asn Thr Phe Gly Glu Glu
145                 150                 155                 160 cag att gat ctt gac gtg act aaa gaa gtg act atg gat ttt att cgc     528
Gln Ile Asp Leu Asp Val Thr Lys Glu Val Thr Met Asp Phe Ile Arg
                165                 170                 175 tct acc att gaa aat tta gca gcc aac ggc tgt gat ctc att cgt ttg     576
Ser Thr Ile Glu Asn Leu Ala Ala Asn Gly Cys Asp Leu Ile Arg Leu
            180                 185                 190 gat gcc ttt gct tat gct gtt aaa aag cta gat acg aat gat ttc ttt     624
Asp Ala Phe Ala Tyr Ala Val Lys Lys Leu Asp Thr Asn Asp Phe Phe
        195                 200                 205 gtt gaa cct gaa atc tgg act ctg cta gat aaa gtt cgt gat ata gct     672
Val Glu Pro Glu Ile Trp Thr Leu Leu Asp Lys Val Arg Asp Ile Ala
    210                 215                 220 gct gta tcg ggt gcg gaa atc ttg ccg gaa att cat gaa cac tat act     720
Ala Val Ser Gly Ala Glu Ile Leu Pro Glu Ile His Glu His Tyr Thr
225                 230                 235                 240 att caa ttt aaa att gca gac cat gat tac tat gtt tat gat ttt gcc     768
Ile Gln Phe Lys Ile Ala Asp His Asp Tyr Tyr Val Tyr Asp Phe Ala
                245                 250                 255 ctg cct atg gtg acg ctc tac agc cta tat tcg ggc aag gtt gac cgt     816
Leu Pro Met Val Thr Leu Tyr Ser Leu Tyr Ser Gly Lys Val Asp Arg
            260                 265                 270 ctt gcc aaa tgg ctg aaa atg agt ccg atg aaa cag ttc acc acc ctt     864
Leu Ala Lys Trp Leu Lys Met Ser Pro Met Lys Gln Phe Thr Thr Leu
        275                 280                 285 gat aca cat gac ggt att ggt gtg gtt gat gtt aag gat atc ctg act     912
Asp Thr His Asp Gly Ile Gly Val Val Asp Val Lys Asp Ile Leu Thr
    290                 295                 300 gac gaa gaa att acc tat act tct aat gag ctt tat aag gtc ggt gcc     960
Asp Glu Glu Ile Thr Tyr Thr Ser Asn Glu Leu Tyr Lys Val Gly Ala
305                 310                 315                 320
```

```
aat gtc aat cgt aag tat tca act gcc gaa tat aat aac ttg gat atc     1008
Asn Val Asn Arg Lys Tyr Ser Thr Ala Glu Tyr Asn Asn Leu Asp Ile
            325                 330                 335 tat caa att aat tca act tac tat tca gca ctt ggt gat gat gat caa     1056
Tyr Gln Ile Asn Ser Thr Tyr Tyr Ser Ala Leu Gly Asp Asp Asp Gln
            340                 345                 350 aaa tac ttt ttg gcc cgc ttg ata caa gct ttt gct cca ggt att cca     1104
Lys Tyr Phe Leu Ala Arg Leu Ile Gln Ala Phe Ala Pro Gly Ile Pro
            355                 360                 365 cag gtt tat tac gtt ggc ttt tta gct ggc aag aat gat ctt gaa tta     1152
Gln Val Tyr Tyr Val Gly Phe Leu Ala Gly Lys Asn Asp Leu Glu Leu
        370                 375                 380 ctg gaa agc act aaa gaa ggc cgc aat atc aac cgt cat tat tat agt     1200
Leu Glu Ser Thr Lys Glu Gly Arg Asn Ile Asn Arg His Tyr Tyr Ser
385                 390                 395                 400 agt gaa gaa att gct aag gaa gtg aag cgg cca gtt gtc aag gca ctt     1248
Ser Glu Glu Ile Ala Lys Glu Val Lys Arg Pro Val Val Lys Ala Leu
                405                 410                 415 tta aat ctc ttt act tac cgc aat cag tca gca gct ttt gat ttg gat     1296
Leu Asn Leu Phe Thr Tyr Arg Asn Gln Ser Ala Ala Phe Asp Leu Asp
            420                 425                 430 ggc cgt att gaa gtg gaa acg cca aat gaa gcg acc att gtc ata gaa     1344
Gly Arg Ile Glu Val Glu Thr Pro Asn Glu Ala Thr Ile Val Ile Glu
            435                 440                 445 cgt caa aat aaa gat ggc agt cat atc gca aca gca gag att aat ctc     1392
Arg Gln Asn Lys Asp Gly Ser His Ile Ala Thr Ala Glu Ile Asn Leu
        450                 455                 460 caa gat atg aca tac aga gta aca gaa aat gat caa aca ata agc ttt     1440
Gln Asp Met Thr Tyr Arg Val Thr Glu Asn Asp Gln Thr Ile Ser Phe
465                 470                 475                 480 gaa                                                                 1443
Glu

<210> SEQ ID NO 2
<211> LENGTH: 481
<212> TYPE: PRT
<213> ORGANISM: Streptococcus mutans

<400> SEQUENCE: 2

Met Pro Ile Thr Asn Lys Thr Met Leu Ile Thr Tyr Ala Asp Ser Leu
1               5                   10                  15

Gly Lys Asn Leu Lys Glu Leu Asn Glu Asn Ile Glu Asn Tyr Phe Gly
            20                  25                  30

Asp Ala Val Gly Gly Val His Leu Leu Pro Phe Phe Pro Ser Thr Gly
        35                  40                  45

Asp Arg Gly Phe Ala Pro Ile Asp Tyr His Glu Val Asp Ser Ala Phe
    50                  55                  60

Gly Asp Trp Asp Asp Val Lys Arg Leu Gly Glu Lys Tyr Tyr Leu Met
65                  70                  75                  80

Phe Asp Phe Met Ile Asn His Ile Ser Arg Gln Ser Lys Tyr Lys
                85                  90                  95

Asp Tyr Gln Glu Lys His Glu Ala Ser Ala Tyr Lys Asp Leu Phe Leu
            100                 105                 110

Asn Trp Asp Lys Phe Trp Pro Lys Asn Arg Pro Thr Gln Glu Asp Val
        115                 120                 125

Asp Leu Ile Tyr Lys Arg Lys Asp Arg Ala Pro Lys Gln Glu Ile Gln
    130                 135                 140

Phe Ala Asp Gly Ser Val Glu His Leu Trp Asn Thr Phe Gly Glu Glu
```

```
                145                 150                 155                 160
Gln Ile Asp Leu Asp Val Thr Lys Glu Val Thr Met Asp Phe Ile Arg
                    165                 170                 175
Ser Thr Ile Glu Asn Leu Ala Ala Asn Gly Cys Asp Leu Ile Arg Leu
                180                 185                 190
Asp Ala Phe Ala Tyr Ala Val Lys Lys Leu Asp Thr Asn Asp Phe Phe
            195                 200                 205
Val Glu Pro Glu Ile Trp Thr Leu Leu Asp Lys Val Arg Asp Ile Ala
        210                 215                 220
Ala Val Ser Gly Ala Glu Ile Leu Pro Glu Ile His Glu His Tyr Thr
225                 230                 235                 240
Ile Gln Phe Lys Ile Ala Asp His Asp Tyr Tyr Val Tyr Asp Phe Ala
                245                 250                 255
Leu Pro Met Val Thr Leu Tyr Ser Leu Tyr Ser Gly Lys Val Asp Arg
            260                 265                 270
Leu Ala Lys Trp Leu Lys Met Ser Pro Met Lys Gln Phe Thr Thr Leu
        275                 280                 285
Asp Thr His Asp Gly Ile Gly Val Val Asp Val Lys Asp Ile Leu Thr
    290                 295                 300
Asp Glu Glu Ile Thr Tyr Thr Ser Asn Glu Leu Tyr Lys Val Gly Ala
305                 310                 315                 320
Asn Val Asn Arg Lys Tyr Ser Thr Ala Glu Tyr Asn Asn Leu Asp Ile
                325                 330                 335
Tyr Gln Ile Asn Ser Thr Tyr Tyr Ser Ala Leu Gly Asp Asp Gln
            340                 345                 350
Lys Tyr Phe Leu Ala Arg Leu Ile Gln Ala Phe Ala Pro Gly Ile Pro
        355                 360                 365
Gln Val Tyr Tyr Val Gly Phe Leu Ala Gly Lys Asn Asp Leu Glu Leu
    370                 375                 380
Leu Glu Ser Thr Lys Glu Gly Arg Asn Ile Asn Arg His Tyr Tyr Ser
385                 390                 395                 400
Ser Glu Glu Ile Ala Lys Glu Val Lys Arg Pro Val Val Lys Ala Leu
                405                 410                 415
Leu Asn Leu Phe Thr Tyr Arg Asn Gln Ser Ala Ala Phe Asp Leu Asp
            420                 425                 430
Gly Arg Ile Glu Val Glu Thr Pro Asn Glu Ala Thr Ile Val Ile Glu
        435                 440                 445
Arg Gln Asn Lys Asp Gly Ser His Ile Ala Thr Ala Glu Ile Asn Leu
    450                 455                 460
Gln Asp Met Thr Tyr Arg Val Thr Glu Asn Asp Gln Thr Ile Ser Phe
465                 470                 475                 480
Glu

<210> SEQ ID NO 3
<211> LENGTH: 1434
<212> TYPE: DNA
<213> ORGANISM: Streptococcus pneumoniae
<220> FEATURE:
<221> NAME/KEY: CDS
<222> LOCATION: (1)..(1434)

<400> SEQUENCE: 3 atg cca att caa aat aaa acc atg ttg att acc tat tct gat agc ctt    48
Met Pro Ile Gln Asn Lys Thr Met Leu Ile Thr Tyr Ser Asp Ser Leu
1               5                   10                  15 gga aat aat ctt aaa gac tta tat gat aat ttg gaa gag cat ttt gga    96
```

-continued

| | | | | | | | | | | | | | | |
|---|---|---|---|---|---|---|---|---|---|---|---|---|---|---|
| Gly | Asn | Asn | Leu | Lys | Asp | Leu | Tyr | Asp | Asn | Leu | Glu | Glu | His | Phe | Gly |
| | | 20 | | | | 25 | | | | 30 | | | | | |

| gat | gct | att | gga | gga | gtt | cac | ctt | tta | cca | ttt | ttc | cca | tca | aca | gtt | 144 |
| Asp | Ala | Ile | Gly | Gly | Val | His | Leu | Leu | Pro | Phe | Phe | Pro | Ser | Thr | Val | |
| | | 35 | | | | 40 | | | | 45 | | | | | | |

| gat | cgt | gga | ttt | gcg | cca | gtt | gac | tac | gac | gaa | gtg | gac | tca | gct | ttt | 192 |
| Asp | Arg | Gly | Phe | Ala | Pro | Val | Asp | Tyr | Asp | Glu | Val | Asp | Ser | Ala | Phe | |
| | 50 | | | | 55 | | | | 60 | | | | | | | |

| ggt | gat | tgg | gag | gat | gtg | aag | cgt | tta | ggt | gag | aaa | tat | tat | ctt | atg | 240 |
| Gly | Asp | Trp | Glu | Asp | Val | Lys | Arg | Leu | Gly | Glu | Lys | Tyr | Tyr | Leu | Met | |
| 65 | | | | 70 | | | | 75 | | | | 80 | | | | |

| ttt | gat | ttt | atg | att | aat | cat | att | tct | cgt | caa | tcc | aag | tat | tat | aag | 288 |
| Phe | Asp | Phe | Met | Ile | Asn | His | Ile | Ser | Arg | Gln | Ser | Lys | Tyr | Tyr | Lys | |
| | | | | 85 | | | | 90 | | | | 95 | | | | |

| gac | tat | caa | gaa | aaa | cat | gaa | gcc | agt | gaa | ttt | aaa | gct | ctc | ttt | tta | 336 |
| Asp | Tyr | Gln | Glu | Lys | His | Glu | Ala | Ser | Glu | Phe | Lys | Ala | Leu | Phe | Leu | |
| | | | 100 | | | | 105 | | | | 110 | | | | | |

| aac | tgg | gat | aag | ttt | tgg | cca | gaa | aac | cgt | ccg | aca | cag | tct | gat | gta | 384 |
| Asn | Trp | Asp | Lys | Phe | Trp | Pro | Glu | Asn | Arg | Pro | Thr | Gln | Ser | Asp | Val | |
| | 115 | | | | 120 | | | | 125 | | | | | | | |

| gat | tta | att | tac | aag | cgt | aag | gat | cgt | gca | cca | aag | caa | gag | att | gtg | 432 |
| Asp | Leu | Ile | Tyr | Lys | Arg | Lys | Asp | Arg | Ala | Pro | Lys | Gln | Glu | Ile | Val | |
| | 130 | | | | 135 | | | | 140 | | | | | | | |

| ttt | gaa | gat | ggt | tca | gtg | gaa | cat | ttg | tgg | aat | acc | ttt | ggt | gag | gag | 480 |
| Phe | Glu | Asp | Gly | Ser | Val | Glu | His | Leu | Trp | Asn | Thr | Phe | Gly | Glu | Glu | |
| 145 | | | | 150 | | | | 155 | | | | 160 | | | | |

| cag | att | gat | ctt | gat | gtg | acc | aaa | gaa | gta | act | atg | gaa | ttt | atc | cgt | 528 |
| Gln | Ile | Asp | Leu | Asp | Val | Thr | Lys | Glu | Val | Thr | Met | Glu | Phe | Ile | Arg | |
| | | | 165 | | | | 170 | | | | 175 | | | | | |

| aag | acc | att | cag | cac | ttg | gca | agt | aat | ggg | tgt | gat | ttg | att | cgt | cta | 576 |
| Lys | Thr | Ile | Gln | His | Leu | Ala | Ser | Asn | Gly | Cys | Asp | Leu | Ile | Arg | Leu | |
| | | | 180 | | | | 185 | | | | 190 | | | | | |

| gat | gcc | ttt | gct | tat | gca | gtg | aag | aaa | ttg | gat | act | aat | gat | ttc | ttt | 624 |
| Asp | Ala | Phe | Ala | Tyr | Ala | Val | Lys | Lys | Leu | Asp | Thr | Asn | Asp | Phe | Phe | |
| | | 195 | | | | 200 | | | | 205 | | | | | | |

| gtg | gaa | cca | gat | att | tgg | gat | tta | ttg | gac | aaa | gtt | cga | gat | atc | gct | 672 |
| Val | Glu | Pro | Asp | Ile | Trp | Asp | Leu | Leu | Asp | Lys | Val | Arg | Asp | Ile | Ala | |
| | 210 | | | | 215 | | | | 220 | | | | | | | |

| gct | gag | tat | ggg | aca | gag | ctt | tta | cct | gag | att | cat | gaa | cac | tat | tcg | 720 |
| Ala | Glu | Tyr | Gly | Thr | Glu | Leu | Leu | Pro | Glu | Ile | His | Glu | His | Tyr | Ser | |
| 225 | | | | 230 | | | | 235 | | | | 240 | | | | |

| att | cag | ttt | aaa | ata | gca | gac | cat | gat | tac | tat | gtt | tat | gat | ttt | gct | 768 |
| Ile | Gln | Phe | Lys | Ile | Ala | Asp | His | Asp | Tyr | Tyr | Val | Tyr | Asp | Phe | Ala | |
| | | | 245 | | | | 250 | | | | 255 | | | | | |

| ctt | cca | atg | gtg | aca | ctt | tat | act | ctt | tac | agt | tcc | aga | aca | gag | cgt | 816 |
| Leu | Pro | Met | Val | Thr | Leu | Tyr | Thr | Leu | Tyr | Ser | Ser | Arg | Thr | Glu | Arg | |
| | | 260 | | | | 265 | | | | 270 | | | | | | |

| ttg | gct | aag | tgg | tta | aag | atg | agc | ccg | atg | aag | caa | ttt | acg | acg | cta | 864 |
| Leu | Ala | Lys | Trp | Leu | Lys | Met | Ser | Pro | Met | Lys | Gln | Phe | Thr | Thr | Leu | |
| | | 275 | | | | 280 | | | | 285 | | | | | | |

| gat | acc | cat | gat | ggg | att | gga | gta | gta | gat | gtc | aag | gat | atc | ctg | acc | 912 |
| Asp | Thr | His | Asp | Gly | Ile | Gly | Val | Val | Asp | Val | Lys | Asp | Ile | Leu | Thr | |
| | | 290 | | | | 295 | | | | 300 | | | | | | |

| gat | gag | gag | att | gac | tat | gct | tca | aat | gaa | ctc | tat | aag | gtt | gga | gcc | 960 |
| Asp | Glu | Glu | Ile | Asp | Tyr | Ala | Ser | Asn | Glu | Leu | Tyr | Lys | Val | Gly | Ala | |
| 305 | | | | 310 | | | | 315 | | | | 320 | | | | |

| aat | gtc | aaa | cgt | aag | tac | tct | agt | gcc | gag | tat | aac | aac | tta | gat | atc | 1008 |
| Asn | Val | Lys | Arg | Lys | Tyr | Ser | Ser | Ala | Glu | Tyr | Asn | Asn | Leu | Asp | Ile | |
| | | | | 325 | | | | 330 | | | | 335 | | | | |

| tac | caa | atc | aat | tca | acc | tac | tat | tca | gcg | ctt | gga | gat | gat | gat | gtc | 1056 |

```
Tyr Gln Ile Asn Ser Thr Tyr Tyr Ser Ala Leu Gly Asp Asp Val
            340                 345                 350 aag tat ttt ctc gct cgt cta att caa gct ttt gcc cca ggt att cct      1104
Lys Tyr Phe Leu Ala Arg Leu Ile Gln Ala Phe Ala Pro Gly Ile Pro
            355                 360                 365 cag att tac tat gtg ggt cta tta gca ggc aag aat gac ttg aaa tta      1152
Gln Ile Tyr Tyr Val Gly Leu Leu Ala Gly Lys Asn Asp Leu Lys Leu
    370                 375                 380 tta gaa gaa act aaa gaa ggt cga aat att aat cgt cat tac tat agc      1200
Leu Glu Glu Thr Lys Glu Gly Arg Asn Ile Asn Arg His Tyr Tyr Ser
385                 390                 395                 400 aac gag gaa ata gca aaa gaa gtg caa cga cct gtt gtg aag gcc ctt      1248
Asn Glu Glu Ile Ala Lys Glu Val Gln Arg Pro Val Val Lys Ala Leu
                405                 410                 415 ctc aat cta ttt tct ttc cgt aac cgt tca gaa gcc ttt gat cta gaa      1296
Leu Asn Leu Phe Ser Phe Arg Asn Arg Ser Glu Ala Phe Asp Leu Glu
            420                 425                 430 ggg act act gag ata gag aca cca aca gct cac agc att gta atc aaa      1344
Gly Thr Thr Glu Ile Glu Thr Pro Thr Ala His Ser Ile Val Ile Lys
        435                 440                 445 cgt caa aat aaa gat aag tcc gta aca gca gta gta gaa att gat ttg      1392
Arg Gln Asn Lys Asp Lys Ser Val Thr Ala Val Val Glu Ile Asp Leu
    450                 455                 460 caa aat cag act tat cgg gta att gag aat gga gtt gaa gta              1434
Gln Asn Gln Thr Tyr Arg Val Ile Glu Asn Gly Val Glu Val
465                 470                 475

<210> SEQ ID NO 4
<211> LENGTH: 478
<212> TYPE: PRT
<213> ORGANISM: Streptococcus pneumoniae

<400> SEQUENCE: 4

Met Pro Ile Gln Asn Lys Thr Met Leu Ile Thr Tyr Ser Asp Ser Leu
1               5                   10                  15

Gly Asn Asn Leu Lys Asp Leu Tyr Asp Asn Leu Glu Glu His Phe Gly
            20                  25                  30

Asp Ala Ile Gly Gly Val His Leu Leu Pro Phe Phe Pro Ser Thr Val
        35                  40                  45

Asp Arg Gly Phe Ala Pro Val Asp Tyr Asp Glu Val Asp Ser Ala Phe
    50                  55                  60

Gly Asp Trp Glu Asp Val Lys Arg Leu Gly Glu Lys Tyr Tyr Leu Met
65                  70                  75                  80

Phe Asp Phe Met Ile Asn His Ile Ser Arg Gln Ser Lys Tyr Tyr Lys
                85                  90                  95

Asp Tyr Gln Glu Lys His Glu Ala Ser Glu Phe Lys Ala Leu Phe Leu
            100                 105                 110

Asn Trp Asp Lys Phe Trp Pro Glu Asn Arg Pro Thr Gln Ser Asp Val
        115                 120                 125

Asp Leu Ile Tyr Lys Arg Lys Asp Arg Ala Pro Lys Gln Glu Ile Val
    130                 135                 140

Phe Glu Asp Gly Ser Val Glu His Leu Trp Asn Thr Phe Gly Glu Glu
145                 150                 155                 160

Gln Ile Asp Leu Asp Val Thr Lys Glu Val Thr Met Glu Phe Ile Arg
                165                 170                 175

Lys Thr Ile Gln His Leu Ala Ser Asn Gly Cys Asp Leu Ile Arg Leu
            180                 185                 190

Asp Ala Phe Ala Tyr Ala Val Lys Lys Leu Asp Thr Asn Asp Phe Phe
```

```
                195                 200                 205
Val Glu Pro Asp Ile Trp Asp Leu Leu Asp Lys Val Arg Asp Ile Ala
210                 215                 220

Ala Glu Tyr Gly Thr Glu Leu Leu Pro Glu Ile His Glu His Tyr Ser
225                 230                 235                 240

Ile Gln Phe Lys Ile Ala Asp His Asp Tyr Val Tyr Asp Phe Ala
                245                 250                 255

Leu Pro Met Val Thr Leu Tyr Thr Leu Tyr Ser Ser Arg Thr Glu Arg
            260                 265                 270

Leu Ala Lys Trp Leu Lys Met Ser Pro Met Lys Gln Phe Thr Thr Leu
        275                 280                 285

Asp Thr His Asp Gly Ile Gly Val Val Asp Val Lys Asp Ile Leu Thr
    290                 295                 300

Asp Glu Glu Ile Asp Tyr Ala Ser Asn Glu Leu Tyr Lys Val Gly Ala
305                 310                 315                 320

Asn Val Lys Arg Lys Tyr Ser Ser Ala Glu Tyr Asn Asn Leu Asp Ile
                325                 330                 335

Tyr Gln Ile Asn Ser Thr Tyr Tyr Ser Ala Leu Gly Asp Asp Val
            340                 345                 350

Lys Tyr Phe Leu Ala Arg Leu Ile Gln Ala Phe Ala Pro Gly Ile Pro
        355                 360                 365

Gln Ile Tyr Tyr Val Gly Leu Leu Ala Gly Lys Asn Asp Leu Lys Leu
    370                 375                 380

Leu Glu Glu Thr Lys Glu Gly Arg Asn Ile Asn Arg His Tyr Tyr Ser
385                 390                 395                 400

Asn Glu Glu Ile Ala Lys Glu Val Gln Arg Pro Val Val Lys Ala Leu
                405                 410                 415

Leu Asn Leu Phe Ser Phe Arg Asn Arg Ser Glu Ala Phe Asp Leu Glu
            420                 425                 430

Gly Thr Thr Glu Ile Glu Thr Pro Thr Ala His Ser Ile Val Ile Lys
        435                 440                 445

Arg Gln Asn Lys Asp Lys Ser Val Thr Ala Val Val Glu Ile Asp Leu
    450                 455                 460

Gln Asn Gln Thr Tyr Arg Val Ile Glu Asn Gly Val Glu Val
465                 470                 475

<210> SEQ ID NO 5
<211> LENGTH: 1443
<212> TYPE: DNA
<213> ORGANISM: Streptococcus sorbinus
<220> FEATURE:
<221> NAME/KEY: CDS
<222> LOCATION: (1)..(1443)

<400> SEQUENCE: 5 atg aca cta aca aat aaa acg atg tta att acc tac tca gat agt tta      48
Met Thr Leu Thr Asn Lys Thr Met Leu Ile Thr Tyr Ser Asp Ser Leu
1               5                   10                  15 ggt agg aac cta aaa gag ctg gat gaa aat atc agc atc tat ttt gga      96
Gly Arg Asn Leu Lys Glu Leu Asp Glu Asn Ile Ser Ile Tyr Phe Gly
            20                  25                  30 gat gca att gga ggc gtc cat ctc ctg cct ttc ttc ccc tcg aca gga     144
Asp Ala Ile Gly Gly Val His Leu Leu Pro Phe Phe Pro Ser Thr Gly
        35                  40                  45 gat agg gga ttc gct cca gtt gat tac gat aag gtg gat cct gct ttt     192
Asp Arg Gly Phe Ala Pro Val Asp Tyr Asp Lys Val Asp Pro Ala Phe
    50                  55                  60
```

```
ggt gac tgg gat gat gtc aaa cgt tta ggt gct aaa tac tac ctg atg       240
Gly Asp Trp Asp Asp Val Lys Arg Leu Gly Ala Lys Tyr Tyr Leu Met
 65              70                  75                  80 ttt gat ttt atg att aat cat atc tcc cgt caa tct aag tat tat aag       288
Phe Asp Phe Met Ile Asn His Ile Ser Arg Gln Ser Lys Tyr Tyr Lys
                     85                  90                  95 gat ttt caa gag aaa aaa gat gct tct gac tat gcg gat tta ttt ctg       336
Asp Phe Gln Glu Lys Lys Asp Ala Ser Asp Tyr Ala Asp Leu Phe Leu
             100                 105                 110 cgc tgg gaa aaa ttc tgg ccg gaa aac cgt ccc acc caa gca gat att       384
Arg Trp Glu Lys Phe Trp Pro Glu Asn Arg Pro Thr Gln Ala Asp Ile
         115                 120                 125 gat tta att tat aaa cgt aaa gac aag gct cct atg cag gag att gtc       432
Asp Leu Ile Tyr Lys Arg Lys Asp Lys Ala Pro Met Gln Glu Ile Val
     130                 135                 140 ttc gcc gat gga acc aaa gaa cat ctc tgg aat act ttc gga gaa gag       480
Phe Ala Asp Gly Thr Lys Glu His Leu Trp Asn Thr Phe Gly Glu Glu
145                 150                 155                 160 caa att gat cta gat gtt act aaa gaa gtg acc atg gac ttt atc aaa       528
Gln Ile Asp Leu Asp Val Thr Lys Glu Val Thr Met Asp Phe Ile Lys
                 165                 170                 175 aaa aac atc gag cat cta gca gtc aat ggt tgt gat ctc att cgc ctg       576
Lys Asn Ile Glu His Leu Ala Val Asn Gly Cys Asp Leu Ile Arg Leu
             180                 185                 190 gat gcc ttt gcc tac gcc gtg aaa aaa ttg gac act aat gat ttc ttt       624
Asp Ala Phe Ala Tyr Ala Val Lys Lys Leu Asp Thr Asn Asp Phe Phe
         195                 200                 205 gtc gaa cca gaa att tgg gat ctc cta acc aag gta cag aca atc gcc       672
Val Glu Pro Glu Ile Trp Asp Leu Leu Thr Lys Val Gln Thr Ile Ala
     210                 215                 220 aag gaa gca ggg gca gat atc ctg ccg gaa ata cat gag cat tat tct       720
Lys Glu Ala Gly Ala Asp Ile Leu Pro Glu Ile His Glu His Tyr Ser
225                 230                 235                 240 atc cag ttc aaa att gct gag cat gac tat ttc att tat gat ttt gcc       768
Ile Gln Phe Lys Ile Ala Glu His Asp Tyr Phe Ile Tyr Asp Phe Ala
                 245                 250                 255 ctt cca atg gta acc ctt tac tct ctt tat agc ggt agg gtg caa cgt       816
Leu Pro Met Val Thr Leu Tyr Ser Leu Tyr Ser Gly Arg Val Gln Arg
             260                 265                 270 ttg gca gat tgg ctg gct aaa agt cct atg aag caa ttt act acg ctg       864
Leu Ala Asp Trp Leu Ala Lys Ser Pro Met Lys Gln Phe Thr Thr Leu
         275                 280                 285 gat acc cat gat ggc att gga gtt gta gat gtt aaa gat atc ttg aca       912
Asp Thr His Asp Gly Ile Gly Val Val Asp Val Lys Asp Ile Leu Thr
     290                 295                 300 gac gag gaa att gct tac act tcc gat caa ctc tac aag gtt gga gcc       960
Asp Glu Glu Ile Ala Tyr Thr Ser Asp Gln Leu Tyr Lys Val Gly Ala
305                 310                 315                 320 aac gtc aat cgc aaa tat tca acg gca gaa tat aat aac ctt gat att      1008
Asn Val Asn Arg Lys Tyr Ser Thr Ala Glu Tyr Asn Asn Leu Asp Ile
                 325                 330                 335 tat caa atc aac tcg acc tac tat tca gcc ctt ggt gac gat gac aag      1056
Tyr Gln Ile Asn Ser Thr Tyr Tyr Ser Ala Leu Gly Asp Asp Asp Lys
             340                 345                 350 aag tat ttc tta gct cgt ctc att caa gct ttt gca cca ggg att cca      1104
Lys Tyr Phe Leu Ala Arg Leu Ile Gln Ala Phe Ala Pro Gly Ile Pro
         355                 360                 365 caa gtt tat tat gtt gga ctt ttg gct gga aaa aac gat ctg aag ctc      1152
Gln Val Tyr Tyr Val Gly Leu Leu Ala Gly Lys Asn Asp Leu Lys Leu
     370                 375                 380
```

```
ttg gaa aaa acc aag gaa ggt cgc aat atc aat cgt cat tat tat agc    1200
Leu Glu Lys Thr Lys Glu Gly Arg Asn Ile Asn Arg His Tyr Tyr Ser
385                 390                 395                 400 agt gaa gag att gct cac gag gtt gaa cgg cca gtt gtc aaa gct ttg    1248
Ser Glu Glu Ile Ala His Glu Val Glu Arg Pro Val Val Lys Ala Leu
                405                 410                 415 atc aaa ctg ttt agc tat cgc aac aac tct caa gct ttc gac tta gac    1296
Ile Lys Leu Phe Ser Tyr Arg Asn Asn Ser Gln Ala Phe Asp Leu Asp
            420                 425                 430 ggc agc ctt gaa acg gaa gtt ctg gat gac cac acc atc gtt atc aag    1344
Gly Ser Leu Glu Thr Glu Val Leu Asp Asp His Thr Ile Val Ile Lys
        435                 440                 445 cgt tct aat cag gac aag agt gct tta gct caa gct gtt att aat ttg    1392
Arg Ser Asn Gln Asp Lys Ser Ala Leu Ala Gln Ala Val Ile Asn Leu
    450                 455                 460 caa gat tta acc tat cag gtc act gag aat ggt caa acc att aca ttc    1440
Gln Asp Leu Thr Tyr Gln Val Thr Glu Asn Gly Gln Thr Ile Thr Phe
465                 470                 475                 480 gaa                                                                1443
Glu

<210> SEQ ID NO 6
<211> LENGTH: 481
<212> TYPE: PRT
<213> ORGANISM: Streptococcus sorbinus

<400> SEQUENCE: 6

Met Thr Leu Thr Asn Lys Thr Met Leu Ile Thr Tyr Ser Asp Ser Leu
1               5                   10                  15

Gly Arg Asn Leu Lys Glu Leu Asp Glu Asn Ile Ser Ile Tyr Phe Gly
            20                  25                  30

Asp Ala Ile Gly Gly Val His Leu Leu Pro Phe Phe Pro Ser Thr Gly
        35                  40                  45

Asp Arg Gly Phe Ala Pro Val Asp Tyr Asp Lys Val Asp Pro Ala Phe
    50                  55                  60

Gly Asp Trp Asp Asp Val Lys Arg Leu Gly Ala Lys Tyr Tyr Leu Met
65                  70                  75                  80

Phe Asp Phe Met Ile Asn His Ile Ser Arg Gln Ser Lys Tyr Tyr Lys
                85                  90                  95

Asp Phe Gln Glu Lys Lys Asp Ala Ser Asp Tyr Ala Asp Leu Phe Leu
            100                 105                 110

Arg Trp Glu Lys Phe Trp Pro Glu Asn Arg Pro Thr Gln Ala Asp Ile
        115                 120                 125

Asp Leu Ile Tyr Lys Arg Lys Asp Lys Ala Pro Met Gln Glu Ile Val
    130                 135                 140

Phe Ala Asp Gly Thr Lys Glu His Leu Trp Asn Thr Phe Gly Glu Glu
145                 150                 155                 160

Gln Ile Asp Leu Asp Val Thr Lys Glu Val Thr Met Asp Phe Ile Lys
                165                 170                 175

Lys Asn Ile Glu His Leu Ala Val Asn Gly Cys Asp Leu Ile Arg Leu
            180                 185                 190

Asp Ala Phe Ala Tyr Ala Val Lys Lys Leu Asp Thr Asn Asp Phe Phe
        195                 200                 205

Val Glu Pro Glu Ile Trp Asp Leu Leu Thr Lys Val Gln Thr Ile Ala
    210                 215                 220

Lys Glu Ala Gly Ala Asp Ile Leu Pro Glu Ile His Glu His Tyr Ser
225                 230                 235                 240
```

-continued

```
Ile Gln Phe Lys Ile Ala Glu His Asp Tyr Phe Ile Tyr Asp Phe Ala
            245                 250                 255
Leu Pro Met Val Thr Leu Tyr Ser Leu Tyr Ser Gly Arg Val Gln Arg
        260                 265                 270
Leu Ala Asp Trp Leu Ala Lys Ser Pro Met Lys Gln Phe Thr Thr Leu
    275                 280                 285
Asp Thr His Asp Gly Ile Gly Val Val Asp Val Lys Asp Ile Leu Thr
290                 295                 300
Asp Glu Glu Ile Ala Tyr Thr Ser Asp Gln Leu Tyr Lys Val Gly Ala
305                 310                 315                 320
Asn Val Asn Arg Lys Tyr Ser Thr Ala Glu Tyr Asn Asn Leu Asp Ile
                325                 330                 335
Tyr Gln Ile Asn Ser Thr Tyr Tyr Ser Ala Leu Gly Asp Asp Asp Lys
            340                 345                 350
Lys Tyr Phe Leu Ala Arg Leu Ile Gln Ala Phe Ala Pro Gly Ile Pro
        355                 360                 365
Gln Val Tyr Tyr Val Gly Leu Leu Ala Gly Lys Asn Asp Leu Lys Leu
    370                 375                 380
Leu Glu Lys Thr Lys Glu Gly Arg Asn Ile Asn Arg His Tyr Tyr Ser
385                 390                 395                 400
Ser Glu Glu Ile Ala His Glu Val Glu Arg Pro Val Val Lys Ala Leu
                405                 410                 415
Ile Lys Leu Phe Ser Tyr Arg Asn Asn Ser Gln Ala Phe Asp Leu Asp
            420                 425                 430
Gly Ser Leu Glu Thr Glu Val Leu Asp Asp His Thr Ile Val Ile Lys
        435                 440                 445
Arg Ser Asn Gln Asp Lys Ser Ala Leu Ala Gln Ala Val Ile Asn Leu
    450                 455                 460
Gln Asp Leu Thr Tyr Gln Val Thr Glu Asn Gly Gln Thr Ile Thr Phe
465                 470                 475                 480
Glu
```

<210> SEQ ID NO 7
<211> LENGTH: 1470
<212> TYPE: DNA
<213> ORGANISM: Leuconostoc mesenteroides
<220> FEATURE:
<221> NAME/KEY: CDS
<222> LOCATION: (1)..(1470)

<400> SEQUENCE: 7

```
atg gaa att caa aac aaa gca atg ttg atc act tat gct gat tcg ttg      48
Met Glu Ile Gln Asn Lys Ala Met Leu Ile Thr Tyr Ala Asp Ser Leu
1               5                   10                  15 ggc aaa aac tta aaa gat gtt cat caa gtc ttg aaa gaa gat att gga      96
Gly Lys Asn Leu Lys Asp Val His Gln Val Leu Lys Glu Asp Ile Gly
            20                  25                  30 gat gcg att ggt ggg gtt cat ttg ttg cct ttc ttc cct tca aca ggt     144
Asp Ala Ile Gly Gly Val His Leu Leu Pro Phe Phe Pro Ser Thr Gly
        35                  40                  45 gat cgc ggt ttt gcg cca gcc gat tat act cgt gtt gat gcc gca ttt     192
Asp Arg Gly Phe Ala Pro Ala Asp Tyr Thr Arg Val Asp Ala Ala Phe
    50                  55                  60 ggt gat tgg gca gat gtc gaa gca ttg ggt gaa gaa tac tat ttg atg     240
Gly Asp Trp Ala Asp Val Glu Ala Leu Gly Glu Glu Tyr Tyr Leu Met
65                  70                  75                  80 ttt gac ttc atg att aac cat att tct cgt gaa tca gtg atg tat caa     288
Phe Asp Phe Met Ile Asn His Ile Ser Arg Glu Ser Val Met Tyr Gln
```

```
                     85                  90                  95
gat ttt aag aag aat cat gac gat tca aag tat aaa gat ttc ttt att     336
Asp Phe Lys Lys Asn His Asp Asp Ser Lys Tyr Lys Asp Phe Phe Ile
        100                 105                 110 cgt tgg gaa aag ttc tgg gca aag gcc ggc gaa aac cgt cca aca caa     384
Arg Trp Glu Lys Phe Trp Ala Lys Ala Gly Glu Asn Arg Pro Thr Gln
            115                 120                 125 gcc gat gtt gac tta att tac aag cgt aaa gat aag gca cca acg caa     432
Ala Asp Val Asp Leu Ile Tyr Lys Arg Lys Asp Lys Ala Pro Thr Gln
130                 135                 140 gaa atc act ttt gat gat ggc aca aca gaa aac ttg tgg aat act ttt     480
Glu Ile Thr Phe Asp Asp Gly Thr Thr Glu Asn Leu Trp Asn Thr Phe
145                 150                 155                 160 ggt gaa gaa caa att gac att gat gtt aat tca gcc att gcc aag gaa     528
Gly Glu Glu Gln Ile Asp Ile Asp Val Asn Ser Ala Ile Ala Lys Glu
                165                 170                 175 ttt att aag aca acc ctt gaa gac atg gta aaa cat ggt gct aac ttg     576
Phe Ile Lys Thr Thr Leu Glu Asp Met Val Lys His Gly Ala Asn Leu
            180                 185                 190 att cgt ttg gat gcc ttt gcg tat gca gtt aaa aaa gtt gac aca aat     624
Ile Arg Leu Asp Ala Phe Ala Tyr Ala Val Lys Lys Val Asp Thr Asn
        195                 200                 205 gac ttc ttc gtt gag cca gaa atc tgg gac act ttg aat gaa gta cgt     672
Asp Phe Phe Val Glu Pro Glu Ile Trp Asp Thr Leu Asn Glu Val Arg
210                 215                 220 gaa att ttg aca cca tta aag gct gaa att tta cca gaa att cat gaa     720
Glu Ile Leu Thr Pro Leu Lys Ala Glu Ile Leu Pro Glu Ile His Glu
225                 230                 235                 240 cat tac tca atc cct aaa aag atc aat gat cat ggt tac ttc acc tat     768
His Tyr Ser Ile Pro Lys Lys Ile Asn Asp His Gly Tyr Phe Thr Tyr
                245                 250                 255 gac ttt gca tta cca atg aca acg ctt tac aca ttg tat tca ggt aag     816
Asp Phe Ala Leu Pro Met Thr Thr Leu Tyr Thr Leu Tyr Ser Gly Lys
            260                 265                 270 aca aat caa ttg gca aag tgg ttg aag atg tca cca atg aag caa ttc     864
Thr Asn Gln Leu Ala Lys Trp Leu Lys Met Ser Pro Met Lys Gln Phe
        275                 280                 285 aca aca ttg gac acg cat gat ggt att ggt gtc gtt gat gcc cgt gat     912
Thr Thr Leu Asp Thr His Asp Gly Ile Gly Val Val Asp Ala Arg Asp
290                 295                 300 att cta act gat gat gaa att gac tac gct tct gaa caa ctt tac aag     960
Ile Leu Thr Asp Asp Glu Ile Asp Tyr Ala Ser Glu Gln Leu Tyr Lys
305                 310                 315                 320 gtt ggc gcg aat gtc aaa aag aca tat tca tct gct tca tac aac aac    1008
Val Gly Ala Asn Val Lys Lys Thr Tyr Ser Ser Ala Ser Tyr Asn Asn
                325                 330                 335 ctt gat att tac caa att aac tca act tat tat tca gca ttg gga aat    1056
Leu Asp Ile Tyr Gln Ile Asn Ser Thr Tyr Tyr Ser Ala Leu Gly Asn
            340                 345                 350 gat gat gca gca tac ttg ttg agt cgt gtc ttc caa gtc ttt gcg cct    1104
Asp Asp Ala Ala Tyr Leu Leu Ser Arg Val Phe Gln Val Phe Ala Pro
        355                 360                 365 gga att cca caa att tat tac gtt ggt ttg ttg gca ggt gaa aac gat    1152
Gly Ile Pro Gln Ile Tyr Tyr Val Gly Leu Leu Ala Gly Glu Asn Asp
370                 375                 380 atc gcg ctt ttg gag tca act aaa gaa ggt cgt aat att aac cgt cat    1200
Ile Ala Leu Leu Glu Ser Thr Lys Glu Gly Arg Asn Ile Asn Arg His
385                 390                 395                 400 tac tat acg cgt gaa gaa gtt aag tca gaa gtt aag cga cca gtt gtt    1248
Tyr Tyr Thr Arg Glu Glu Val Lys Ser Glu Val Lys Arg Pro Val Val
```

|   |   |   |   |   |   |   |   |   |   |   | 405 |   |   |   |   | 410 |   |   |   |   | 415 |   |   |   |
|---|---|---|---|---|---|---|---|---|---|---|-----|---|---|---|---|-----|---|---|---|---|-----|---|---|---|

```
gct aac tta ttg aag cta ttg tca tgg cgt aat gaa agc cct gca ttt      1296
Ala Asn Leu Leu Lys Leu Leu Ser Trp Arg Asn Glu Ser Pro Ala Phe
        420                     425                     430 gat ttg gct ggc tca atc aca gtt gac acg cca act gat aca aca att      1344
Asp Leu Ala Gly Ser Ile Thr Val Asp Thr Pro Thr Asp Thr Thr Ile
            435                     440                     445 gtg gtg aca cgt caa gat gaa aat ggt caa aac aaa gct gta tta aca      1392
Val Val Thr Arg Gln Asp Glu Asn Gly Gln Asn Lys Ala Val Leu Thr
    450                     455                     460 gcc gat gcg gcc aac aaa act ttt gaa atc gtt gag aat ggt caa act      1440
Ala Asp Ala Ala Asn Lys Thr Phe Glu Ile Val Glu Asn Gly Gln Thr
465                     470                     475                     480 gtt atg agc agt gat aat ttg act cag aac                              1470
Val Met Ser Ser Asp Asn Leu Thr Gln Asn
                485                     490

<210> SEQ ID NO 8
<211> LENGTH: 490
<212> TYPE: PRT
<213> ORGANISM: Leuconostoc mesenteroides

<400> SEQUENCE: 8

Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270
```

```
              Thr Asn Gln Leu Ala Lys Trp Leu Lys Met Ser Pro Met Lys Gln Phe
                      275                 280                 285

Thr Thr Leu Asp Thr His Asp Gly Ile Gly Val Val Asp Ala Arg Asp
                      290                 295                 300

Ile Leu Thr Asp Asp Glu Ile Asp Tyr Ala Ser Glu Gln Leu Tyr Lys
              305                 310                 315                 320

Val Gly Ala Asn Val Lys Lys Thr Tyr Ser Ser Ala Ser Tyr Asn Asn
                                  325                 330                 335

Leu Asp Ile Tyr Gln Ile Asn Ser Thr Tyr Tyr Ser Ala Leu Gly Asn
                          340                 345                 350

Asp Asp Ala Ala Tyr Leu Leu Ser Arg Val Phe Gln Val Phe Ala Pro
                      355                 360                 365

Gly Ile Pro Gln Ile Tyr Tyr Val Gly Leu Leu Ala Gly Glu Asn Asp
                      370                 375                 380

Ile Ala Leu Leu Glu Ser Thr Lys Glu Gly Arg Asn Ile Asn Arg His
              385                 390                 395                 400

Tyr Tyr Thr Arg Glu Glu Val Lys Ser Glu Val Lys Arg Pro Val Val
                                  405                 410                 415

Ala Asn Leu Leu Lys Leu Leu Ser Trp Arg Asn Glu Ser Pro Ala Phe
                              420                 425                 430

Asp Leu Ala Gly Ser Ile Thr Val Asp Thr Pro Thr Asp Thr Thr Ile
                          435                 440                 445

Val Val Thr Arg Gln Asp Glu Asn Gly Gln Asn Lys Ala Val Leu Thr
                      450                 455                 460

Ala Asp Ala Ala Asn Lys Thr Phe Glu Ile Val Glu Asn Gly Gln Thr
              465                 470                 475                 480

Val Met Ser Ser Asp Asn Leu Thr Gln Asn
                                  485                 490

<210> SEQ ID NO 9
<211> LENGTH: 1467
<212> TYPE: DNA
<213> ORGANISM: Oenococcus oeni
<220> FEATURE:
<221> NAME/KEY: CDS
<222> LOCATION: (1)..(1467)

<400> SEQUENCE: 9 atg ccg gtt aaa aat aaa gca atg ctg atc acc tat tcg gat tcg atg        48
Met Pro Val Lys Asn Lys Ala Met Leu Ile Thr Tyr Ser Asp Ser Met
1               5                   10                  15 ggt aag aat atc aag gaa tta caa tac att tta gat aaa tat att gga        96
Gly Lys Asn Ile Lys Glu Leu Gln Tyr Ile Leu Asp Lys Tyr Ile Gly
            20                  25                  30 gac gcg att ggt gga gtt cat ctg ctg cct ttt ttt ccg tca acc gga       144
Asp Ala Ile Gly Gly Val His Leu Leu Pro Phe Phe Pro Ser Thr Gly
        35                  40                  45 gat cgt ggt ttt gcg ccc tcg gat tac act cgt gtc aat ccg gat ttc       192
Asp Arg Gly Phe Ala Pro Ser Asp Tyr Thr Arg Val Asn Pro Asp Phe
    50                  55                  60 ggt gat tgg gag gat gtc gag gaa ctt gga aaa aag tat tat tta atg       240
Gly Asp Trp Glu Asp Val Glu Glu Leu Gly Lys Lys Tyr Tyr Leu Met
65                  70                  75                  80 ttt gat ttc atg att aat cac att tcc cgt gaa tcg att atg tat caa       288
Phe Asp Phe Met Ile Asn His Ile Ser Arg Glu Ser Ile Met Tyr Gln
                85                  90                  95 gat ttc aag gaa aaa aag gat gct tcc agc tac aag gac ttt ttt att       336
Asp Phe Lys Glu Lys Lys Asp Ala Ser Ser Tyr Lys Asp Phe Phe Ile
```

```
                100                 105                 110
cgt tgg gaa aag ttc tgg ccg aaa gga cgc ccg acg aag gcc gat atc      384
Arg Trp Glu Lys Phe Trp Pro Lys Gly Arg Pro Thr Lys Ala Asp Ile
        115                 120                 125 gat tta att tac aaa aga aaa gat aag gcg ccg att cag ggg att act      432
Asp Leu Ile Tyr Lys Arg Lys Asp Lys Ala Pro Ile Gln Gly Ile Thr
130                 135                 140 ttt gca gac ggc agt caa gaa cat ctt tgg aat act ttt ggc gat gag      480
Phe Ala Asp Gly Ser Gln Glu His Leu Trp Asn Thr Phe Gly Asp Glu
145                 150                 155                 160 cag atc gat att aac gtg aag tcc aaa gtt gct cag gaa ttt ttt aaa      528
Gln Ile Asp Ile Asn Val Lys Ser Lys Val Ala Gln Glu Phe Phe Lys
                165                 170                 175 gat act tta cag tca atg gtt aag cac ggt gcg gat ttg att cgc ctg      576
Asp Thr Leu Gln Ser Met Val Lys His Gly Ala Asp Leu Ile Arg Leu
        180                 185                 190 gat gcc ttt gct tat gca att aaa aag att gat act aat gac ttc ttt      624
Asp Ala Phe Ala Tyr Ala Ile Lys Lys Ile Asp Thr Asn Asp Phe Phe
                195                 200                 205 att gaa ccg gaa att tgg gat tta ctg gaa tca gtt cgg aag att ctc      672
Ile Glu Pro Glu Ile Trp Asp Leu Leu Glu Ser Val Arg Lys Ile Leu
        210                 215                 220 gac ccc cta cat gct gaa att tta ccg gaa att tat gaa cat tac aca      720
Asp Pro Leu His Ala Glu Ile Leu Pro Glu Ile Tyr Glu His Tyr Thr
225                 230                 235                 240 atc ccg gcc aaa ata aat gag tat ggt tac ttt acc tat gat ttt gtt      768
Ile Pro Ala Lys Ile Asn Glu Tyr Gly Tyr Phe Thr Tyr Asp Phe Val
                245                 250                 255 tta cct ctg gta att ttg tac act ctt tat tct gga aat ccc aag caa      816
Leu Pro Leu Val Ile Leu Tyr Thr Leu Tyr Ser Gly Asn Pro Lys Gln
        260                 265                 270 ttg gcc aaa tgg ttg aaa atg tca cca aaa aaa cag ttt acg act ctt      864
Leu Ala Lys Trp Leu Lys Met Ser Pro Lys Lys Gln Phe Thr Thr Leu
        275                 280                 285 gat act cat gat gga atc ggg gtt gtt gat gct cgc gat att tta act      912
Asp Thr His Asp Gly Ile Gly Val Val Asp Ala Arg Asp Ile Leu Thr
        290                 295                 300 gat gag gaa atc gac tat act tcc agt gaa ctg tat aaa gtt ggt gcg      960
Asp Glu Glu Ile Asp Tyr Thr Ser Ser Glu Leu Tyr Lys Val Gly Ala
305                 310                 315                 320 aac gtc aaa cgg act tat tca tct gcg gcc tat aat aat ttg gat att      1008
Asn Val Lys Arg Thr Tyr Ser Ser Ala Ala Tyr Asn Asn Leu Asp Ile
                325                 330                 335 tac cag att aac tcg acc tat tat tca gct ctt ggc aat gat gac aaa      1056
Tyr Gln Ile Asn Ser Thr Tyr Tyr Ser Ala Leu Gly Asn Asp Asp Lys
        340                 345                 350 gcc tat ttg ctt gcc cgt gca ata caa att ttt gcc ccg gga att cca      1104
Ala Tyr Leu Leu Ala Arg Ala Ile Gln Ile Phe Ala Pro Gly Ile Pro
        355                 360                 365 caa atc tat tac gca ggc ctg ctg gct ggt gaa aac gat ttg gat ttg      1152
Gln Ile Tyr Tyr Ala Gly Leu Leu Ala Gly Glu Asn Asp Leu Asp Leu
370                 375                 380 ttg gaa aag acc aag gaa gga cgc aat ata aat cgt cat tat tac agt      1200
Leu Glu Lys Thr Lys Glu Gly Arg Asn Ile Asn Arg His Tyr Tyr Ser
385                 390                 395                 400 gaa gaa gaa gtt gcc aat gaa gtg cag aga cca att gtt gcc tgc cta      1248
Glu Glu Glu Val Ala Asn Glu Val Gln Arg Pro Ile Val Ala Cys Leu
                405                 410                 415 ctg aaa ttg ttg gct tgg cgc aat cgc agt gcc gct ttt gat ctt caa      1296
Leu Lys Leu Leu Ala Trp Arg Asn Arg Ser Ala Ala Phe Asp Leu Gln
```

-continued

```
              420                 425                 430
gga gat att caa gtc agc gca acc gac aaa aat gaa atc aaa att att      1344
Gly Asp Ile Gln Val Ser Ala Thr Asp Lys Asn Glu Ile Lys Ile Ile
        435                 440                 445 cga act tca acc aat ggc caa gac acc gcg gaa tta acc gct aat gtg      1392
Arg Thr Ser Thr Asn Gly Gln Asp Thr Ala Glu Leu Thr Ala Asn Val
    450                 455                 460 gct cta aaa acc ttt act ata aag gaa aat gat aaa att att tta att      1440
Ala Leu Lys Thr Phe Thr Ile Lys Glu Asn Asp Lys Ile Ile Leu Ile
465                 470                 475                 480 gaa gat cag act gat aca aag gat atc                                  1467
Glu Asp Gln Thr Asp Thr Lys Asp Ile
                485
```

<210> SEQ ID NO 10
<211> LENGTH: 489
<212> TYPE: PRT
<213> ORGANISM: Oenococcus oeni

<400> SEQUENCE: 10

```
Met Pro Val Lys Asn Lys Ala Met Leu Ile Thr Tyr Ser Asp Ser Met
1               5                   10                  15

Gly Lys Asn Ile Lys Glu Leu Gln Tyr Ile Leu Asp Lys Tyr Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ser Asp Tyr Thr Arg Val Asn Pro Asp Phe
    50                  55                  60

Gly Asp Trp Glu Asp Val Glu Glu Leu Gly Lys Lys Tyr Tyr Leu Met
65                  70                  75                  80

Phe Asp Phe Met Ile Asn His Ile Ser Arg Glu Ser Ile Met Tyr Gln
                85                  90                  95

Asp Phe Lys Glu Lys Lys Asp Ala Ser Ser Tyr Lys Asp Phe Phe Ile
            100                 105                 110

Arg Trp Glu Lys Phe Trp Pro Lys Gly Arg Pro Thr Lys Ala Asp Ile
        115                 120                 125

Asp Leu Ile Tyr Lys Arg Lys Asp Lys Ala Pro Ile Gln Gly Ile Thr
    130                 135                 140

Phe Ala Asp Gly Ser Gln Glu His Leu Trp Asn Thr Phe Gly Asp Glu
145                 150                 155                 160

Gln Ile Asp Ile Asn Val Lys Ser Lys Val Ala Gln Glu Phe Phe Lys
                165                 170                 175

Asp Thr Leu Gln Ser Met Val Lys His Gly Ala Asp Leu Ile Arg Leu
            180                 185                 190

Asp Ala Phe Ala Tyr Ala Ile Lys Lys Ile Asp Thr Asn Asp Phe Phe
        195                 200                 205

Ile Glu Pro Glu Ile Trp Asp Leu Leu Glu Ser Val Arg Lys Ile Leu
    210                 215                 220

Asp Pro Leu His Ala Glu Ile Leu Pro Glu Ile Tyr Glu His Tyr Thr
225                 230                 235                 240

Ile Pro Ala Lys Ile Asn Glu Tyr Gly Tyr Phe Thr Tyr Asp Phe Val
                245                 250                 255

Leu Pro Leu Val Ile Leu Tyr Thr Leu Tyr Ser Gly Asn Pro Lys Gln
            260                 265                 270

Leu Ala Lys Trp Leu Lys Met Ser Pro Lys Lys Gln Phe Thr Thr Leu
        275                 280                 285
```

```
Asp Thr His Asp Gly Ile Gly Val Val Asp Ala Arg Asp Ile Leu Thr
    290                 295                 300

Asp Glu Glu Ile Asp Tyr Thr Ser Ser Glu Leu Tyr Lys Val Gly Ala
305                 310                 315                 320

Asn Val Lys Arg Thr Tyr Ser Ser Ala Ala Tyr Asn Asn Leu Asp Ile
                325                 330                 335

Tyr Gln Ile Asn Ser Thr Tyr Tyr Ser Ala Leu Gly Asn Asp Asp Lys
                340                 345                 350

Ala Tyr Leu Leu Ala Arg Ala Ile Gln Ile Phe Ala Pro Gly Ile Pro
            355                 360                 365

Gln Ile Tyr Tyr Ala Gly Leu Leu Ala Gly Glu Asn Asp Leu Asp Leu
    370                 375                 380

Leu Glu Lys Thr Lys Glu Gly Arg Asn Ile Asn Arg His Tyr Tyr Ser
385                 390                 395                 400

Glu Glu Glu Val Ala Asn Glu Val Gln Arg Pro Ile Val Ala Cys Leu
                405                 410                 415

Leu Lys Leu Leu Ala Trp Arg Asn Arg Ser Ala Ala Phe Asp Leu Gln
            420                 425                 430

Gly Asp Ile Gln Val Ser Ala Thr Asp Lys Asn Glu Ile Lys Ile Ile
    435                 440                 445

Arg Thr Ser Thr Asn Gly Gln Asp Thr Ala Glu Leu Thr Ala Asn Val
450                 455                 460

Ala Leu Lys Thr Phe Thr Ile Lys Glu Asn Asp Lys Ile Ile Leu Ile
465                 470                 475                 480

Glu Asp Gln Thr Asp Thr Lys Asp Ile
            485

<210> SEQ ID NO 11
<211> LENGTH: 1446
<212> TYPE: DNA
<213> ORGANISM: Streptococcus mitis
<220> FEATURE:
<221> NAME/KEY: CDS
<222> LOCATION: (1)..(1446)

<400> SEQUENCE: 11 atg cca att cag aat aaa acc atg ttg att acc tat tca gat agt ctg      48
Met Pro Ile Gln Asn Lys Thr Met Leu Ile Thr Tyr Ser Asp Ser Leu
1               5                   10                  15 gga aat aat ctt aaa gac tta tat gag aat ttg gaa gag tat ttt gga      96
Gly Asn Asn Leu Lys Asp Leu Tyr Glu Asn Leu Glu Glu Tyr Phe Gly
                20                  25                  30 gat gct att ggg gga gtt cac ctt cta cca ttt ttc cca tca aca ggt     144
Asp Ala Ile Gly Gly Val His Leu Leu Pro Phe Phe Pro Ser Thr Gly
            35                  40                  45 gat cgt gga ttt gcg cca gtt gac tac gac gaa gtg gat tca gct ttt     192
Asp Arg Gly Phe Ala Pro Val Asp Tyr Asp Glu Val Asp Ser Ala Phe
    50                  55                  60 ggt gat tgg gag gat gtt aag cgt tta ggt gag aaa tat tat ctt atg     240
Gly Asp Trp Glu Asp Val Lys Arg Leu Gly Glu Lys Tyr Tyr Leu Met
65                  70                  75                  80 ttt gac ttt atg att aat cat att tct cgt caa tct aag tat tat aag     288
Phe Asp Phe Met Ile Asn His Ile Ser Arg Gln Ser Lys Tyr Tyr Lys
                85                  90                  95 gac tat caa gaa aaa cat gaa gcc agt gaa ttt aaa gat ctc ttt tta     336
Asp Tyr Gln Glu Lys His Glu Ala Ser Glu Phe Lys Asp Leu Phe Leu
                100                 105                 110 aac tgg gat aag ttt tgg cca gaa aac cgt ccg aca cag tct gat gta     384
Asn Trp Asp Lys Phe Trp Pro Glu Asn Arg Pro Thr Gln Ser Asp Val
```

```
                  115                 120                 125
gat  tta  att  tac  aag  cgt  aag  gat  cgt  gca  cca  aag  caa  gag  att  gtt       432
Asp  Leu  Ile  Tyr  Lys  Arg  Lys  Asp  Arg  Ala  Pro  Lys  Gln  Glu  Ile  Val
     130                 135                 140 ttt  gaa  gat  ggg  tca  gtc  gaa  cat  ttg  tgg  aat  acc  ttt  ggt  gag  gag       480
Phe  Glu  Asp  Gly  Ser  Val  Glu  His  Leu  Trp  Asn  Thr  Phe  Gly  Glu  Glu
145                 150                 155                 160 cag  att  gat  ctt  gat  gtg  acc  aaa  gaa  gta  act  atg  gaa  ttt  atc  cgt       528
Gln  Ile  Asp  Leu  Asp  Val  Thr  Lys  Glu  Val  Thr  Met  Glu  Phe  Ile  Arg
          165                 170                 175 aag  acc  att  cag  cac  ttg  gca  agt  aat  ggg  tgt  gat  ttg  att  cgt  cta       576
Lys  Thr  Ile  Gln  His  Leu  Ala  Ser  Asn  Gly  Cys  Asp  Leu  Ile  Arg  Leu
               180                 185                 190 gac  gcc  ttt  gct  tat  gca  gtg  aag  aaa  ttg  gat  act  aat  gat  ttc  ttt       624
Asp  Ala  Phe  Ala  Tyr  Ala  Val  Lys  Lys  Leu  Asp  Thr  Asn  Asp  Phe  Phe
                    195                 200                 205 gta  gaa  cca  gat  att  tgg  gat  tta  ttg  gac  aaa  gtt  cga  gat  atc  gct       672
Val  Glu  Pro  Asp  Ile  Trp  Asp  Leu  Leu  Asp  Lys  Val  Arg  Asp  Ile  Ala
210                 215                 220 gct  gag  tat  ggg  aca  gag  ctc  tta  cct  gag  att  cat  gaa  cat  tat  tcg       720
Ala  Glu  Tyr  Gly  Thr  Glu  Leu  Leu  Pro  Glu  Ile  His  Glu  His  Tyr  Ser
225                 230                 235                 240 att  cag  ttt  aaa  ata  gca  gac  cat  gat  tac  tat  gtt  tat  gat  ttt  gct       768
Ile  Gln  Phe  Lys  Ile  Ala  Asp  His  Asp  Tyr  Tyr  Val  Tyr  Asp  Phe  Ala
          245                 250                 255 ctt  cca  atg  gtg  aca  ctt  tat  act  ctt  tac  agt  tcc  aga  aca  gag  cgt       816
Leu  Pro  Met  Val  Thr  Leu  Tyr  Thr  Leu  Tyr  Ser  Ser  Arg  Thr  Glu  Arg
               260                 265                 270 ttg  gct  aag  tgg  tta  aag  atg  agc  cca  atg  aag  caa  ttt  acg  acg  cta       864
Leu  Ala  Lys  Trp  Leu  Lys  Met  Ser  Pro  Met  Lys  Gln  Phe  Thr  Thr  Leu
                    275                 280                 285 gac  acc  cat  gat  ggg  att  gga  gtg  gtg  gat  gtc  aag  gat  atc  ttg  aca       912
Asp  Thr  His  Asp  Gly  Ile  Gly  Val  Val  Asp  Val  Lys  Asp  Ile  Leu  Thr
290                 295                 300 gat  gag  gag  att  gac  tat  gct  tca  aat  gaa  ctc  tat  aag  gtt  gga  gct       960
Asp  Glu  Glu  Ile  Asp  Tyr  Ala  Ser  Asn  Glu  Leu  Tyr  Lys  Val  Gly  Ala
305                 310                 315                 320 aat  gtc  aaa  cgt  aag  tac  tcc  agt  gcc  gag  tat  aat  aat  tta  gat  atc       1008
Asn  Val  Lys  Arg  Lys  Tyr  Ser  Ser  Ala  Glu  Tyr  Asn  Asn  Leu  Asp  Ile
          325                 330                 335 tac  caa  atc  aat  tca  acc  tat  tat  tct  gcg  ctt  gga  gat  gat  gat  gtc       1056
Tyr  Gln  Ile  Asn  Ser  Thr  Tyr  Tyr  Ser  Ala  Leu  Gly  Asp  Asp  Asp  Val
               340                 345                 350 aag  tat  ttc  ctt  gca  cga  tta  att  caa  gca  ttt  gct  cca  ggt  att  cct       1104
Lys  Tyr  Phe  Leu  Ala  Arg  Leu  Ile  Gln  Ala  Phe  Ala  Pro  Gly  Ile  Pro
                    355                 360                 365 caa  gtt  tac  tat  gta  ggt  cta  tta  gca  ggc  aag  aat  gat  ttg  aaa  tta       1152
Gln  Val  Tyr  Tyr  Val  Gly  Leu  Leu  Ala  Gly  Lys  Asn  Asp  Leu  Lys  Leu
370                 375                 380 tta  gaa  gaa  act  aaa  gta  ggt  cga  aat  att  aat  cgt  cat  tac  tat  agc       1200
Leu  Glu  Glu  Thr  Lys  Val  Gly  Arg  Asn  Ile  Asn  Arg  His  Tyr  Tyr  Ser
385                 390                 395                 400 aat  gag  gaa  ata  gca  gaa  gaa  gtc  caa  cgt  cct  gta  gtg  aag  gcc  ctt       1248
Asn  Glu  Glu  Ile  Ala  Glu  Glu  Val  Gln  Arg  Pro  Val  Val  Lys  Ala  Leu
          405                 410                 415 ctc  aat  cta  ttt  tct  ttc  cgt  aat  cga  tca  gta  gca  ttt  gat  tta  gaa       1296
Leu  Asn  Leu  Phe  Ser  Phe  Arg  Asn  Arg  Ser  Val  Ala  Phe  Asp  Leu  Glu
               420                 425                 430 gga  act  att  gac  gtt  gaa  aca  cca  aca  gcc  cac  agc  att  gta  atc  aaa       1344
Gly  Thr  Ile  Asp  Val  Glu  Thr  Pro  Thr  Ala  His  Ser  Ile  Val  Ile  Lys
```

```
                   435                 440                 445
cgt caa aat aaa gat aag tcc gta aca gca gta gca gaa att gat ttg      1392
Arg Gln Asn Lys Asp Lys Ser Val Thr Ala Val Ala Glu Ile Asp Leu
450                 455                 460 caa aat cag act tat cga gta atg aga acg gaa tgg aag tac att ttg      1440
Gln Asn Gln Thr Tyr Arg Val Met Arg Thr Glu Trp Lys Tyr Ile Leu
465                 470                 475                 480 aag act                                                               1446
Lys Thr <210> SEQ ID NO 12
<211> LENGTH: 482
<212> TYPE: PRT
<213> ORGANISM: Streptococcus mitis

<400> SEQUENCE: 12

Met Pro Ile Gln Asn Lys Thr Met Leu Ile Thr Tyr Ser Asp Ser Leu
1               5                   10                  15

Gly Asn Asn Leu Lys Asp Leu Tyr Glu Asn Leu Glu Glu Tyr Phe Gly
                20                  25                  30

Asp Ala Ile Gly Gly Val His Leu Leu Pro Phe Phe Pro Ser Thr Gly
            35                  40                  45

Asp Arg Gly Phe Ala Pro Val Asp Tyr Asp Glu Val Asp Ser Ala Phe
        50                  55                  60

Gly Asp Trp Glu Asp Val Lys Arg Leu Gly Glu Lys Tyr Tyr Leu Met
65                  70                  75                  80

Phe Asp Phe Met Ile Asn His Ile Ser Arg Gln Ser Lys Tyr Tyr Lys
                85                  90                  95

Asp Tyr Gln Glu Lys His Glu Ala Ser Glu Phe Lys Asp Leu Phe Leu
            100                 105                 110

Asn Trp Asp Lys Phe Trp Pro Glu Asn Arg Pro Thr Gln Ser Asp Val
        115                 120                 125

Asp Leu Ile Tyr Lys Arg Lys Asp Arg Ala Pro Lys Gln Glu Ile Val
    130                 135                 140

Phe Glu Asp Gly Ser Val Glu His Leu Trp Asn Thr Phe Gly Glu Glu
145                 150                 155                 160

Gln Ile Asp Leu Asp Val Thr Lys Glu Val Thr Met Glu Phe Ile Arg
                165                 170                 175

Lys Thr Ile Gln His Leu Ala Ser Asn Gly Cys Asp Leu Ile Arg Leu
            180                 185                 190

Asp Ala Phe Ala Tyr Ala Val Lys Lys Leu Asp Thr Asn Asp Phe Phe
        195                 200                 205

Val Glu Pro Asp Ile Trp Asp Leu Leu Asp Lys Val Arg Asp Ile Ala
    210                 215                 220

Ala Glu Tyr Gly Thr Glu Leu Leu Pro Glu Ile His Glu His Tyr Ser
225                 230                 235                 240

Ile Gln Phe Lys Ile Ala Asp His Asp Tyr Tyr Val Tyr Asp Phe Ala
                245                 250                 255

Leu Pro Met Val Thr Leu Tyr Thr Leu Tyr Ser Ser Arg Thr Glu Arg
            260                 265                 270

Leu Ala Lys Trp Leu Lys Met Ser Pro Met Lys Gln Phe Thr Thr Leu
        275                 280                 285

Asp Thr His Asp Gly Ile Gly Val Val Asp Lys Asp Ile Leu Thr
    290                 295                 300

Asp Glu Glu Ile Asp Tyr Ala Ser Asn Glu Leu Tyr Lys Val Gly Ala
305                 310                 315                 320
```

```
Asn Val Lys Arg Lys Tyr Ser Ser Ala Glu Tyr Asn Asn Leu Asp Ile
            325                 330                 335
Tyr Gln Ile Asn Ser Thr Tyr Tyr Ser Ala Leu Gly Asp Asp Val
        340                 345                 350
Lys Tyr Phe Leu Ala Arg Leu Ile Gln Ala Phe Ala Pro Gly Ile Pro
            355                 360                 365
Gln Val Tyr Tyr Val Gly Leu Leu Ala Gly Lys Asn Asp Leu Lys Leu
    370                 375                 380
Leu Glu Glu Thr Lys Val Gly Arg Asn Ile Asn Arg His Tyr Tyr Ser
385                 390                 395                 400
Asn Glu Glu Ile Ala Glu Val Gln Arg Pro Val Lys Ala Leu
                405                 410                 415
Leu Asn Leu Phe Ser Phe Arg Asn Arg Ser Val Ala Phe Asp Leu Glu
            420                 425                 430
Gly Thr Ile Asp Val Glu Thr Pro Thr Ala His Ser Ile Val Ile Lys
            435                 440                 445
Arg Gln Asn Lys Asp Lys Ser Val Thr Ala Val Ala Glu Ile Asp Leu
            450                 455                 460
Gln Asn Gln Thr Tyr Arg Val Met Arg Thr Glu Trp Lys Tyr Ile Leu
465                 470                 475                 480
Lys Thr

<210> SEQ ID NO 13
<211> LENGTH: 1458
<212> TYPE: DNA
<213> ORGANISM: Leuconostoc mesenteroides
<220> FEATURE:
<221> NAME/KEY: CDS
<222> LOCATION: (1)..(1458)

<400> SEQUENCE: 13 atg gaa att caa aac aaa gca atg ctc att acg tat gct gat tct ttg      48
Met Glu Ile Gln Asn Lys Ala Met Leu Ile Thr Tyr Ala Asp Ser Leu
1               5                   10                  15 ggc agt aat atc aag gaa gtc cac caa gtt ttg aag gaa gac att ggc      96
Gly Ser Asn Ile Lys Glu Val His Gln Val Leu Lys Glu Asp Ile Gly
            20                  25                  30 gat gcg att ggc ggg gta cat ttg tta cca ttt ttc cct tct aca ggt     144
Asp Ala Ile Gly Gly Val His Leu Leu Pro Phe Phe Pro Ser Thr Gly
        35                  40                  45 gat cgt ggc ttc gcc cct tct gat tac acg cgt gtt gat gca aca ttt     192
Asp Arg Gly Phe Ala Pro Ser Asp Tyr Thr Arg Val Asp Ala Thr Phe
    50                  55                  60 ggt gat tgg aat gat gtt gag gca ctt ggg caa gaa tac tat ttg atg     240
Gly Asp Trp Asn Asp Val Glu Ala Leu Gly Gln Glu Tyr Tyr Leu Met
65                  70                  75                  80 ttt gat ttt atg atc aat cat att tct cgt gaa tcg gag atg tat caa     288
Phe Asp Phe Met Ile Asn His Ile Ser Arg Glu Ser Glu Met Tyr Gln
                85                  90                  95 gat ttt aaa gca aat cac gat caa tca aag tac cgt gat ttc ttc att     336
Asp Phe Lys Ala Asn His Asp Gln Ser Lys Tyr Arg Asp Phe Phe Ile
            100                 105                 110 cgc tgg gaa aag ttt tgg caa cag gct ggg cca gat cga cca act caa     384
Arg Trp Glu Lys Phe Trp Gln Gln Ala Gly Pro Asp Arg Pro Thr Gln
        115                 120                 125 gca gac gtc gac ctt att tat aag cgc aaa gac aag gcg cca att caa     432
Ala Asp Val Asp Leu Ile Tyr Lys Arg Lys Asp Lys Ala Pro Ile Gln
    130                 135                 140
```

-continued

| | | |
|---|---|---|
| gaa atc act ttt gct gac ggt acg aca gag cat ctt tgg aat aca ttt<br>Glu Ile Thr Phe Ala Asp Gly Thr Thr Glu His Leu Trp Asn Thr Phe<br>145                      150                      155                      160 | | 480 |
| ggt gaa gaa caa att gat att gat gtt aat tct caa att gct aaa gcc<br>Gly Glu Glu Gln Ile Asp Ile Asp Val Asn Ser Gln Ile Ala Lys Ala<br>                      165                      170                      175 | | 528 |
| ttc att aaa gca acg cta gaa gac atg gtc caa cat ggt gcc aat ttg<br>Phe Ile Lys Ala Thr Leu Glu Asp Met Val Gln His Gly Ala Asn Leu<br>                180                      185                      190 | | 576 |
| att cgt tta gat gct ttc gcc tat gct gtt aag aaa gtt ggg aca aat<br>Ile Arg Leu Asp Ala Phe Ala Tyr Ala Val Lys Lys Val Gly Thr Asn<br>195                      200                      205 | | 624 |
| gat ttc ttt gtc gaa cca gaa ata tgg act gtt tta aac gaa gtg cgt<br>Asp Phe Phe Val Glu Pro Glu Ile Trp Thr Val Leu Asn Glu Val Arg<br>    210                      215                      220 | | 672 |
| gac att ttg gca cct atg cat gct gaa att tta cca gaa att cat gag<br>Asp Ile Leu Ala Pro Met His Ala Glu Ile Leu Pro Glu Ile His Glu<br>225                      230                      235                      240 | | 720 |
| cat tat aca att cct caa aag atc aac gcc cat ggt tat ttc act tat<br>His Tyr Thr Ile Pro Gln Lys Ile Asn Ala His Gly Tyr Phe Thr Tyr<br>                245                      250                      255 | | 768 |
| gat ttt gct ttg cca atg aca gta ctt tat acg ctt tac tca ggc aaa<br>Asp Phe Ala Leu Pro Met Thr Val Leu Tyr Thr Leu Tyr Ser Gly Lys<br>                      260                      265                      270 | | 816 |
| aca aat cga cta gcc aac tgg ctc aaa cag tct ccg atg aaa caa ttc<br>Thr Asn Arg Leu Ala Asn Trp Leu Lys Gln Ser Pro Met Lys Gln Phe<br>        275                      280                      285 | | 864 |
| acg acg tta gat acg cat gat ggc att ggg gtt gtt gac gca cgt gat<br>Thr Thr Leu Asp Thr His Asp Gly Ile Gly Val Val Asp Ala Arg Asp<br>290                      295                      300 | | 912 |
| att ttg aca gac gaa gaa att gat tat gct tct gag gaa tta tac aaa<br>Ile Leu Thr Asp Glu Glu Ile Asp Tyr Ala Ser Glu Glu Leu Tyr Lys<br>305                      310                      315                      320 | | 960 |
| gtt gga gcc aat gtc aaa aag acc tac tca tca gct gcg tat aat aac<br>Val Gly Ala Asn Val Lys Lys Thr Tyr Ser Ser Ala Ala Tyr Asn Asn<br>                      325                      330                      335 | | 1008 |
| tta gat att tat cag att aat tca act tac tat tca gct tta ggc aat<br>Leu Asp Ile Tyr Gln Ile Asn Ser Thr Tyr Tyr Ser Ala Leu Gly Asn<br>                340                      345                      350 | | 1056 |
| gat gat gcc gca tat ttg ttg agt cgt gtt ttc caa gtc ttt gca cct<br>Asp Asp Ala Ala Tyr Leu Leu Ser Arg Val Phe Gln Val Phe Ala Pro<br>            355                      360                      365 | | 1104 |
| ggt att cca caa att tat tat gtc ggg tta ctt gca ggt gag aat gat<br>Gly Ile Pro Gln Ile Tyr Tyr Val Gly Leu Leu Ala Gly Glu Asn Asp<br>370                      375                      380 | | 1152 |
| att gat ttg ttg gaa tct tca aaa gaa ggt cgt aat att aat cgt cat<br>Ile Asp Leu Leu Glu Ser Ser Lys Glu Gly Arg Asn Ile Asn Arg His<br>385                      390                      395                      400 | | 1200 |
| tac tat act cgt gaa gaa ata aaa tca gct gtt aag cgg cca gtt gtt<br>Tyr Tyr Thr Arg Glu Glu Ile Lys Ser Ala Val Lys Arg Pro Val Val<br>                      405                      410                      415 | | 1248 |
| gct gac tta ttg gca tta tta tca tgg cgt aat cag ttt tca gca ttt<br>Ala Asp Leu Leu Ala Leu Leu Ser Trp Arg Asn Gln Phe Ser Ala Phe<br>                      420                      425                      430 | | 1296 |
| gct ctg gat ggg aca atc act gtc gag aca cca tca gaa cat gat att<br>Ala Leu Asp Gly Thr Ile Thr Val Glu Thr Pro Ser Glu His Asp Ile<br>                435                      440                      445 | | 1344 |
| aaa att aca cga acg gat cat tcc gga gat aat ata gct att ttg cta<br>Lys Ile Thr Arg Thr Asp His Ser Gly Asp Asn Ile Ala Ile Leu Leu<br>450                      455                      460 | | 1392 |

```
gct aat gcc aag aca cgc acc ttt gtc atc aca gca aat ggc aag aca    1440
Ala Asn Ala Lys Thr Arg Thr Phe Val Ile Thr Ala Asn Gly Lys Thr
465                 470                 475                 480 gtc tta caa aac aaa taa                                            1458
Val Leu Gln Asn Lys
            485
```

<210> SEQ ID NO 14
<211> LENGTH: 485
<212> TYPE: PRT
<213> ORGANISM: Leuconostoc mesenteroides
<400> SEQUENCE: 14

```
Met Glu Ile Gln Asn Lys Ala Met Leu Ile Thr Tyr Ala Asp Ser Leu
1               5                   10                  15

Gly Ser Asn Ile Lys Glu Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ser Asp Tyr Thr Arg Val Asp Ala Thr Phe
    50                  55                  60

Gly Asp Trp Asn Asp Val Glu Ala Leu Gly Gln Glu Tyr Tyr Leu Met
65                  70                  75                  80

Phe Asp Phe Met Ile Asn His Ile Ser Arg Glu Ser Glu Met Tyr Gln
                85                  90                  95

Asp Phe Lys Ala Asn His Asp Gln Ser Lys Tyr Arg Asp Phe Phe Ile
            100                 105                 110

Arg Trp Glu Lys Phe Trp Gln Gln Ala Gly Pro Asp Arg Pro Thr Gln
        115                 120                 125

Ala Asp Val Asp Leu Ile Tyr Lys Arg Lys Asp Lys Ala Pro Ile Gln
    130                 135                 140

Glu Ile Thr Phe Ala Asp Gly Thr Thr Glu His Leu Trp Asn Thr Phe
145                 150                 155                 160

Gly Glu Glu Gln Ile Asp Ile Asp Val Asn Ser Gln Ile Ala Lys Ala
                165                 170                 175

Phe Ile Lys Ala Thr Leu Glu Asp Met Val Gln His Gly Ala Asn Leu
            180                 185                 190

Ile Arg Leu Asp Ala Phe Ala Tyr Ala Val Lys Lys Val Gly Thr Asn
        195                 200                 205

Asp Phe Phe Val Glu Pro Glu Ile Trp Thr Val Leu Asn Glu Val Arg
    210                 215                 220

Asp Ile Leu Ala Pro Met His Ala Glu Ile Leu Pro Glu Ile His Glu
225                 230                 235                 240

His Tyr Thr Ile Pro Gln Lys Ile Asn Ala His Gly Tyr Phe Thr Tyr
                245                 250                 255

Asp Phe Ala Leu Pro Met Thr Val Leu Tyr Thr Leu Tyr Ser Gly Lys
            260                 265                 270

Thr Asn Arg Leu Ala Asn Trp Leu Lys Gln Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Glu Glu Ile Asp Tyr Ala Ser Glu Glu Leu Tyr Lys
305                 310                 315                 320

Val Gly Ala Asn Val Lys Lys Thr Tyr Ser Ser Ala Ala Tyr Asn Asn
                325                 330                 335

Leu Asp Ile Tyr Gln Ile Asn Ser Thr Tyr Tyr Ser Ala Leu Gly Asn
```

```
            340                 345                 350
Asp Asp Ala Ala Tyr Leu Leu Ser Arg Val Phe Gln Val Phe Ala Pro
            355                 360                 365
Gly Ile Pro Gln Ile Tyr Tyr Val Gly Leu Leu Ala Gly Glu Asn Asp
        370                 375                 380
Ile Asp Leu Leu Glu Ser Ser Lys Glu Gly Arg Asn Ile Asn Arg His
385                 390                 395                 400
Tyr Tyr Thr Arg Glu Glu Ile Lys Ser Ala Val Lys Arg Pro Val Val
                405                 410                 415
Ala Asp Leu Leu Ala Leu Leu Ser Trp Arg Asn Gln Phe Ser Ala Phe
            420                 425                 430
Ala Leu Asp Gly Thr Ile Thr Val Glu Thr Pro Ser Glu His Asp Ile
            435                 440                 445
Lys Ile Thr Arg Thr Asp His Ser Gly Asp Asn Ile Ala Ile Leu Leu
            450                 455                 460
Ala Asn Ala Lys Thr Arg Thr Phe Val Ile Thr Ala Asn Gly Lys Thr
465                 470                 475                 480
Val Leu Gln Asn Lys
                485

<210> SEQ ID NO 15
<211> LENGTH: 1443
<212> TYPE: DNA
<213> ORGANISM: Lactobacillus acidophilus
<220> FEATURE:
<221> NAME/KEY: CDS
<222> LOCATION: (1)..(1443)

<400> SEQUENCE: 15 atg aaa tta caa aat aag gca ata ttg ata act tat cca gat agt tta        48
Met Lys Leu Gln Asn Lys Ala Ile Leu Ile Thr Tyr Pro Asp Ser Leu
1               5                   10                  15 ggt cat aat ttg aag gac ttg gat cat gta atg gat cgc tat ttt aat       96
Gly His Asn Leu Lys Asp Leu Asp His Val Met Asp Arg Tyr Phe Asn
                20                  25                  30 aaa acg ata ggt ggt att cat tta tta cca ttt ttc cct tca aac ggt      144
Lys Thr Ile Gly Gly Ile His Leu Leu Pro Phe Phe Pro Ser Asn Gly
            35                  40                  45 gat cgc ggt ttt tct cct aca aga tat gat gta gtt gag cct aag ttt      192
Asp Arg Gly Phe Ser Pro Thr Arg Tyr Asp Val Val Glu Pro Lys Phe
        50                  55                  60 ggt tca tgg gaa gat gta gaa aag tta agt caa aag tat tat ttg atg      240
Gly Ser Trp Glu Asp Val Glu Lys Leu Ser Gln Lys Tyr Tyr Leu Met
65                  70                  75                  80 ttt gac ttt atg att aat cat ctt tct aaa aaa tcc tca tat ttt gaa      288
Phe Asp Phe Met Ile Asn His Leu Ser Lys Lys Ser Ser Tyr Phe Glu
                85                  90                  95 gat ttt gaa gcc aag cac gat aaa agc aaa tat agc gat ctt ttc tta      336
Asp Phe Glu Ala Lys His Asp Lys Ser Lys Tyr Ser Asp Leu Phe Leu
                100                 105                 110 agt tgg gat aaa ttt tgg cca aag ggc aga cca act aaa gaa gat ata      384
Ser Trp Asp Lys Phe Trp Pro Lys Gly Arg Pro Thr Lys Glu Asp Ile
            115                 120                 125 gat tta att tat aaa cga aaa gat aag gcc cca tat caa aat att aaa      432
Asp Leu Ile Tyr Lys Arg Lys Asp Lys Ala Pro Tyr Gln Asn Ile Lys
        130                 135                 140 ttt gaa gat ggt act cat gaa aag atg tgg aat act ttc ggc cca gat      480
Phe Glu Asp Gly Thr His Glu Lys Met Trp Asn Thr Phe Gly Pro Asp
145                 150                 155                 160
```

-continued

```
caa atg gat ttg gat gtt aga acc aag aca aca caa gat ttt ata aag    528
Gln Met Asp Leu Asp Val Arg Thr Lys Thr Thr Gln Asp Phe Ile Lys
            165                 170                 175 cat aat tta caa aat ctt tct aaa cat ggt gct agt ttg att cgt tta    576
His Asn Leu Gln Asn Leu Ser Lys His Gly Ala Ser Leu Ile Arg Leu
        180                 185                 190 gat gca ttt gct tat gca att aaa aag tta gat aca aat gac ttc ttt    624
Asp Ala Phe Ala Tyr Ala Ile Lys Lys Leu Asp Thr Asn Asp Phe Phe
    195                 200                 205 gta gaa ccg gaa att tgg aat tta ctc gaa aag gta aat gat tat ctt    672
Val Glu Pro Glu Ile Trp Asn Leu Leu Glu Lys Val Asn Asp Tyr Leu
210                 215                 220 aaa gat act cca act act att ctg cct gaa att cat gag cat tat acg    720
Lys Asp Thr Pro Thr Thr Ile Leu Pro Glu Ile His Glu His Tyr Thr
225                 230                 235                 240 atg cca ttt aag gtg gca gaa cat gga tac ttt att tat gat ttt gct    768
Met Pro Phe Lys Val Ala Glu His Gly Tyr Phe Ile Tyr Asp Phe Ala
                245                 250                 255 tta cca atg gta ttg ttg tat tca ctt tat agc ggt aat agt act caa    816
Leu Pro Met Val Leu Leu Tyr Ser Leu Tyr Ser Gly Asn Ser Thr Gln
            260                 265                 270 ctt gct gct tgg cta aag aaa tgt ccg atg aag caa ttt act act tta    864
Leu Ala Ala Trp Leu Lys Lys Cys Pro Met Lys Gln Phe Thr Thr Leu
        275                 280                 285 gat acc cac gat gga tta ggc gta gtt gac gca aag gat att ctt acg    912
Asp Thr His Asp Gly Leu Gly Val Val Asp Ala Lys Asp Ile Leu Thr
    290                 295                 300 gac gat caa att agc tac aca aca aac gaa ctt tat aaa att ggt gct    960
Asp Asp Gln Ile Ser Tyr Thr Thr Asn Glu Leu Tyr Lys Ile Gly Ala
305                 310                 315                 320 aac gtc aag aag aaa tat tct agt gct gaa tat cat aat ttg gat att   1008
Asn Val Lys Lys Lys Tyr Ser Ser Ala Glu Tyr His Asn Leu Asp Ile
                325                 330                 335 tat caa att aat act act tat tat tct gca ttg ggt aat gat gat aaa   1056
Tyr Gln Ile Asn Thr Thr Tyr Tyr Ser Ala Leu Gly Asn Asp Asp Lys
            340                 345                 350 aaa tat ttt att gca cgg tta tta caa atc ttt gcc cct ggt att cca   1104
Lys Tyr Phe Ile Ala Arg Leu Leu Gln Ile Phe Ala Pro Gly Ile Pro
        355                 360                 365 caa att tat tat gtt gga ttg tta gca gga gaa aat gat att caa tta   1152
Gln Ile Tyr Tyr Val Gly Leu Leu Ala Gly Glu Asn Asp Ile Gln Leu
    370                 375                 380 tta gag aag aca aaa gaa gga cgc gat att aat cgc cac tat tat gat   1200
Leu Glu Lys Thr Lys Glu Gly Arg Asp Ile Asn Arg His Tyr Tyr Asp
385                 390                 395                 400 ttg gat gag att gcg gaa caa gtt caa aga cct gta gta aaa tct ttg   1248
Leu Asp Glu Ile Ala Glu Gln Val Gln Arg Pro Val Val Lys Ser Leu
                405                 410                 415 att aag tta ttg gaa ttt cgt aat tct gta cct gca ttt gat ttg gaa   1296
Ile Lys Leu Leu Glu Phe Arg Asn Ser Val Pro Ala Phe Asp Leu Glu
            420                 425                 430 ggt tca atc aaa gtt gaa act cca agt gaa cat gaa att att gtc act   1344
Gly Ser Ile Lys Val Glu Thr Pro Ser Glu His Glu Ile Ile Val Thr
        435                 440                 445 aga tca aat aag gca gga aca gaa gta gct agt acg tac gta gac ttt   1392
Arg Ser Asn Lys Ala Gly Thr Glu Val Ala Ser Thr Tyr Val Asp Phe
    450                 455                 460 aag aac tta gac tat caa gtt aaa tac aat gat cag gtc ttt aat ttt   1440
Lys Asn Leu Asp Tyr Gln Val Lys Tyr Asn Asp Gln Val Phe Asn Phe
465                 470                 475                 480
``` tag                                                                 1443

<210> SEQ ID NO 16
<211> LENGTH: 480
<212> TYPE: PRT
<213> ORGANISM: Lactobacillus acidophilus

<400> SEQUENCE: 16

Met Lys Leu Gln Asn Lys Ala Ile Leu Ile Thr Tyr Pro Asp Ser Leu
1               5                   10                  15

Gly His Asn Leu Lys Asp Leu Asp His Val Met Asp Arg Tyr Phe Asn
            20                  25                  30

Lys Thr Ile Gly Gly Ile His Leu Leu Pro Phe Phe Pro Ser Asn Gly
        35                  40                  45

Asp Arg Gly Phe Ser Pro Thr Arg Tyr Asp Val Val Glu Pro Lys Phe
    50                  55                  60

Gly Ser Trp Glu Asp Val Glu Lys Leu Ser Gln Lys Tyr Tyr Leu Met
65                  70                  75                  80

Phe Asp Phe Met Ile Asn His Leu Ser Lys Lys Ser Ser Tyr Phe Glu
                85                  90                  95

Asp Phe Glu Ala Lys His Asp Lys Ser Lys Tyr Ser Asp Leu Phe Leu
            100                 105                 110

Ser Trp Asp Lys Phe Trp Pro Lys Gly Arg Pro Thr Lys Glu Asp Ile
        115                 120                 125

Asp Leu Ile Tyr Lys Arg Lys Asp Lys Ala Pro Tyr Gln Asn Ile Lys
    130                 135                 140

Phe Glu Asp Gly Thr His Glu Lys Met Trp Asn Thr Phe Gly Pro Asp
145                 150                 155                 160

Gln Met Asp Leu Asp Val Arg Thr Lys Thr Thr Gln Asp Phe Ile Lys
                165                 170                 175

His Asn Leu Gln Asn Leu Ser Lys His Gly Ala Ser Leu Ile Arg Leu
            180                 185                 190

Asp Ala Phe Ala Tyr Ala Ile Lys Lys Leu Asp Thr Asn Asp Phe Phe
        195                 200                 205

Val Glu Pro Glu Ile Trp Asn Leu Leu Glu Lys Val Asn Asp Tyr Leu
    210                 215                 220

Lys Asp Thr Pro Thr Thr Ile Leu Pro Glu Ile His Glu His Tyr Thr
225                 230                 235                 240

Met Pro Phe Lys Val Ala Glu His Gly Tyr Phe Ile Tyr Asp Phe Ala
                245                 250                 255

Leu Pro Met Val Leu Leu Tyr Ser Leu Tyr Ser Gly Asn Ser Thr Gln
            260                 265                 270

Leu Ala Ala Trp Leu Lys Lys Cys Pro Met Lys Gln Phe Thr Thr Leu
        275                 280                 285

Asp Thr His Asp Gly Leu Gly Val Val Asp Ala Lys Asp Ile Leu Thr
    290                 295                 300

Asp Asp Gln Ile Ser Tyr Thr Thr Asn Glu Leu Tyr Lys Ile Gly Ala
305                 310                 315                 320

Asn Val Lys Lys Lys Tyr Ser Ser Ala Glu Tyr His Asn Leu Asp Ile
                325                 330                 335

Tyr Gln Ile Asn Thr Thr Tyr Ser Ala Leu Gly Asn Asp Asp Lys
            340                 345                 350

Lys Tyr Phe Ile Ala Arg Leu Leu Gln Ile Phe Ala Pro Gly Ile Pro
        355                 360                 365

Gln Ile Tyr Tyr Val Gly Leu Leu Ala Gly Glu Asn Asp Ile Gln Leu

```
                   370                 375                 380
Leu Glu Lys Thr Lys Glu Gly Arg Asp Ile Asn Arg His Tyr Tyr Asp
385                 390                 395                 400

Leu Asp Glu Ile Ala Glu Gln Val Gln Arg Pro Val Val Lys Ser Leu
                405                 410                 415

Ile Lys Leu Leu Glu Phe Arg Asn Ser Val Pro Ala Phe Asp Leu Glu
                420                 425                 430

Gly Ser Ile Lys Val Glu Thr Pro Ser Glu His Glu Ile Ile Val Thr
                435                 440                 445

Arg Ser Asn Lys Ala Gly Thr Glu Val Ala Ser Thr Tyr Val Asp Phe
450                 455                 460

Lys Asn Leu Asp Tyr Gln Val Lys Tyr Asn Asp Gln Val Phe Asn Phe
465                 470                 475                 480

<210> SEQ ID NO 17
<211> LENGTH: 1443
<212> TYPE: DNA
<213> ORGANISM: Lactobacillus acidophilus
<220> FEATURE:
<221> NAME/KEY: CDS
<222> LOCATION: (1)..(1443)

<400> SEQUENCE: 17 atg cca att gaa aat aaa gta atg tta att act tat cca gac agt ttg      48
Met Pro Ile Glu Asn Lys Val Met Leu Ile Thr Tyr Pro Asp Ser Leu
1               5                  10                  15 ggt aaa aat tta aaa gaa tta gat gaa att tta agt gaa gac ttg aag      96
Gly Lys Asn Leu Lys Glu Leu Asp Glu Ile Leu Ser Glu Asp Leu Lys
            20                  25                  30 ggg gct gta ggc ggt att cac tta ttg cca ttc ttc cca tca act ggt     144
Gly Ala Val Gly Gly Ile His Leu Leu Pro Phe Phe Pro Ser Thr Gly
        35                  40                  45 gac cgt gga ttt gct ccg act gga tat aca gaa gta gat cct aag ttt     192
Asp Arg Gly Phe Ala Pro Thr Gly Tyr Thr Glu Val Asp Pro Lys Phe
    50                  55                  60 ggt gat tgg tca gac att gaa aaa ata ggt aag aaa tat tat ttg atg     240
Gly Asp Trp Ser Asp Ile Glu Lys Ile Gly Lys Lys Tyr Tyr Leu Met
65                  70                  75                  80 ttt gat ttt atg att aat cat att tct cgt caa tca aaa ttt tat aaa     288
Phe Asp Phe Met Ile Asn His Ile Ser Arg Gln Ser Lys Phe Tyr Lys
                85                  90                  95 gat ttc aaa caa aag aaa gat aaa agt aag tat gcc gat tta ttt ttg     336
Asp Phe Lys Gln Lys Lys Asp Lys Ser Lys Tyr Ala Asp Leu Phe Leu
            100                 105                 110 agc tgg gac aaa ttt tgg ccg gaa ggt cgt cca act cga aaa gat att     384
Ser Trp Asp Lys Phe Trp Pro Glu Gly Arg Pro Thr Arg Lys Asp Ile
        115                 120                 125 gat tta att tat aaa cga aaa gat cgt gct cca tat caa gaa att act     432
Asp Leu Ile Tyr Lys Arg Lys Asp Arg Ala Pro Tyr Gln Glu Ile Thr
    130                 135                 140 ttt aca gat ggc agt aaa gaa aaa tta tgg aat act ttt ggt gaa gag     480
Phe Thr Asp Gly Ser Lys Glu Lys Leu Trp Asn Thr Phe Gly Glu Glu
145                 150                 155                 160 caa atc gat atg gat gtt cga aag gag gtg aca cag aag ttt att aaa     528
Gln Ile Asp Met Asp Val Arg Lys Glu Val Thr Gln Lys Phe Ile Lys
                165                 170                 175 gat acg ttg aga gca tta att gat cat ggt gct gat att att cgg tta     576
Asp Thr Leu Arg Ala Leu Ile Asp His Gly Ala Asp Ile Ile Arg Leu
            180                 185                 190 gat gct ttt gcg tat gct gta aag aag tta gat act aat gat ttc ttt     624
```

```
Asp Ala Phe Ala Tyr Ala Val Lys Lys Leu Asp Thr Asn Asp Phe Phe
        195                 200                 205 gta gag cca gaa att tgg gat tta cta aaa caa gta caa gat gat att      672
Val Glu Pro Glu Ile Trp Asp Leu Leu Lys Gln Val Gln Asp Asp Ile
    210                 215                 220 tct gat aaa ggt gca atg att cta cca gaa ata cat gaa cac tat tca      720
Ser Asp Lys Gly Ala Met Ile Leu Pro Glu Ile His Glu His Tyr Ser
225                 230                 235                 240 atg cca ttt aag att tca aag cat gga tat tat atc tat gac ttt gct      768
Met Pro Phe Lys Ile Ser Lys His Gly Tyr Tyr Ile Tyr Asp Phe Ala
                245                 250                 255 tta cca atg gta act tta tat tca ctt tat tca ggt aag tcc aat cgc      816
Leu Pro Met Val Thr Leu Tyr Ser Leu Tyr Ser Gly Lys Ser Asn Arg
            260                 265                 270 tta gct gat tgg ctt aag aaa tgt cca atg aaa cag ttc act acc tta      864
Leu Ala Asp Trp Leu Lys Lys Cys Pro Met Lys Gln Phe Thr Thr Leu
        275                 280                 285 gat aca cat gat ggt atc ggt gtt gtt gat gct cgt gat att ctc tcc      912
Asp Thr His Asp Gly Ile Gly Val Val Asp Ala Arg Asp Ile Leu Ser
    290                 295                 300 cct gac gaa att aaa tac aca agt aat gaa ttg tat aaa gtt gga gct      960
Pro Asp Glu Ile Lys Tyr Thr Ser Asn Glu Leu Tyr Lys Val Gly Ala
305                 310                 315                 320 aat gtt aaa aag aaa tat tct agt gcc gaa tat cat aat tta gat atc     1008
Asn Val Lys Lys Lys Tyr Ser Ser Ala Glu Tyr His Asn Leu Asp Ile
                325                 330                 335 tac caa att aat aca act tat tat tct gct tta ggc aat gat gat aaa     1056
Tyr Gln Ile Asn Thr Thr Tyr Tyr Ser Ala Leu Gly Asn Asp Asp Lys
            340                 345                 350 aaa tac ttt att gcg aga ctt att caa atg ttt gcg cct ggt att ccg     1104
Lys Tyr Phe Ile Ala Arg Leu Ile Gln Met Phe Ala Pro Gly Ile Pro
        355                 360                 365 caa gtc tat tat gta gga atg ctg gct ggt aaa aac gat atc gaa ctc     1152
Gln Val Tyr Tyr Val Gly Met Leu Ala Gly Lys Asn Asp Ile Glu Leu
    370                 375                 380 ctc gaa aag act aaa gaa ggt aga aac att aat cgt cat tac tat ggc     1200
Leu Glu Lys Thr Lys Glu Gly Arg Asn Ile Asn Arg His Tyr Tyr Gly
385                 390                 395                 400 aga gaa gaa gta gct gaa gaa act aaa aga cct tta gta gca gca ctc     1248
Arg Glu Glu Val Ala Glu Glu Thr Lys Arg Pro Leu Val Ala Ala Leu
                405                 410                 415 ttg aaa ttg ttt aat ttt aga aac aat gaa gca gct ttt gat ctt gat     1296
Leu Lys Leu Phe Asn Phe Arg Asn Asn Glu Ala Ala Phe Asp Leu Asp
            420                 425                 430 gga tcc att gaa atc act acg cct aat gaa aac gtg att caa ata act     1344
Gly Ser Ile Glu Ile Thr Thr Pro Asn Glu Asn Val Ile Gln Ile Thr
        435                 440                 445 cgt atg aat aaa gat aaa act cga aaa gca aga gct gtt att aat tta     1392
Arg Met Asn Lys Asp Lys Thr Arg Lys Ala Arg Ala Val Ile Asn Leu
    450                 455                 460 aaa aat tta act tat caa gtg act gta aat aat gag gtt att aac ttt     1440
Lys Asn Leu Thr Tyr Gln Val Thr Val Asn Asn Glu Val Ile Asn Phe
465                 470                 475                 480 taa                                                                 1443
```

<210> SEQ ID NO 18
<211> LENGTH: 480
<212> TYPE: PRT
<213> ORGANISM: Lactobacillus acidophilus

<400> SEQUENCE: 18

-continued

```
Met Pro Ile Glu Asn Lys Val Met Leu Ile Thr Tyr Pro Asp Ser Leu
1               5                   10                  15

Gly Lys Asn Leu Lys Glu Leu Asp Glu Ile Leu Ser Glu Asp Leu Lys
            20                  25                  30

Gly Ala Val Gly Gly Ile His Leu Leu Pro Phe Phe Pro Ser Thr Gly
            35                  40                  45

Asp Arg Gly Phe Ala Pro Thr Gly Tyr Thr Glu Val Asp Pro Lys Phe
        50                  55                  60

Gly Asp Trp Ser Asp Ile Glu Lys Ile Gly Lys Lys Tyr Tyr Leu Met
65                  70                  75                  80

Phe Asp Phe Met Ile Asn His Ile Ser Arg Gln Ser Lys Phe Tyr Lys
                85                  90                  95

Asp Phe Lys Gln Lys Lys Asp Lys Ser Lys Tyr Ala Asp Leu Phe Leu
            100                 105                 110

Ser Trp Asp Lys Phe Trp Pro Glu Gly Arg Pro Thr Arg Lys Asp Ile
        115                 120                 125

Asp Leu Ile Tyr Lys Arg Lys Asp Arg Ala Pro Tyr Gln Glu Ile Thr
    130                 135                 140

Phe Thr Asp Gly Ser Lys Glu Lys Leu Trp Asn Thr Phe Gly Glu Glu
145                 150                 155                 160

Gln Ile Asp Met Asp Val Arg Lys Glu Val Thr Gln Lys Phe Ile Lys
                165                 170                 175

Asp Thr Leu Arg Ala Leu Ile Asp His Gly Ala Asp Ile Ile Arg Leu
            180                 185                 190

Asp Ala Phe Ala Tyr Ala Val Lys Lys Leu Asp Thr Asn Asp Phe Phe
        195                 200                 205

Val Glu Pro Glu Ile Trp Asp Leu Leu Lys Gln Val Gln Asp Asp Ile
    210                 215                 220

Ser Asp Lys Gly Ala Met Ile Leu Pro Glu Ile His Glu His Tyr Ser
225                 230                 235                 240

Met Pro Phe Lys Ile Ser Lys His Gly Tyr Tyr Ile Tyr Asp Phe Ala
                245                 250                 255

Leu Pro Met Val Thr Leu Tyr Ser Leu Tyr Ser Gly Lys Ser Asn Arg
            260                 265                 270

Leu Ala Asp Trp Leu Lys Lys Cys Pro Met Lys Gln Phe Thr Thr Leu
        275                 280                 285

Asp Thr His Asp Gly Ile Gly Val Val Asp Ala Arg Asp Ile Leu Ser
    290                 295                 300

Pro Asp Glu Ile Lys Tyr Thr Ser Asn Glu Leu Tyr Lys Val Gly Ala
305                 310                 315                 320

Asn Val Lys Lys Lys Tyr Ser Ser Ala Glu Tyr His Asn Leu Asp Ile
                325                 330                 335

Tyr Gln Ile Asn Thr Thr Tyr Ser Ala Leu Gly Asn Asp Asp Lys
            340                 345                 350

Lys Tyr Phe Ile Ala Arg Leu Ile Gln Met Phe Ala Pro Gly Ile Pro
        355                 360                 365

Gln Val Tyr Tyr Val Gly Met Leu Ala Gly Lys Asn Asp Ile Glu Leu
    370                 375                 380

Leu Glu Lys Thr Lys Glu Gly Arg Asn Ile Asn Arg His Tyr Tyr Gly
385                 390                 395                 400

Arg Glu Glu Val Ala Glu Glu Thr Lys Arg Pro Leu Val Ala Ala Leu
                405                 410                 415

Leu Lys Leu Phe Asn Phe Arg Asn Asn Glu Ala Ala Phe Asp Leu Asp
```

```
                        420              425             430
Gly Ser Ile Glu Ile Thr Thr Pro Asn Glu Asn Val Ile Gln Ile Thr
                435              440             445

Arg Met Asn Lys Asp Lys Thr Arg Lys Ala Arg Ala Val Ile Asn Leu
        450              455             460

Lys Asn Leu Thr Tyr Gln Val Thr Val Asn Asn Glu Val Ile Asn Phe
465             470              475             480

<210> SEQ ID NO 19
<211> LENGTH: 1443
<212> TYPE: DNA
<213> ORGANISM: Listeria monocytogenes
<220> FEATURE:
<221> NAME/KEY: CDS
<222> LOCATION: (1)..(1443)

<400> SEQUENCE: 19 atg caa att aaa aat aaa gct atg tta att act tat tct gat agt tta      48
Met Gln Ile Lys Asn Lys Ala Met Leu Ile Thr Tyr Ser Asp Ser Leu
1               5                   10                  15 ggg aaa aat atg gaa gaa tta tcc aag gtg atg gaa act tat ttt gaa      96
Gly Lys Asn Met Glu Glu Leu Ser Lys Val Met Glu Thr Tyr Phe Glu
                20                  25                  30 gat gct gtt ggc ggg att cac tta ttg ccg ttc ttt cca tcc act gga     144
Asp Ala Val Gly Gly Ile His Leu Leu Pro Phe Phe Pro Ser Thr Gly
            35                  40                  45 gat cga ggg ttt gcg cca agt gat tac aca aca gta gat agc gac cta     192
Asp Arg Gly Phe Ala Pro Ser Asp Tyr Thr Thr Val Asp Ser Asp Leu
        50                  55                  60 ggt tct tgg gaa ata atc gag aaa tta ggc gaa aag tat tat tta atg     240
Gly Ser Trp Glu Ile Ile Glu Lys Leu Gly Glu Lys Tyr Tyr Leu Met
65                  70                  75                  80 ttt gat ttt atg att aat cac att tct cgc gaa tca ctc ttc ttt caa     288
Phe Asp Phe Met Ile Asn His Ile Ser Arg Glu Ser Leu Phe Phe Gln
                85                  90                  95 gat ttt aaa aaa gag cat tta aac tca aag tat aaa gat atg ttt att     336
Asp Phe Lys Lys Glu His Leu Asn Ser Lys Tyr Lys Asp Met Phe Ile
                100                 105                 110 cgt atc aat gat ttc ttt cct ccg ggt aga cca aat gaa aaa gac tta     384
Arg Ile Asn Asp Phe Phe Pro Pro Gly Arg Pro Asn Glu Lys Asp Leu
            115                 120                 125 gat tta att tat aag aga aaa gat aag gcg cct ttt caa gaa gtt gaa     432
Asp Leu Ile Tyr Lys Arg Lys Asp Lys Ala Pro Phe Gln Glu Val Glu
        130                 135                 140 ttt gct gat ggg gga acg gaa tta gtt tgg aat act ttt ggg gaa gaa     480
Phe Ala Asp Gly Gly Thr Glu Leu Val Trp Asn Thr Phe Gly Glu Glu
145                 150                 155                 160 caa att gat tta gat gtg aca gcc gaa gtt aca aaa gaa ttt att cgt     528
Gln Ile Asp Leu Asp Val Thr Ala Glu Val Thr Lys Glu Phe Ile Arg
                165                 170                 175 caa acg ata aaa aat atg gct gca cat ggt tgt tct att ttg cgt ctt     576
Gln Thr Ile Lys Asn Met Ala Ala His Gly Cys Ser Ile Leu Arg Leu
                180                 185                 190 gat gcc ttt gct tat gca att aaa aaa tta gat aca aat gat ttt ttt     624
Asp Ala Phe Ala Tyr Ala Ile Lys Lys Leu Asp Thr Asn Asp Phe Phe
            195                 200                 205 gta gaa ccg gaa att tgg gat tta ctg gat gaa gtg aaa gca gaa gcg     672
Val Glu Pro Glu Ile Trp Asp Leu Leu Asp Glu Val Lys Ala Glu Ala
        210                 215                 220 gcc aaa tat gac atg gaa tta tta cca gaa att cat gaa cat tat tcc     720
Ala Lys Tyr Asp Met Glu Leu Leu Pro Glu Ile His Glu His Tyr Ser
```

```
                    225                 230                 235                 240
atc caa atg aaa atc gcg aac cat gat tat tat atc tat gat ttt gcg      768
Ile Gln Met Lys Ile Ala Asn His Asp Tyr Tyr Ile Tyr Asp Phe Ala
                245                 250                 255 tta ccc atg gtg atg ctg tac tcg tta tat agt ggc cga gtg gaa cgt      816
Leu Pro Met Val Met Leu Tyr Ser Leu Tyr Ser Gly Arg Val Glu Arg
            260                 265                 270 tta gct aaa tgg tta gaa atg agt ccg atg aag caa ttt act act tta      864
Leu Ala Lys Trp Leu Glu Met Ser Pro Met Lys Gln Phe Thr Thr Leu
        275                 280                 285 gat acg cat gat ggc att ggc gtt gtg gat gca cgc gat tta tta aca      912
Asp Thr His Asp Gly Ile Gly Val Val Asp Ala Arg Asp Leu Leu Thr
    290                 295                 300 gat gag gaa ctc gat tat act tca gca gaa tta tac aaa ata gga gct      960
Asp Glu Glu Leu Asp Tyr Thr Ser Ala Glu Leu Tyr Lys Ile Gly Ala
305                 310                 315                 320 aat gtt aaa aag ata tat tcc tct gaa aaa tat aat aac ctg gat att     1008
Asn Val Lys Lys Ile Tyr Ser Ser Glu Lys Tyr Asn Asn Leu Asp Ile
                325                 330                 335 tat caa att aat agt acc tat tat agt gct ttg ggt gac gat gat aaa     1056
Tyr Gln Ile Asn Ser Thr Tyr Tyr Ser Ala Leu Gly Asp Asp Asp Lys
            340                 345                 350 agt tac ttg tta gcg aga gta att caa tgt ttt gcg ccg ggg att ccg     1104
Ser Tyr Leu Leu Ala Arg Val Ile Gln Cys Phe Ala Pro Gly Ile Pro
        355                 360                 365 caa att tat tat gtt ggt tta ctt gct ggc aaa aat gat att gac ctt     1152
Gln Ile Tyr Tyr Val Gly Leu Leu Ala Gly Lys Asn Asp Ile Asp Leu
    370                 375                 380 tta gag gaa aca aaa gaa ggg cgt aat att aat cgt cat tac tac aca     1200
Leu Glu Glu Thr Lys Glu Gly Arg Asn Ile Asn Arg His Tyr Tyr Thr
385                 390                 395                 400 ata gat gaa att aaa aat gaa gta aaa aga cca gtt gtt aaa gcg ttg     1248
Ile Asp Glu Ile Lys Asn Glu Val Lys Arg Pro Val Val Lys Ala Leu
                405                 410                 415 tgc aat tta ctg agg ttt aga aat act tct gaa gcg ttt gat ttg gaa     1296
Cys Asn Leu Leu Arg Phe Arg Asn Thr Ser Glu Ala Phe Asp Leu Glu
            420                 425                 430 gga agt ata gaa att gag aca cct agc tca aat gaa atc gtt att att     1344
Gly Ser Ile Glu Ile Glu Thr Pro Ser Ser Asn Glu Ile Val Ile Ile
        435                 440                 445 cgc aaa aac aaa aca aat aaa att aca gcg aca tta aaa gca aat tta     1392
Arg Lys Asn Lys Thr Asn Lys Ile Thr Ala Thr Leu Lys Ala Asn Leu
    450                 455                 460 agt act aaa aca ttc caa atc agc gaa aat gaa aga aat att tta att     1440
Ser Thr Lys Thr Phe Gln Ile Ser Glu Asn Glu Arg Asn Ile Leu Ile
465                 470                 475                 480 taa                                                                 1443

<210> SEQ ID NO 20
<211> LENGTH: 480
<212> TYPE: PRT
<213> ORGANISM: Listeria monocytogenes

<400> SEQUENCE: 20

Met Gln Ile Lys Asn Lys Ala Met Leu Ile Thr Tyr Ser Asp Ser Leu
1               5                   10                  15

Gly Lys Asn Met Glu Glu Leu Ser Lys Val Met Glu Thr Tyr Phe Glu
            20                  25                  30

Asp Ala Val Gly Gly Ile His Leu Leu Pro Phe Phe Pro Ser Thr Gly
        35                  40                  45
```

-continued

Asp Arg Gly Phe Ala Pro Ser Asp Tyr Thr Thr Val Asp Ser Asp Leu
    50                  55                  60

Gly Ser Trp Glu Ile Ile Glu Lys Leu Gly Glu Lys Tyr Tyr Leu Met
65                  70                  75                  80

Phe Asp Phe Met Ile Asn His Ile Ser Arg Glu Ser Leu Phe Phe Gln
                    85                  90                  95

Asp Phe Lys Lys Glu His Leu Asn Ser Lys Tyr Lys Asp Met Phe Ile
                100                 105                 110

Arg Ile Asn Asp Phe Phe Pro Pro Gly Arg Pro Asn Glu Lys Asp Leu
            115                 120                 125

Asp Leu Ile Tyr Lys Arg Lys Asp Lys Ala Pro Phe Gln Glu Val Glu
        130                 135                 140

Phe Ala Asp Gly Gly Thr Glu Leu Val Trp Asn Thr Phe Gly Glu Glu
145                 150                 155                 160

Gln Ile Asp Leu Asp Val Thr Ala Glu Val Thr Lys Glu Phe Ile Arg
                165                 170                 175

Gln Thr Ile Lys Asn Met Ala Ala His Gly Cys Ser Ile Leu Arg Leu
                180                 185                 190

Asp Ala Phe Ala Tyr Ala Ile Lys Lys Leu Asp Thr Asn Asp Phe Phe
            195                 200                 205

Val Glu Pro Glu Ile Trp Asp Leu Leu Asp Glu Val Lys Ala Glu Ala
        210                 215                 220

Ala Lys Tyr Asp Met Glu Leu Leu Pro Glu Ile His Glu His Tyr Ser
225                 230                 235                 240

Ile Gln Met Lys Ile Ala Asn His Asp Tyr Tyr Ile Tyr Asp Phe Ala
                245                 250                 255

Leu Pro Met Val Met Leu Tyr Ser Leu Tyr Ser Gly Arg Val Glu Arg
                260                 265                 270

Leu Ala Lys Trp Leu Glu Met Ser Pro Met Lys Gln Phe Thr Thr Leu
            275                 280                 285

Asp Thr His Asp Gly Ile Gly Val Val Asp Ala Arg Asp Leu Leu Thr
        290                 295                 300

Asp Glu Glu Leu Asp Tyr Thr Ser Ala Glu Leu Tyr Lys Ile Gly Ala
305                 310                 315                 320

Asn Val Lys Lys Ile Tyr Ser Ser Glu Lys Tyr Asn Asn Leu Asp Ile
                325                 330                 335

Tyr Gln Ile Asn Ser Thr Tyr Tyr Ser Ala Leu Gly Asp Asp Asp Lys
                340                 345                 350

Ser Tyr Leu Leu Ala Arg Val Ile Gln Cys Phe Ala Pro Gly Ile Pro
            355                 360                 365

Gln Ile Tyr Tyr Val Gly Leu Leu Ala Gly Lys Asn Asp Ile Asp Leu
        370                 375                 380

Leu Glu Glu Thr Lys Glu Gly Arg Asn Ile Asn Arg His Tyr Tyr Thr
385                 390                 395                 400

Ile Asp Glu Ile Lys Asn Glu Val Lys Arg Pro Val Val Lys Ala Leu
                405                 410                 415

Cys Asn Leu Leu Arg Phe Arg Asn Thr Ser Glu Ala Phe Asp Leu Glu
                420                 425                 430

Gly Ser Ile Glu Ile Glu Thr Pro Ser Ser Asn Glu Ile Val Ile Ile
            435                 440                 445

Arg Lys Asn Lys Thr Asn Lys Ile Thr Ala Thr Leu Lys Ala Asn Leu
        450                 455                 460

Ser Thr Lys Thr Phe Gln Ile Ser Glu Asn Glu Arg Asn Ile Leu Ile

<210> SEQ ID NO 21
<211> LENGTH: 1443
<212> TYPE: DNA
<213> ORGANISM: Artificial Sequence
<220> FEATURE:
<223> OTHER INFORMATION: A mutant of Streptococcus mutans sucrose phyophorylase
<220> FEATURE:
<221> NAME/KEY: CDS
<222> LOCATION: (1)..(1443)

<400> SEQUENCE: 21

| | | | | | | | | | | | | | | | | |
|---|---|---|---|---|---|---|---|---|---|---|---|---|---|---|---|---|
| atg | cca | att | aca | aat | aaa | aca | atg | ttg | att | act | tac | gca | gac | agt | ttg | 48 |
| Met | Pro | Ile | Thr | Asn | Lys | Thr | Met | Leu | Ile | Thr | Tyr | Ala | Asp | Ser | Leu | |
| 1 | | | | 5 | | | | | 10 | | | | | 15 | | |
| ggt | aaa | aat | ttg | aaa | gaa | ttg | aat | gaa | aat | att | gag | aat | tat | ttt | gga | 96 |
| Gly | Lys | Asn | Leu | Lys | Glu | Leu | Asn | Glu | Asn | Ile | Glu | Asn | Tyr | Phe | Gly | |
| | | | 20 | | | | | 25 | | | | | 30 | | | |
| gat | gct | gtt | ggc | ggt | gtc | cat | ttg | ctg | cca | ttc | ttt | cct | tcc | tca | ggt | 144 |
| Asp | Ala | Val | Gly | Gly | Val | His | Leu | Leu | Pro | Phe | Phe | Pro | Ser | Ser | Gly | |
| | | | 35 | | | | | 40 | | | | | 45 | | | |
| gat | cgt | ggc | ttt | gca | ccg | att | gat | tac | cat | gaa | gtt | gac | cct | gct | ttt | 192 |
| Asp | Arg | Gly | Phe | Ala | Pro | Ile | Asp | Tyr | His | Glu | Val | Asp | Pro | Ala | Phe | |
| | 50 | | | | | 55 | | | | | 60 | | | | | |
| ggc | gat | tgg | gat | gat | gtc | aaa | cgt | ttg | ggt | gaa | aaa | cat | tac | ctc | atg | 240 |
| Gly | Asp | Trp | Asp | Asp | Val | Lys | Arg | Leu | Gly | Glu | Lys | His | Tyr | Leu | Met | |
| 65 | | | | | 70 | | | | | 75 | | | | | 80 | |
| ttt | gat | ttc | atg | att | aat | cat | att | tcg | cgt | cag | tct | aaa | tat | tat | aaa | 288 |
| Phe | Asp | Phe | Met | Ile | Asn | His | Ile | Ser | Arg | Gln | Ser | Lys | Tyr | Tyr | Lys | |
| | | | | 85 | | | | | 90 | | | | | 95 | | |
| gat | tac | caa | gaa | aag | cat | gaa | gca | agt | gct | tat | aaa | gat | cta | ttt | tta | 336 |
| Asp | Tyr | Gln | Glu | Lys | His | Glu | Ala | Ser | Ala | Tyr | Lys | Asp | Leu | Phe | Leu | |
| | | | 100 | | | | | 105 | | | | | 110 | | | |
| aat | tgg | gat | aaa | ttt | tgg | cct | aaa | aat | cgc | ccg | aca | caa | gaa | gat | ctg | 384 |
| Asn | Trp | Asp | Lys | Phe | Trp | Pro | Lys | Asn | Arg | Pro | Thr | Gln | Glu | Asp | Leu | |
| | | | 115 | | | | | 120 | | | | | 125 | | | |
| gac | ctg | att | tat | aag | cgt | aag | gat | cga | gca | cct | atg | cag | gaa | atc | cga | 432 |
| Asp | Leu | Ile | Tyr | Lys | Arg | Lys | Asp | Arg | Ala | Pro | Met | Gln | Glu | Ile | Arg | |
| | 130 | | | | | 135 | | | | | 140 | | | | | |
| ttt | gca | gat | ggc | agt | gtt | gaa | cat | ctc | tgg | agc | act | ttt | ggg | gag | gaa | 480 |
| Phe | Ala | Asp | Gly | Ser | Val | Glu | His | Leu | Trp | Ser | Thr | Phe | Gly | Glu | Glu | |
| 145 | | | | | 150 | | | | | 155 | | | | | 160 | |
| cag | att | gat | ctt | gac | gtg | act | aaa | gaa | gtg | act | atg | gat | ttt | att | cgc | 528 |
| Gln | Ile | Asp | Leu | Asp | Val | Thr | Lys | Glu | Val | Thr | Met | Asp | Phe | Ile | Arg | |
| | | | | 165 | | | | | 170 | | | | | 175 | | |
| tct | acc | att | gaa | aat | tta | gca | gcc | aac | ggc | tgt | gat | ctc | att | cgt | ttg | 576 |
| Ser | Thr | Ile | Glu | Asn | Leu | Ala | Ala | Asn | Gly | Cys | Asp | Leu | Ile | Arg | Leu | |
| | | | 180 | | | | | 185 | | | | | 190 | | | |
| gat | gcc | ttt | gct | tat | gct | gtt | aaa | aag | cta | gat | acg | aat | gat | ttc | ttt | 624 |
| Asp | Ala | Phe | Ala | Tyr | Ala | Val | Lys | Lys | Leu | Asp | Thr | Asn | Asp | Phe | Phe | |
| | | | 195 | | | | | 200 | | | | | 205 | | | |
| gtt | gaa | cct | gaa | atc | tgg | act | ctg | cta | gat | aaa | gtt | cgt | gat | ata | gct | 672 |
| Val | Glu | Pro | Glu | Ile | Trp | Thr | Leu | Leu | Asp | Lys | Val | Arg | Asp | Ile | Ala | |
| | 210 | | | | | 215 | | | | | 220 | | | | | |
| gct | gta | tcg | ggt | gcg | gaa | atc | ttg | ccg | gaa | att | cat | gaa | cac | tat | act | 720 |
| Ala | Val | Ser | Gly | Ala | Glu | Ile | Leu | Pro | Glu | Ile | His | Glu | His | Tyr | Thr | |
| 225 | | | | | 230 | | | | | 235 | | | | | 240 | |
| att | caa | ttt | aaa | att | gca | gac | cat | ggt | tac | tat | gtt | tat | gat | ttt | gcc | 768 |
| Ile | Gln | Phe | Lys | Ile | Ala | Asp | His | Gly | Tyr | Tyr | Val | Tyr | Asp | Phe | Ala | |
| | | | | 245 | | | | | 250 | | | | | 255 | | |

```
ctg cct atg gtg acg ctc tac agc cta tat tcg ggc aag gtt gac cgt       816
Leu Pro Met Val Thr Leu Tyr Ser Leu Tyr Ser Gly Lys Val Asp Arg
        260                 265                 270 ctt gcc aaa tgg ctg aaa atg agt ccg atg aaa cag ttc acc acc ctt       864
Leu Ala Lys Trp Leu Lys Met Ser Pro Met Lys Gln Phe Thr Thr Leu
    275                 280                 285 gat aca cat gac ggt att ggt gtg gtt gat gtt aag gat atc ctg act       912
Asp Thr His Asp Gly Ile Gly Val Val Asp Val Lys Asp Ile Leu Thr
290                 295                 300 gac gaa gaa att acc tat act tct aat gag ctt tat aag gtc ggt gcc       960
Asp Glu Glu Ile Thr Tyr Thr Ser Asn Glu Leu Tyr Lys Val Gly Ala
305                 310                 315                 320 aat gtc aat cgt aag tat tca act gcc gaa tat aat aac ttg gat atc      1008
Asn Val Asn Arg Lys Tyr Ser Thr Ala Glu Tyr Asn Asn Leu Asp Ile
                325                 330                 335 tat caa att aat tca act tac tat tca gca ctt ggt gat gat gat caa      1056
Tyr Gln Ile Asn Ser Thr Tyr Tyr Ser Ala Leu Gly Asp Asp Asp Gln
            340                 345                 350 aaa tac ttt ttg gcc cgc ttg ata caa gct ttt gct cca ggt att cca      1104
Lys Tyr Phe Leu Ala Arg Leu Ile Gln Ala Phe Ala Pro Gly Ile Pro
        355                 360                 365 cag gtt tat tac gtt ggc ttt tta gct ggc aag aat gat ctt gaa tta      1152
Gln Val Tyr Tyr Val Gly Phe Leu Ala Gly Lys Asn Asp Leu Glu Leu
    370                 375                 380 ctg gaa agc act aaa gaa ggc cgc aat atc aac cgt cat tat tat agt      1200
Leu Glu Ser Thr Lys Glu Gly Arg Asn Ile Asn Arg His Tyr Tyr Ser
385                 390                 395                 400 agt gaa gaa att gct aag gaa gtg aag cgg cca gtt gtc aag gca ctt      1248
Ser Glu Glu Ile Ala Lys Glu Val Lys Arg Pro Val Val Lys Ala Leu
                405                 410                 415 tta aat ctc ttt act tac cgc aat cag tca gca gct ttt gat ttg gat      1296
Leu Asn Leu Phe Thr Tyr Arg Asn Gln Ser Ala Ala Phe Asp Leu Asp
            420                 425                 430 ggc cgt att gaa gtg gaa acg cca aat gaa gcg acc att gtc ata gaa      1344
Gly Arg Ile Glu Val Glu Thr Pro Asn Glu Ala Thr Ile Val Ile Glu
        435                 440                 445 cgt caa aat aaa gat ggc agt cat atc gca aca gca gag att aat ctc      1392
Arg Gln Asn Lys Asp Gly Ser His Ile Ala Thr Ala Glu Ile Asn Leu
    450                 455                 460 caa gat atg aca tac aga gta aca gaa aat gat caa aca ata agc ttt      1440
Gln Asp Met Thr Tyr Arg Val Thr Glu Asn Asp Gln Thr Ile Ser Phe
465                 470                 475                 480 gaa                                                                  1443
Glu

<210> SEQ ID NO 22
<211> LENGTH: 481
<212> TYPE: PRT
<213> ORGANISM: Artificial Sequence
<220> FEATURE:
<223> OTHER INFORMATION: Synthetic Construct

<400> SEQUENCE: 22

Met Pro Ile Thr Asn Lys Thr Met Leu Ile Thr Tyr Ala Asp Ser Leu
1               5                   10                  15

Gly Lys Asn Leu Lys Glu Leu Asn Glu Asn Ile Glu Asn Tyr Phe Gly
            20                  25                  30

Asp Ala Val Gly Gly Val His Leu Leu Pro Phe Phe Pro Ser Ser Gly
        35                  40                  45

Asp Arg Gly Phe Ala Pro Ile Asp Tyr His Glu Val Asp Pro Ala Phe
    50                  55                  60
```

-continued

```
Gly Asp Trp Asp Asp Val Lys Arg Leu Gly Glu Lys His Tyr Leu Met
 65                  70                  75                  80

Phe Asp Phe Met Ile Asn His Ile Ser Arg Gln Ser Lys Tyr Tyr Lys
                 85                  90                  95

Asp Tyr Gln Glu Lys His Glu Ala Ser Ala Tyr Lys Asp Leu Phe Leu
            100                 105                 110

Asn Trp Asp Lys Phe Trp Pro Lys Asn Arg Pro Thr Gln Glu Asp Leu
        115                 120                 125

Asp Leu Ile Tyr Lys Arg Lys Asp Arg Ala Pro Met Gln Glu Ile Arg
    130                 135                 140

Phe Ala Asp Gly Ser Val Glu His Leu Trp Ser Thr Phe Gly Glu Glu
145                 150                 155                 160

Gln Ile Asp Leu Asp Val Thr Lys Glu Val Thr Met Asp Phe Ile Arg
                165                 170                 175

Ser Thr Ile Glu Asn Leu Ala Ala Asn Gly Cys Asp Leu Ile Arg Leu
            180                 185                 190

Asp Ala Phe Ala Tyr Ala Val Lys Lys Leu Asp Thr Asn Asp Phe Phe
        195                 200                 205

Val Glu Pro Glu Ile Trp Thr Leu Leu Asp Lys Val Arg Asp Ile Ala
    210                 215                 220

Ala Val Ser Gly Ala Glu Ile Leu Pro Glu Ile His Glu His Tyr Thr
225                 230                 235                 240

Ile Gln Phe Lys Ile Ala Asp His Gly Tyr Tyr Val Tyr Asp Phe Ala
                245                 250                 255

Leu Pro Met Val Thr Leu Tyr Ser Leu Tyr Ser Gly Lys Val Asp Arg
            260                 265                 270

Leu Ala Lys Trp Leu Lys Met Ser Pro Met Lys Gln Phe Thr Thr Leu
        275                 280                 285

Asp Thr His Asp Gly Ile Gly Val Val Asp Val Lys Asp Ile Leu Thr
    290                 295                 300

Asp Glu Glu Ile Thr Tyr Thr Ser Asn Glu Leu Tyr Lys Val Gly Ala
305                 310                 315                 320

Asn Val Asn Arg Lys Tyr Ser Thr Ala Glu Tyr Asn Asn Leu Asp Ile
                325                 330                 335

Tyr Gln Ile Asn Ser Thr Tyr Tyr Ser Ala Leu Gly Asp Asp Asp Gln
            340                 345                 350

Lys Tyr Phe Leu Ala Arg Leu Ile Gln Ala Phe Ala Pro Gly Ile Pro
        355                 360                 365

Gln Val Tyr Tyr Val Gly Phe Leu Ala Gly Lys Asn Asp Leu Glu Leu
    370                 375                 380

Leu Glu Ser Thr Lys Glu Gly Arg Asn Ile Asn Arg His Tyr Tyr Ser
385                 390                 395                 400

Ser Glu Glu Ile Ala Lys Glu Val Lys Arg Pro Val Val Lys Ala Leu
                405                 410                 415

Leu Asn Leu Phe Thr Tyr Arg Asn Gln Ser Ala Ala Phe Asp Leu Asp
            420                 425                 430

Gly Arg Ile Glu Val Glu Thr Pro Asn Glu Ala Thr Ile Val Ile Glu
        435                 440                 445

Arg Gln Asn Lys Asp Gly Ser His Ile Ala Thr Ala Glu Ile Asn Leu
    450                 455                 460

Gln Asp Met Thr Tyr Arg Val Thr Glu Asn Asp Gln Thr Ile Ser Phe
465                 470                 475                 480

Glu
```

<210> SEQ ID NO 23
<211> LENGTH: 1461
<212> TYPE: DNA
<213> ORGANISM: Artificial Sequence
<220> FEATURE:
<223> OTHER INFORMATION: A mutant of Streptococcus mutans sucrose phyophorylase
<220> FEATURE:
<221> NAME/KEY: CDS
<222> LOCATION: (1)..(1461)

<400> SEQUENCE: 23

```
atg cca att aca aat aaa aca atg ttg att act tac gca gac agt ttg      48
Met Pro Ile Thr Asn Lys Thr Met Leu Ile Thr Tyr Ala Asp Ser Leu
1               5                   10                  15 ggt aaa aat ttg aaa gaa ttg aat gaa aat att gag aat tat ttt gga      96
Gly Lys Asn Leu Lys Glu Leu Asn Glu Asn Ile Glu Asn Tyr Phe Gly
            20                  25                  30 gat gct gtt ggc ggt gtc cat ttg ctg cca ttc ttt cct tcc aca ggt     144
Asp Ala Val Gly Gly Val His Leu Leu Pro Phe Phe Pro Ser Thr Gly
        35                  40                  45 gat cgt ggc ttt gca ccg att gat tac cat gaa gtt gac tct gct ttt     192
Asp Arg Gly Phe Ala Pro Ile Asp Tyr His Glu Val Asp Ser Ala Phe
    50                  55                  60 ggc gat tgg gat gat gtc aaa cgt ttg ggt gaa aaa tat tac ctc atg     240
Gly Asp Trp Asp Asp Val Lys Arg Leu Gly Glu Lys Tyr Tyr Leu Met
65                  70                  75                  80 ttt gat ttc atg att aat cat att tcg cgt cag tct aaa tat tat aaa     288
Phe Asp Phe Met Ile Asn His Ile Ser Arg Gln Ser Lys Tyr Tyr Lys
                85                  90                  95 gat tac caa gaa aag cat gaa gca agt gct tat aaa gat cta ttt tta     336
Asp Tyr Gln Glu Lys His Glu Ala Ser Ala Tyr Lys Asp Leu Phe Leu
            100                 105                 110 aat tgg gat aaa ttt tgg cct aaa aat cgc ccg aca caa gaa gat gtg     384
Asn Trp Asp Lys Phe Trp Pro Lys Asn Arg Pro Thr Gln Glu Asp Val
        115                 120                 125 gac ctg att tat aag cgt aag gat cga gca cct aag cag gaa atc caa     432
Asp Leu Ile Tyr Lys Arg Lys Asp Arg Ala Pro Lys Gln Glu Ile Gln
    130                 135                 140 ttt gca gat ggc agt gtt gaa cat ctc tgg aac act ttt ggg gag gaa     480
Phe Ala Asp Gly Ser Val Glu His Leu Trp Asn Thr Phe Gly Glu Glu
145                 150                 155                 160 cag att gat ctt gac gtg act aaa gaa gtg act atg gat ttt att cgc     528
Gln Ile Asp Leu Asp Val Thr Lys Glu Val Thr Met Asp Phe Ile Arg
                165                 170                 175 tct acc att gaa aat tta gca gcc aac ggc tgt gat ctc att cgt ttg     576
Ser Thr Ile Glu Asn Leu Ala Ala Asn Gly Cys Asp Leu Ile Arg Leu
            180                 185                 190 gat gcc ttt gct tat gct gtt aaa aag cta gat acg aat gat ttc ttt     624
Asp Ala Phe Ala Tyr Ala Val Lys Lys Leu Asp Thr Asn Asp Phe Phe
        195                 200                 205 gtt gaa cct gaa atc tgg act ctg cta gat aaa gtt cgt gat ata gct     672
Val Glu Pro Glu Ile Trp Thr Leu Leu Asp Lys Val Arg Asp Ile Ala
    210                 215                 220 gct gta tcg ggt gcg gaa atc ttg ccg gaa att cat gaa cac tat act     720
Ala Val Ser Gly Ala Glu Ile Leu Pro Glu Ile His Glu His Tyr Thr
225                 230                 235                 240 att caa ttt aaa att gca gac cat gat tac tat gtt tat gat ttt gcc     768
Ile Gln Phe Lys Ile Ala Asp His Asp Tyr Tyr Val Tyr Asp Phe Ala
                245                 250                 255 ctg cct atg gtg acg ctc tac agc cta tat tcg ggc aag gtt gac cgt     816
```

```
                                                                          864
ctt gcc aaa tgg ctg aaa atg agt ccg atg aaa cag ttc acc acc ctt
Leu Ala Lys Trp Leu Lys Met Ser Pro Met Lys Gln Phe Thr Thr Leu
        275                 280                 285

912
gat aca cat gac ggt att ggt gtg gtt gat gtt aag gat atc ctg act
Asp Thr His Asp Gly Ile Gly Val Val Asp Val Lys Asp Ile Leu Thr
    290                 295                 300

960
gac gaa gaa att acc tat act tct aat gag ctt tat aag gtc ggt gcc
Asp Glu Glu Ile Thr Tyr Thr Ser Asn Glu Leu Tyr Lys Val Gly Ala
305                 310                 315                 320

1008
aat gtc aat cgt aag tat tca act gcc gaa tat aat aac ttg gat atc
Asn Val Asn Arg Lys Tyr Ser Thr Ala Glu Tyr Asn Asn Leu Asp Ile
                325                 330                 335

1056
tat caa att aat tca act tac tat tca gca ctt ggt gat gat gat caa
Tyr Gln Ile Asn Ser Thr Tyr Tyr Ser Ala Leu Gly Asp Asp Asp Gln
            340                 345                 350

1104
aaa tac ttt ttg gcc cgc ttg ata caa gct ttt gct cca ggt att cca
Lys Tyr Phe Leu Ala Arg Leu Ile Gln Ala Phe Ala Pro Gly Ile Pro
        355                 360                 365

1152
cag gtt tat tac gtt ggc ttt tta gct ggc aag aat gat ctt gaa tta
Gln Val Tyr Tyr Val Gly Phe Leu Ala Gly Lys Asn Asp Leu Glu Leu
    370                 375                 380

1200
ctg gaa agc act aaa gaa ggc cgc aat atc aac cgt cat tat tat agt
Leu Glu Ser Thr Lys Glu Gly Arg Asn Ile Asn Arg His Tyr Tyr Ser
385                 390                 395                 400

1248
agt gaa gaa att gct aag gaa gtg aag cgg cca gtt gtc aag gca ctt
Ser Glu Glu Ile Ala Lys Glu Val Lys Arg Pro Val Val Lys Ala Leu
                405                 410                 415

1296
tta aat ctc ttt act tac cgc aat cag tca gca gct ttt gat ttg gat
Leu Asn Leu Phe Thr Tyr Arg Asn Gln Ser Ala Ala Phe Asp Leu Asp
            420                 425                 430

1344
ggc cgt att gaa gtg gaa acg cca aat gaa gcg acc att gtc ata gaa
Gly Arg Ile Glu Val Glu Thr Pro Asn Glu Ala Thr Ile Val Ile Glu
        435                 440                 445

1392
cgt caa aat aaa gat ggc agt cat atc gca aca gca gag att aat ctc
Arg Gln Asn Lys Asp Gly Ser His Ile Ala Thr Ala Glu Ile Asn Leu
    450                 455                 460

1440
caa gat atg aca tac aga gta aca gaa aat gat caa aca ata agc tta
Gln Asp Met Thr Tyr Arg Val Thr Glu Asn Asp Gln Thr Ile Ser Leu
465                 470                 475                 480

1461
tcc atg ata agc tgt caa aca
Ser Met Ile Ser Cys Gln Thr
                485
```

<210> SEQ ID NO 24
<211> LENGTH: 487
<212> TYPE: PRT
<213> ORGANISM: Artificial Sequence
<220> FEATURE:
<223> OTHER INFORMATION: Synthetic Construct

<400> SEQUENCE: 24

Met Pro Ile Thr Asn Lys Thr Met Leu Ile Thr Tyr Ala Asp Ser Leu
1               5                   10                  15

Gly Lys Asn Leu Lys Glu Leu Asn Glu Asn Ile Glu Asn Tyr Phe Gly
            20                  25                  30

Asp Ala Val Gly Gly Val His Leu Leu Pro Phe Phe Pro Ser Thr Gly
        35                  40                  45

Asp Arg Gly Phe Ala Pro Ile Asp Tyr His Glu Val Asp Ser Ala Phe
    50                  55                  60

```
Gly Asp Trp Asp Asp Val Lys Arg Leu Gly Glu Lys Tyr Tyr Leu Met
 65                  70                  75                  80

Phe Asp Phe Met Ile Asn His Ile Ser Arg Gln Ser Lys Tyr Tyr Lys
                 85                  90                  95

Asp Tyr Gln Glu Lys His Glu Ala Ser Ala Tyr Lys Asp Leu Phe Leu
            100                 105                 110

Asn Trp Asp Lys Phe Trp Pro Lys Asn Arg Pro Thr Gln Glu Asp Val
            115                 120                 125

Asp Leu Ile Tyr Lys Arg Lys Asp Arg Ala Pro Lys Gln Glu Ile Gln
        130                 135                 140

Phe Ala Asp Gly Ser Val Glu His Leu Trp Asn Thr Phe Gly Glu Glu
145                 150                 155                 160

Gln Ile Asp Leu Asp Val Thr Lys Glu Val Thr Met Asp Phe Ile Arg
                165                 170                 175

Ser Thr Ile Glu Asn Leu Ala Ala Asn Gly Cys Asp Leu Ile Arg Leu
                180                 185                 190

Asp Ala Phe Ala Tyr Ala Val Lys Lys Leu Asp Thr Asn Asp Phe Phe
            195                 200                 205

Val Glu Pro Glu Ile Trp Thr Leu Leu Asp Lys Val Arg Asp Ile Ala
210                 215                 220

Ala Val Ser Gly Ala Glu Ile Leu Pro Glu Ile His Glu His Tyr Thr
225                 230                 235                 240

Ile Gln Phe Lys Ile Ala Asp His Asp Tyr Tyr Val Tyr Asp Phe Ala
                245                 250                 255

Leu Pro Met Val Thr Leu Tyr Ser Leu Tyr Ser Gly Lys Val Asp Arg
            260                 265                 270

Leu Ala Lys Trp Leu Lys Met Ser Pro Met Lys Gln Phe Thr Thr Leu
        275                 280                 285

Asp Thr His Asp Gly Ile Gly Val Val Asp Val Lys Asp Ile Leu Thr
        290                 295                 300

Asp Glu Glu Ile Thr Tyr Thr Ser Asn Glu Leu Tyr Lys Val Gly Ala
305                 310                 315                 320

Asn Val Asn Arg Lys Tyr Ser Thr Ala Glu Tyr Asn Asn Leu Asp Ile
                325                 330                 335

Tyr Gln Ile Asn Ser Thr Tyr Tyr Ser Ala Leu Gly Asp Asp Gln
                340                 345                 350

Lys Tyr Phe Leu Ala Arg Leu Ile Gln Ala Phe Ala Pro Gly Ile Pro
            355                 360                 365

Gln Val Tyr Tyr Val Gly Phe Leu Ala Gly Lys Asn Asp Leu Glu Leu
        370                 375                 380

Leu Glu Ser Thr Lys Glu Gly Arg Asn Ile Asn Arg His Tyr Tyr Ser
385                 390                 395                 400

Ser Glu Glu Ile Ala Lys Glu Val Lys Arg Pro Val Val Lys Ala Leu
                405                 410                 415

Leu Asn Leu Phe Thr Tyr Arg Asn Gln Ser Ala Ala Phe Asp Leu Asp
            420                 425                 430

Gly Arg Ile Glu Val Glu Thr Pro Asn Glu Ala Thr Ile Val Ile Glu
        435                 440                 445

Arg Gln Asn Lys Asp Gly Ser His Ile Ala Thr Ala Glu Ile Asn Leu
        450                 455                 460

Gln Asp Met Thr Tyr Arg Val Thr Glu Asn Asp Gln Thr Ile Ser Leu
465                 470                 475                 480

Ser Met Ile Ser Cys Gln Thr
```

```
<210> SEQ ID NO 25
<211> LENGTH: 56
<212> TYPE: PRT
<213> ORGANISM: Streptococcus mutans

<400> SEQUENCE: 25

Ala Val Gly Gly Val His Leu Leu Pro Phe Phe Pro Ser Thr Gly Asp
1               5                   10                  15

Arg Gly Phe Ala Pro Ile Asp Tyr His Glu Val Asp Ser Ala Phe Gly
            20                  25                  30

Asp Trp Asp Asp Val Lys Arg Leu Gly Glu Lys Tyr Tyr Leu Met Phe
        35                  40                  45

Asp Phe Met Ile Asn His Ile Ser
    50                  55

<210> SEQ ID NO 26
<211> LENGTH: 42
<212> TYPE: PRT
<213> ORGANISM: Streptococcus mutans

<400> SEQUENCE: 26

Arg Pro Thr Gln Glu Asp Val Asp Leu Ile Tyr Lys Arg Lys Asp Arg
1               5                   10                  15

Ala Pro Lys Gln Glu Ile Gln Phe Ala Asp Gly Ser Val Glu His Leu
            20                  25                  30

Trp Asn Thr Phe Gly Glu Glu Gln Ile Asp
        35                  40

<210> SEQ ID NO 27
<211> LENGTH: 38
<212> TYPE: PRT
<213> ORGANISM: Streptococcus mutans

<400> SEQUENCE: 27

Ile Leu Pro Glu Ile His Glu His Tyr Thr Ile Gln Phe Lys Ile Ala
1               5                   10                  15

Asp His Asp Tyr Tyr Val Tyr Asp Phe Ala Leu Pro Met Val Thr Leu
            20                  25                  30

Tyr Ser Leu Tyr Ser Gly
        35
```